(12) United States Patent
Kushibe et al.

(10) Patent No.: US 10,799,191 B2
(45) Date of Patent: Oct. 13, 2020

(54) STREAKLINE VISUALIZATION APPARATUS AND METHOD

(71) Applicants: FUJITSU LIMITED, Kawasaki-shi, Kanagawa (JP); The University of Tokyo, Bunkyo-ku, Tokyo (JP)

(72) Inventors: Daisuke Kushibe, Kawasaki (JP); Masahiro Watanabe, Kawasaki (JP); Toshiaki Hisada, Kashiwa (JP); Seiryo Sugiura, Bunkyo (JP); Takumi Washio, Bunkyo (JP); Jun-Ichi Okada, Bunkyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 442 days.

(21) Appl. No.: 15/827,579

(22) Filed: Nov. 30, 2017

(65) Prior Publication Data

US 2018/0153483 A1      Jun. 7, 2018

(30) Foreign Application Priority Data

Dec. 6, 2016 (JP) ................................ 2016-236734
Apr. 6, 2017 (JP) ................................ 2017-075671

(51) Int. Cl.
*A61B 6/03* (2006.01)
*A61B 6/00* (2006.01)
(Continued)

(52) U.S. Cl.
CPC .............. *A61B 6/032* (2013.01); *A61B 6/504* (2013.01); *A61B 6/507* (2013.01); *A61B 6/5217* (2013.01);
(Continued)

(58) Field of Classification Search
None
See application file for complete search history.

(56) References Cited

U.S. PATENT DOCUMENTS

| | | | |
|---|---|---|---|
| 8,744,818 B2 * | 6/2014 | Ueda ....................... | G06F 30/00 703/6 |
| 2006/0074610 A1 * | 4/2006 | Rasmussen ............. | G06F 30/23 703/2 |

(Continued)

FOREIGN PATENT DOCUMENTS

| | | |
|---|---|---|
| JP | 2003-6552 | 1/2003 |
| JP | 2015-97759 | 5/2015 |
| WO | WO 2016/056642 A1 | 4/2016 |

OTHER PUBLICATIONS

Lane, David A., "UFAT—A Particle Tracer for Time-Dependent Flow Fields", 1994, IEEE. (Year: 1994).*

(Continued)

*Primary Examiner* — Cedric Johnson
(74) *Attorney, Agent, or Firm* — Xsensus LLP

(57) ABSTRACT

In a streakline visualization apparatus, a processing unit calculates, by using an expression including a correction value for correcting an error attributable to accelerated motion of a plurality of grid points represented by position information, time differential values of velocities of fluid on the plurality of grid points at each of the plurality of first time points. The processing unit calculates, based on the velocities and the time differential values of the velocities of the fluid on the plurality of grid points at each of the plurality of first time points, positions of a series of a plurality of particles sequentially outputted from a particle generation source as analysis time progresses at each of a plurality of second time points having a second time interval shorter (Continued)

than the first time interval. The processing unit generates display information about a streakline indicating the series of the plurality of particles.

10 Claims, 36 Drawing Sheets

(51) Int. Cl.
    *G06F 30/20* (2020.01)
    *G06T 7/00* (2017.01)
    *G06F 30/15* (2020.01)
    *G06F 111/10* (2020.01)
    *G06F 113/28* (2020.01)

(52) U.S. Cl.
    CPC .............. *G06F 30/20* (2020.01); *G06F 30/15* (2020.01); *G06F 2111/10* (2020.01); *G06F 2113/28* (2020.01); *G06T 7/0016* (2013.01); *G06T 2207/30104* (2013.01); *Y02T 90/50* (2018.05)

(56) References Cited

U.S. PATENT DOCUMENTS

2015/0038860 A1* 2/2015 Fonte .................... A61B 5/026 600/505
2015/0120255 A1* 4/2015 King ..................... E21B 43/00 703/2

OTHER PUBLICATIONS

Wen, Chih-Yung et al., "Investigation of Pulsatile Flowfield in Healthy Thoracic Aorta Models", Feb. 2010, Annuals of Biomedical Engineering, vol. 38, No. 2. (Year: 2010).*
Li, Chao et al., "Application of Topology Analysis in Visualization of 2D Dynamic Vector Fields", 2016, IEEE. (Year: 2016).*
Batycky, Roderick, P., "A Three-Dimensional Two-Phase Field Scale Streamline Simulator", Jan. 1997, Department of Petroleum Engineering, Stanford University. (Year: 1997).*

Tino Weinkauf, et al. "Streak Lines as Tangent Curves of a Derived Vector Field", IEEE Transactions on Visualization and Computer Graphics, vol. 16, Issue 6, 2010, 10 pages.
Erwin Fehlberg "Low-Order Classical Runge-Kutta Formulas With Stepsize Control and Their Application to Some Heat Transfer Problems", NASA Technical Report, NASA TR R-315, 1969, 47 pages.
J. Donea, et al. "Arbitrary Lagrangian-Eulerian methods", Encyclopedia of Computational Mechanics, 2004, 38 pages.
Seiryo Sugiura, et al. "Multi-scale simulations of cardiac electrophysiology and mechanics using the University of Tokyo heart simulator", Progress in Biophysics and Molecular Biology, vol. 110, 2012, 10 pages.
William H. Press, et al. "Numerical Recipes in C: The Art of Scientific Computing", 1992, 5 pages.
Extended Search Report dated Apr. 19, 2018 in European Patent Application No. 17203528.9.
David A. Lane, "UFAT—A Particle Tracer for Time-Dependent Flow Fields", Computer Science Corporation, Institute of Electrical and Electronics Engineers, Oct. 17, 1994, vol. Conf. 5, XP000515799, pp. 257-264.
Li Chao, et al., "Application of Topology Analysis in Visualization of 2D Dynamic Vector Fields", IEEE international Conference on Software Engineering and Service Science (ICSESS), Aug. 26, 2016, XP033079954, pp. 641-646.
Chih-Yung Wen, et al., "Investigation of Pulsatile Flowfield in Healthy Thoracic Aorta Models", Annals of Biomedical Engineering, vol. 38, No. 2, Feb. 2010, XP019765897, pp. 391-402.
Extended European Search Report dated Apr. 18, 2018 in European Patent Application No. 17202736.9.
Joseph E. Flaherty "Finite Element Analysis—Chapter 4 Finite Element Approximation", 2005, http://www.cs.rpi.edu/~flaherje/pdf/fea4.pdf, 37 pages.
MicroAVS Support Information, Frequently Asked Questions (FAQ), http://www.cybernet.co.jp/avs/support/microavs/faq/, 13 pages (with English Translation).
Sheldon Imaoka "Using New Meshing Features in ANSYS Workbench Simulation", ANSYS Advantage , vol. II, Issue 2, 2008, 3 pages.
U.S. Office Action dated Apr. 16, 2020, issued in corresponding U.S. Appl. No. 15/827,658.

* cited by examiner

111  GROUP OF ELASTIC BODY INFORMATION FILES stru0002.inp
stru0001.inp

111a  ELASTIC BODY INFORMATION FILE

MYOCARDIAL DATA

| GRID ID | x | y | z |
|---|---|---|---|
| 1 | − 4.8734700E−04 | 1.2971100E−02 | 8.2951500E−02 |
| 2 | − 8.4492100E−03 | 6.7902200E−03 | 8.4463100E−02 |
| 3 | − 2.1713100E−03 | 2.6337800E−02 | 5.9221000E−02 |
| ... | ... | ... | ... |
| N | − 8.4582500E−03 | 1.2153300E−02 | 6.4517600E−02 |

| TETRA ID | GRID ID1 | GRID ID2 | GRID ID3 | GRID ID4 |
|---|---|---|---|---|
| 1 | 39833 | 39836 | 26603 | 28925 |
| 2 | 20856 | 39354 | 111 | 26170 |
| 3 | 42852 | 17600 | 17718 | 74 |
| ... | ... | ... | ... | ... |
| N | 3777 | 5829 | 3823 | 8374 |

| TETRA ID | FORCE kPa |
|---|---|
| 1 | 0.0000000E+00 |
| 2 | 0.0000000E+00 |
| 3 | 2.6207800E−01 |
| ... | ... |
| N | 0.0000000E+00 |

TIME POINT $t = t_0$

TIME POINT $t = t_1 = t_0 + \Delta t$

111b  ELASTIC BODY INFORMATION FILE

FIG. 6

112 GROUP OF FLUID INFORMATION FILES flui0002.inp
flui0001.inp

112a FLUID INFORMATION FILE

BLOOD FLOW DATA

| GRID ID | x | y | z |
|---|---|---|---|
| 1 | − 4.8734700E−04 | 1.2971100E−02 | 8.2951500E−02 |
| 2 | − 8.4492100E−03 | 6.7902200E−03 | 8.4463100E−02 |
| 3 | − 2.1713100E−03 | 2.6337800E−02 | 5.9221000E−02 |
| ... | ... | ... | ... |
| N | − 8.4582500E−03 | 1.2153300E−02 | 6.4517600E−02 |

| TETRA ID | GRID ID1 | GRID ID2 | GRID ID3 | GRID ID4 |
|---|---|---|---|---|
| 1 | 64088 | 64441 | 37425 | 31062 |
| 2 | 64088 | 64441 | 37425 | 37425 |
| 3 | 64088 | 64441 | 37429 | 37465 |
| ... | ... | ... | ... | ... |
| N | 1538 | 9538 | 311 | 2354 |

| GRID ID | vx | vy | vz |
|---|---|---|---|
| 1 | − 3.3427000E−03 | − 3.8634900E−03 | 1.3479400E−02 |
| 2 | − 8.4085600E−03 | − 4.2889500E−03 | 1.0894800E−02 |
| 3 | − 1.5721000E−03 | − 9.6297300E−05 | 1.4328800E−02 |
| ... | ... | ... | ... |
| N | 0.0000000E+00 | 0.0000000E+00 | 0.0000000E+00 |

TIME POINT $t = t_0$

TIME POINT $t = t_1 = t_0 + \Delta t$

112b FLUID INFORMATION FILE

121 PRE-ANALYSIS FILE

121a OUTPUT TIME POINT INDEX TABLE

| Time Index | Time[sec] |
|---|---|
| 0 | 0.000 |
| 2 | 0.010 |
| 3 | 0.020 |
| 4 | 0.030 |
| ... | ... |
| 99 | 0.980 |
| 100 | 0.990 |

121b MYOCARDIUM-SIDE INTERPOLATING POLYNOMIAL COEFFICIENT TABLE

| GRID ID | Time Index | Direction Index | Position [m] | a | b | c | d |
|---|---|---|---|---|---|---|---|
| 1 | 0 | X | 0.03297 | 0.03297 | 0.00425 | −0.58918 | 20.1933 |
| 1 | 0 | Y | 0.01434 | 0.01434 | 0.0023 | −0.10827 | 2.4376 |
| 1 | 0 | Z | 0.07684 | 0.07684 | −0.00098 | −0.03329 | 2.05991 |
| 2 | 0 | X | 0.03294 | 0.03294 | −0.00559 | −1.01999 | 58.5516 |
| 2 | 0 | Y | 0.01427 | 0.01427 | 0.00147 | 1.41681 | −66.3295 |
| 2 | 0 | Z | 0.07683 | 0.07683 | −0.00136 | −0.43743 | 32.3414 |
| ... | ... | ... | ... | ... | ... | ... | ... |
| N | 1 | X | 0.00856 | 0.00856 | −0.00081 | −0.30921 | 11.864 |
| N | 1 | Y | 0.01996 | 0.01996 | 0.00109 | −0.96356 | 46.9359 |
| N | 1 | Z | 0.08661 | 0.08661 | 0.00033 | −0.28274 | 14.6233 |
| ... | ... | ... | ... | ... | ... | ... | ... |
| N | 99 | X | 0.03308 | 0.03308 | −0.0049 | 0.17278 | 0.47014 |
| N | 99 | Y | 0.01578 | 0.01578 | −0.00475 | −0.00316 | 1.38363 |
| N | 99 | Z | 0.07424 | 0.07424 | −0.00319 | 0.05133 | 0.24059 |

121c FLUID-SIDE INTERPOLATING POLYNOMIAL COEFFICIENT TABLE

| GRID ID | Time Index | Direction Index | Position [m] | Velocity [m/s] | a | b | c | d |
|---|---|---|---|---|---|---|---|---|
| 1 | 0 | X | 0.03294 | 0.00401 | 0.03294 | −0.00533 | 1.54806 | −71.2414 |
| 1 | 0 | Y | 0.01435 | −0.00251 | 0.01435 | −0.00757 | 1.09524 | −40.1169 |
| 1 | 0 | Z | 0.07685 | −0.00033 | 0.07685 | −0.00047 | −0.01805 | −0.50782 |
| 2 | 0 | X | 0.03297 | 0.00181 | 0.03297 | 0.00425 | −0.5891 | 20.1933 |
| 2 | 0 | Y | 0.01434 | 0.00094 | 0.01434 | 0.0023 | −0.10827 | 2.4376 |
| 2 | 0 | Z | 0.07684 | −0.00101 | 0.07684 | −0.00098 | −0.03329 | 2.05991 |
| ... | ... | ... | ... | ... | ... | ... | ... | ... |
| N | 0 | X | 0.00867 | −0.00364 | 0.00867 | −0.00036 | 0.01376 | 0.12202 |
| N | 0 | Y | 0.0201 | −0.00245 | 0.0201 | −0.00025 | 0.0255 | 0.28027 |
| N | 0 | Z | 0.08675 | −0.00186 | 0.08675 | −0.00185 | 0.03144 | 0.21764 |
| ... | ... | ... | ... | ... | ... | ... | ... | ... |
| N | 1 | X | 0.03122 | −0.00523 | .3122 | −0.00521 | 0.14046 | −1.31812 |
| N | 1 | Y | 0.01618 | 0.00565 | 0.01618 | 0.00563 | −0.09459 | 1.78342 |
| N | 1 | Z | 0.07568 | 0.00584 | 0.07569 | 0.00584 | −0.05668 | 0.41749 |
| ... | ... | ... | ... | ... | ... | ... | ... | ... |
| N | 99 | X | 0.00977 | −0.00032 | 0.00977 | −0.00032 | 0.0268 | −0.17852 |
| N | 99 | Y | 0.01978 | −0.00253 | 0.01978 | −0.00252 | 0.01961 | 0.5756 |
| N | 99 | Z | 0.06625 | −0.00249 | 0.06625 | −0.0025 | 0.00926 | 0.36747 |

TABLE OF RUNGE-KUTTA
COEFFICIENTS

|     | $\alpha_I$ | $\beta_I$ |
|-----|------------|-----------|
| I=1 | 0          | 0         |
| I=2 | $\Delta t/2$ | $\Delta t/2$ |
| I=3 | $\Delta t/2$ | $\Delta t/2$ |
| I=4 | $\Delta t$ | $\Delta t$ |

STREAKLINE

TIME POINT $t = t_0$

| | POINT 1 ON LINE (COORDINATES) | POINT 2 ON LINE (COORDINATES) | POINT 3 ON LINE (COORDINATES) | ... | POINT M ON LINE (COORDINATES) |
|---|---|---|---|---|---|
| STREAKLINE $l_1$ | (0.0247,0.0274,0.0644) | (0.0247,0.0274,0.0644) | (0.0247,0.0274,0.0644) | ... | (0.0247,0.0274,0.0644) |
| STREAKLINE $l_2$ | (0.0158,0.0422,0.0112) | (0.0158,0.0422,0.0112) | (0.0158,0.0422,0.0112) | ... | (0.0158,0.0422,0.0112) |
| ... | | | | | |
| STREAKLINE $l_M$ | (0.0163,0.0359,0.0115) | (0.0163,0.0359,0.0115) | (0.0163,0.0359,0.0115) | ... | (0.0163,0.0359,0.0115) |

TIME POINT $t = t_1 = t_0 + \Delta t$

| | POINT 1 ON LINE (COORDINATES) | POINT 2 ON LINE (COORDINATES) | POINT 3 ON LINE (COORDINATES) | ... | POINT M ON LINE (COORDINATES) |
|---|---|---|---|---|---|
| STREAKLINE $l_1$ | (0.0241,0.0290,0.0538) | (0.0247,0.0274,0.0644) | (0.0247,0.0274,0.0644) | ... | (0.0247,0.0274,0.0644) |
| STREAKLINE $l_2$ | (0.0137,0.0404,0.0109) | (0.0158,0.0422,0.0112) | (0.0158,0.0422,0.0112) | ... | (0.0158,0.0422,0.0112) |
| ... | | | | | |
| STREAKLINE $l_M$ | (0.0151,0.0341,0.0115) | (0.0163,0.0359,0.0115) | (0.0163,0.0359,0.0115) | ... | (0.0163,0.0359,0.0115) |

TIME POINT $t = t_2 = t_1 + \Delta t$

| | POINT 1 ON LINE (COORDINATES) | POINT 2 ON LINE (COORDINATES) | POINT 3 ON LINE (COORDINATES) | ... | POINT M ON LINE (COORDINATES) |
|---|---|---|---|---|---|
| STREAKLINE $l_1$ | (0.0224,0.0299,0.0455) | (0.0231,0.0285,0.0455) | (0.0247,0.0274,0.0644) | ... | (0.0247,0.0274,0.0644) |
| STREAKLINE $l_2$ | (0.0115,0.0401,0.0108) | (0.0137,0.0405,0.0110) | (0.0158,0.0422,0.0112) | ... | (0.0158,0.0422,0.0112) |
| ... | | | | | |
| STREAKLINE $l_M$ | (0.0147,0.0326,0.0114) | (0.0149,0.0341,0.0115) | (0.0163,0.0359,0.0115) | ... | (0.0163,0.0359,0.0115) |

...

TIME POINT $t = t_N = t_{N-1} + \Delta t$

| | POINT 1 ON LINE (COORDINATES) | POINT 2 ON LINE (COORDINATES) | POINT 3 ON LINE (COORDINATES) | ... | POINT M ON LINE (COORDINATES) |
|---|---|---|---|---|---|
| STREAKLINE $l_1$ | (0.0235,0.0314,0.0439) | (0.0204,0.0272,0.0501) | (0.0205,0.0269,0.0570) | ... | (0.0247,0.0274,0.0644) |
| STREAKLINE $l_2$ | (0.0100,0.0486,0.099) | (0.0095,0.0482,0.0999) | (0.0879,0.0472,0.1000) | ... | (0.0158,0.0422,0.0112) |
| ... | | | | | |
| STREAKLINE $l_M$ | (0.0171,0.0299,0.0246) | (0.0182,0.0315,0.0248) | (0.0207,0.0341,0.0261) | ... | (0.0163,0.0359,0.0115) |

TRUTH TABLE

| STATUS VARIABLE | 0 | 1 | 2 | 3 | 4 |
|---|---|---|---|---|---|
| FLUID DETERMINATION | T | F | F | T | T |
| LINE DETERMINATION | F | T | F | T | T |
| NUMBER OF INTERSECTIONS | 0 | $\neq 0$ | 0 | $\geq 2$ | 1 |

FIG. 22

STREAKLINE VISUALIZATION APPARATUS AND METHOD

CROSS-REFERENCE TO RELATED APPLICATIONS

This application is based upon and claims the benefit of priority of the prior Japanese Patent Application No. 2016-236734, filed on Dec. 6, 2016, and the Japanese Patent Application No. 2017-075671, filed on Apr. 6, 2017, the entire contents of which are incorporated herein by reference.

FIELD

The embodiments discussed herein relate to a streakline visualization apparatus and method.

BACKGROUND

Fluid mechanics is one of the academic fields in mechanics and describes behavior of fluid. Fluid mechanics has been applied to various industrial fields where not only flow of air or water but also transfer of a physical quantity such as the temperature or concentration is handled as a problem. For example, fluid mechanics has been applied to wind tunnel experiments to evaluate prototypes of automobiles, and aerodynamic characteristics of these automobiles have been optimized on the basis of the experiment results. However, these wind tunnel experiments are very costly. Thus, in place of wind tunnel experiments, computer simulations (fluid simulations), which simulate wind tunnel experiments, have been conducted by using computational fluid mechanics.

Recent improvement in computer performance has made rapid progress in fluid simulations. As a result, fluid simulations have been applied not only to evaluation of aerodynamic characteristics of aircraft, automobiles, railroad vehicles, ships, etc., but also to analysis of blood flow states of hearts, blood vessels, etc.

When a fluid simulation is conducted, an analysis result is visualized so that the analysis result may easily be understood visually. One means of visualizing a result of a fluid simulation is displaying streaklines. A streakline is a curve formed by connecting fluid particles that have passed through a certain point in space. In a wind tunnel experiment, a trail of smoke ejected from a predetermined place is a streakline. Namely, by generating display information about a streakline in a fluid simulation and displaying the streakline, the motion of particles in fluid, as in a trail of smoke in a wind tunnel experiment, is visualized, without performing any wind tunnel experiment.

Various techniques relating to fluid simulations have been proposed. For example, there has been proposed a technique of performing a high-speed simulation and quickly and smoothly representing a scene in fluid in detail. There has also been proposed a technique of easily applying a result of a structure-fluid analysis simulation to diagnosis of vascular abnormality. There has also been proposed an apparatus that enables users such as doctors who are unfamiliar with computational fluid mechanics to conduct appropriate blood flow simulations. In addition, various papers relating to fluid simulations have been published. See, for example, the following literatures:

Japanese Laid-open Patent Publication No. 2003-6552
Japanese Laid-open Patent Publication No. 2015-97759
International Publication Pamphlet No. WO2016/056642
Tino Weinkauf and Holger Theisel, "Streak Lines as Tangent Curves of a Derived Vector Field", IEEE Transactions on Visualization and Computer Graphics, Volume: 16, Issue: 6, November-December 2010
Erwin Fehlberg, "LOW-ORDER CLASSICAL RUNGE-KUTTA FORMULAS WITH STEPSIZE CONTROL AND THEIR APPLICATION TO SOME HEAT TRANSFER PROBLEMS", NASA TECHNICAL REPORT, NASA TR R-315, July 1969
J. Donea, A. Huerta, J.-Ph. Ponthot and A. Rodriguez-Ferran, "Arbitrary Lagrangian-Eulerian methods", Encyclopedia of Computational Mechanics, John Wiley & Sons Ltd., November 2004, pp. 413-437
Seiryo Sugiura, Takumi Washio, Asuka Hatano, Junichi Okada, Hiroshi Watanabe, Toshiaki Hisada, "Multi-scale simulations of cardiac electrophysiology and mechanics using the University of Tokyo heart simulator", Progress in Biophysics and Molecular Biology, Volume 110, October-November 2012, Pages 380-389
William H. Press et al., "Numerical Recipes in C: The Art of Scientific Computing", Cambridge University Press, Oct. 30, 1992, pp. 113-117.
Joseph E. Flaherty, "Finite Element Analysis—Chapter 4 Finite Element Approximation", Apr. 1, 2005 (searched on Feb. 27, 2017), <URL:www.cs.rpi.edu/~flaherje/pdf/fea4.pdf>

However, these conventional streakline analysis techniques are based on the assumption that the structure in the analysis space does not deform, as in the case of analysis of the flow of air around an automobile, for example. When the structure deforms, it is difficult to track a streakline accurately.

SUMMARY

According to one aspect, there is provided a streakline visualization apparatus including: a memory configured to store fluid information including position information indicating positions of a plurality of grid points that move with accelerated motion in an analysis space as analysis time of a fluid simulation progresses, at each of a plurality of first time points having a first time interval and including velocity information indicating velocities of fluid on the plurality of grid points at each of the plurality of first time points; and a processor configured to perform a procedure including: calculating, based on the fluid information and by using an expression including a correction value for correcting an error attributable to the accelerated motion of the plurality of grid points represented by the position information, time differential values of the velocities of the fluid on the plurality of grid points at each of the plurality of first time points, calculating, based on the velocities and the time differential values of the velocities of the fluid on the plurality of grid points at each of the plurality of first time points, positions of a series of a plurality of particles sequentially outputted from a particle generation source as the analysis time progresses at each of a plurality of second time points having a second time interval shorter than the first time interval, and generating display information about a streakline indicating the series of the plurality of particles.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 6 illustrates an example of a group of elastic body information files;

FIG. 7 illustrates an example of a group of fluid information files;

FIG. 8 illustrates an example of a pre-analysis file;

FIG. 14 illustrates an example of a table of Runge-Kutta coefficients;

FIG. 15 illustrates data examples of streaklines;

FIG. 22 is a truth table indicating status variables;

DESCRIPTION OF EMBODIMENTS

Figure 1:
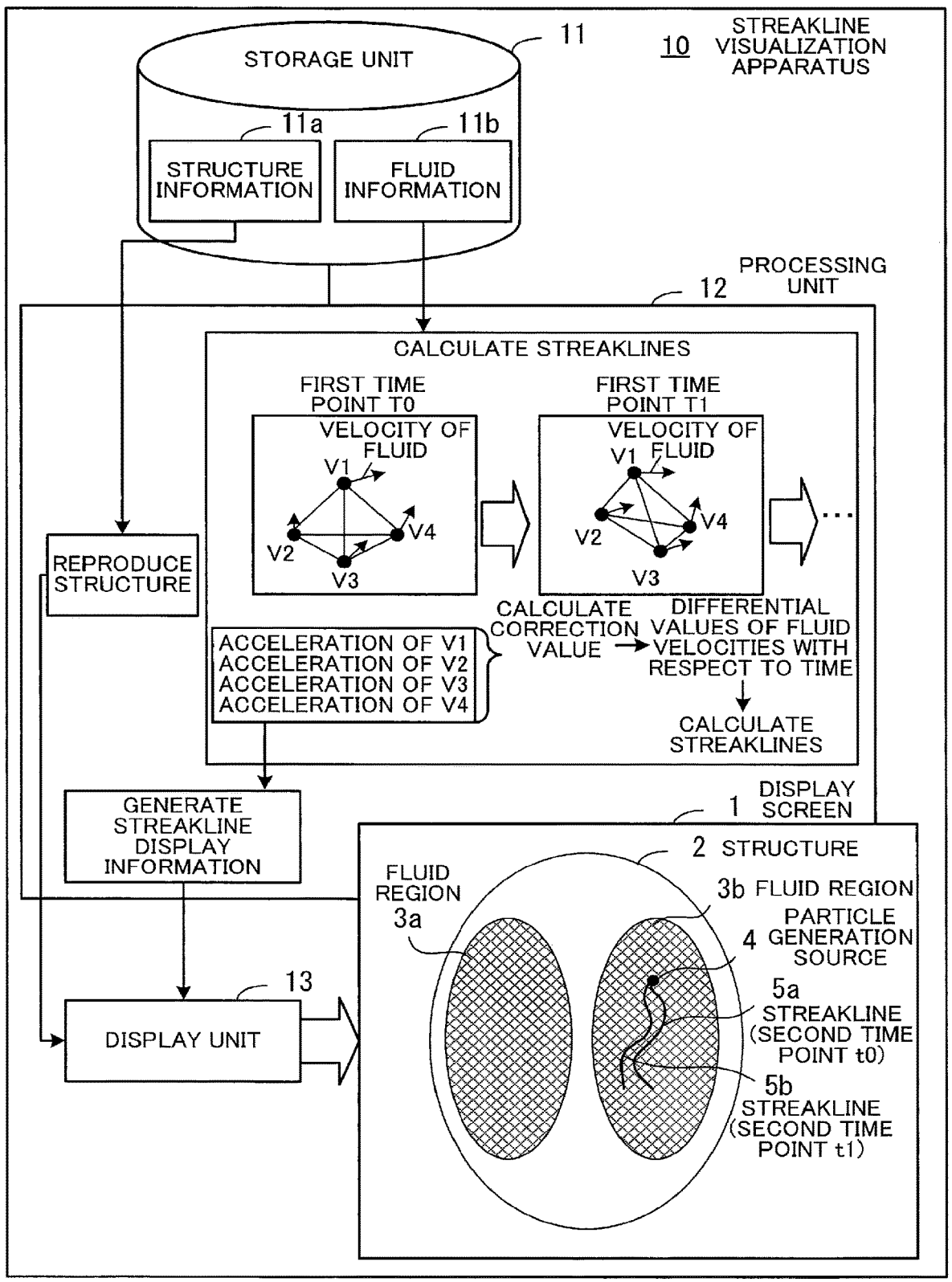
FIG. 1 illustrates an example of a streakline visualization apparatus according to a first embodiment.

Embodiments will be described below with reference to the accompanying drawings, wherein like reference characters refer to like elements throughout. Two or more of the embodiments may be combined with each other without causing inconsistency.

First Embodiment

First, a first embodiment will be described. The first embodiment provides a streakline display apparatus capable of tracking streaklines even when a structure deforms.

When a structure deforms, it is difficult to track streaklines accurately. One of the reasons is that, when a structure deforms, grid points are computationally in motion in relation to a moving boundary problem, and apparent force occurs consequently.

Coriolis force is a simple example of the apparent force. If an observer who remains stationary on the earth fires a cannonball, it looks to the observer as if force which is inexplicable by centrifugal force alone is bending the trajectory of the cannonball. This is because, when seen from the space, since the observer himself or herself is also in motion with the earth. Namely, the observer has acceleration, and this acceleration creates apparent force. Such force, which is not intrinsic force but is seen as if it acts due to the motion of an observer (a coordinate system and a way of handling the coordinate system) is called "apparent force".

Namely, when a structure deforms, the impact of the deformation of the structure needs to be reflected in the calculation of the motion of the fluid. In this operation, the motion of the fluid is calculated in association with the movement of an individual grid point defining the shape of the structure. If grid points move with accelerated motion, apparent force exists in the calculation of the motion of the fluid based on the grid points. Unless the motion of the fluid is calculated by reflecting this apparent force, streaklines are inaccurately calculated. For example, if the calculation accuracy of a velocity field representing a fluid velocity is low, an impossible behavior such as a streakline being embedded into the myocardium is exhibited, and the calculation fails.

Thus, in the first embodiment, by correcting the apparent force caused by the accelerated motion of an individual grid point, the velocity field of the fluid is accurately calculated. As a result, the behavior of the streaklines near the myocardium is accurately derived. As a result, the phenomenon in which a streakline is embedded into the myocardium is prevented. Consequently, since the calculation stability is improved and a streakline is not embedded into the myocardium, a calculation error is avoided.

FIG. 1 illustrates an example of a streakline visualization apparatus according to the first embodiment. This streakline visualization apparatus 10 includes a storage unit 11, a processing unit 12, and a display unit 13. For example, the storage unit 11 is a memory or a storage device of the streakline visualization apparatus 10. For example, the processing unit 12 is a processor or an arithmetic circuit of the streakline visualization apparatus 10. For example, the display unit 13 is a graphics circuit of the streakline visualization apparatus 10.

The storage unit 11 includes structure information 11a and fluid information 11b, for example. The structure information 11a indicates change of the shape of the structure in the fluid simulation analysis space over time. The fluid information 11b includes position information about grid points V1 to V4 and fluid velocity information on the grid points V1 to V4. For example, the position information indicates positions of the plurality of grid points V1 to V4 at each of a plurality of first time points (T0, T1, . . . ) having a first time interval. In addition, the velocity information indicates fluid velocities on the plurality of grid points V1 to V4 at each of the plurality of first time points (TO, T1, . . . ). The plurality of grid points move with accelerated motion in an analysis space as fluid simulation analysis time progresses. While FIG. 1 illustrates the four grid points V1 to V4, the analysis space includes many other grid points not illustrated. In addition, in FIG. 1, the fluid velocities at the individual grid points are indicated by arrows.

The processing unit 12 calculates streaklines 5a and 5b on the basis of the fluid information 11b. For example, by using an expression including a correction value for correcting an error attributable to the accelerated motion of the plurality of grid points represented by the position information, the processing unit 12 calculates time differential values of the velocities of the fluid on the plurality of grid points V1 to V4 at each of the plurality of first time points. Specifically, for example, the processing unit 12 calculates the velocity and acceleration on each of the plurality of grid points V1 to V4 at each of the plurality of first time points (T0, T1, . . . ) on the basis of the position information. Next, by using an expression including a calculated velocity and acceleration as variables, the processing unit 12 calculates time differential values of the velocities of the fluid on the plurality of grid points V1 to V4 at each of the plurality of first time points (T0, T1, . . . ). The following expressions (6) and (7) are examples of the expressions for calculating the velocity and the acceleration. In addition, the following expressions (4) and (5) are examples of the expression for calculating the time differential values of the velocity, the expression including the velocity and acceleration as variables.

Next, the processing unit 12 defines a plurality of particles sequentially outputted from a particle generation source 4 as the analysis time progresses. Next, on the basis of the velocities and the time differential values of the velocities of the fluid on the plurality of grid points V1 to V4 at each of the plurality of first time points (T0, T1, . . . ), the processing unit 12 calculates the positions of the plurality of particles at each of a plurality of second time points (t0, t1, . . . ). The plurality of second time points (t0, t1, . . . ) has a second time interval shorter than the first time interval. For example, the processing unit 12 generates interpolation curves, each of which smoothly connects points indicating the velocities at a corresponding one of the plurality of grid points V1 to V4 at each of the plurality of first time points (T1, T2, . . . ) and each of which represents change of the fluid velocities over time. When an interpolation curve passes through a point at a single first time point, the interpolation curve has a slope based on the time differential value of the fluid velocity at the first time point. Next, on the basis of the individual interpolation curves of the plurality of grid points V1 to V4, the processing unit 12 calculates the positions of the plurality of particles at each of the plurality of second time points. An example of these interpolation curves will be described with the following expression (20).

In addition, the processing unit 12 reproduces change of the shape of a structure 2 over time on the basis of the structure information 11a. The processing unit 12 generates display information about the streaklines 5a and 5b each indicating a series of the plurality of particles outputted from the particle generation source 4.

The display unit 13 displays the streaklines 5a and 5b on a display screen 1 on the basis of the display information generated by the processing unit 12. For example, the display unit 13 superimposes the streakline 5a or 5b within a fluid region 3a or 3b including the fluid on an image of the structure 2 on the display screen 1. In FIG. 1, the streakline 5a is a streakline at the second time point "t0", and the streakline 5b is a streakline at the second time point "t1".

In this way, the streakline visualization apparatus 10 calculates the positions of a plurality of particles accurately by reflecting the apparent force attributable to the accelerated motion of the individual grid points and displays accurate streaklines by generating display information about the accurate streaklines.

In addition, the processing unit 12 may be configured to determine whether the streakline 5a or 5b enters the structure and display the streakline 5a or 5b only when the streakline 5a or 5b does not enter the structure. In this case, for efficient processing, the processing unit 12 may be configured to perform the following processing when calculating a second streakline at a second analysis time on the basis of a first streakline at a first analysis time point.

For example, the processing unit 12 sets a partial region including a discrete point at a first position on the first streakline in the analysis space as an analysis target region of the discrete point. The analysis target region is a spherical region, for example. Next, the processing unit 12 calculates, based on the velocities of the fluid in the analysis target region, the velocity indicated by the fluid information, a second position indicating a destination of a particle on the discrete point at the second analysis time point. Next, the processing unit 12 determines, based on information about the structure in the analysis target region, the information indicated by the structure information, a region occupied by the structure in the analysis target region at the second analysis time point. Next, the processing unit 12 determines entrance or non-entrance of the second streakline into the occupied region based on the first position and the second position. When determining that the second streakline does not enter the occupied region, the processing unit 12 generates display information about the second streakline passing through the second position and displays the second streakline.

In this way, by limiting the analysis range to an analysis target region and determining whether a streakline has entered an occupied region of the structure, the throughput is reduced, and efficient processing is performed.

Second Embodiment

Next, a second embodiment will be described. The second embodiment provides a visualization apparatus capable of visualizing streaklines of the blood flow in a heart along with the motion of the heart.

For example, use of computational fluid analysis makes it possible to simulate the behavior of fluid, even fluid in a system in which measurement is technically or ethically difficult, such as transfer of the blood flow in a heart. Thus, computational fluid analysis is used to discuss treatments of congenital heart disease, etc. in which transfer of the blood flow in a heart malfunctions. Namely, computational fluid analysis is an important technique. By using a visualization apparatus to visualize results of such computational fluid analysis, health-care professionals such as doctors are able to easily understand the analysis results and make treatment plans.

Figure 2:
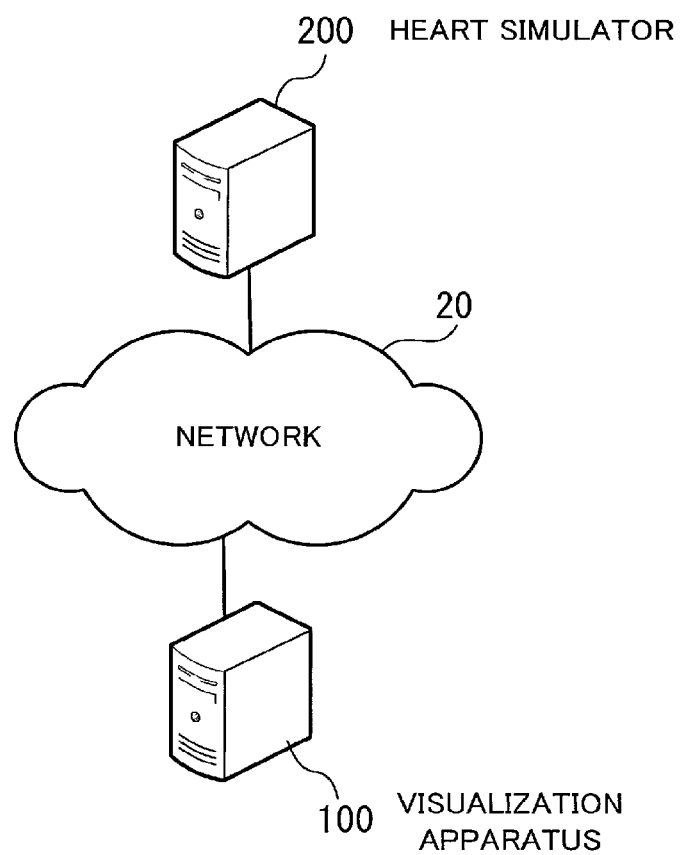
FIG. 2 illustrates a system configuration example according to a second embodiment.

FIG. 2 illustrates a system configuration example according to the second embodiment. A visualization apparatus 100 is connected to a heart simulator 200 via a network 20. The heart simulator 200 is a computer that performs a simulation of the myocardial motion and coronary circulation. The visualization apparatus 100 acquires a simulation result from the heart simulator 200. Next, the visualization apparatus 100 generates display information about streaklines based on the simulation result and displays the generated streaklines. For example, the simulation result includes information about a three-dimensional (3D) model indicating a heart shape, the velocity of blood in a blood vessel, and a physical property value of myocardium or blood per time point.

Figure 3:
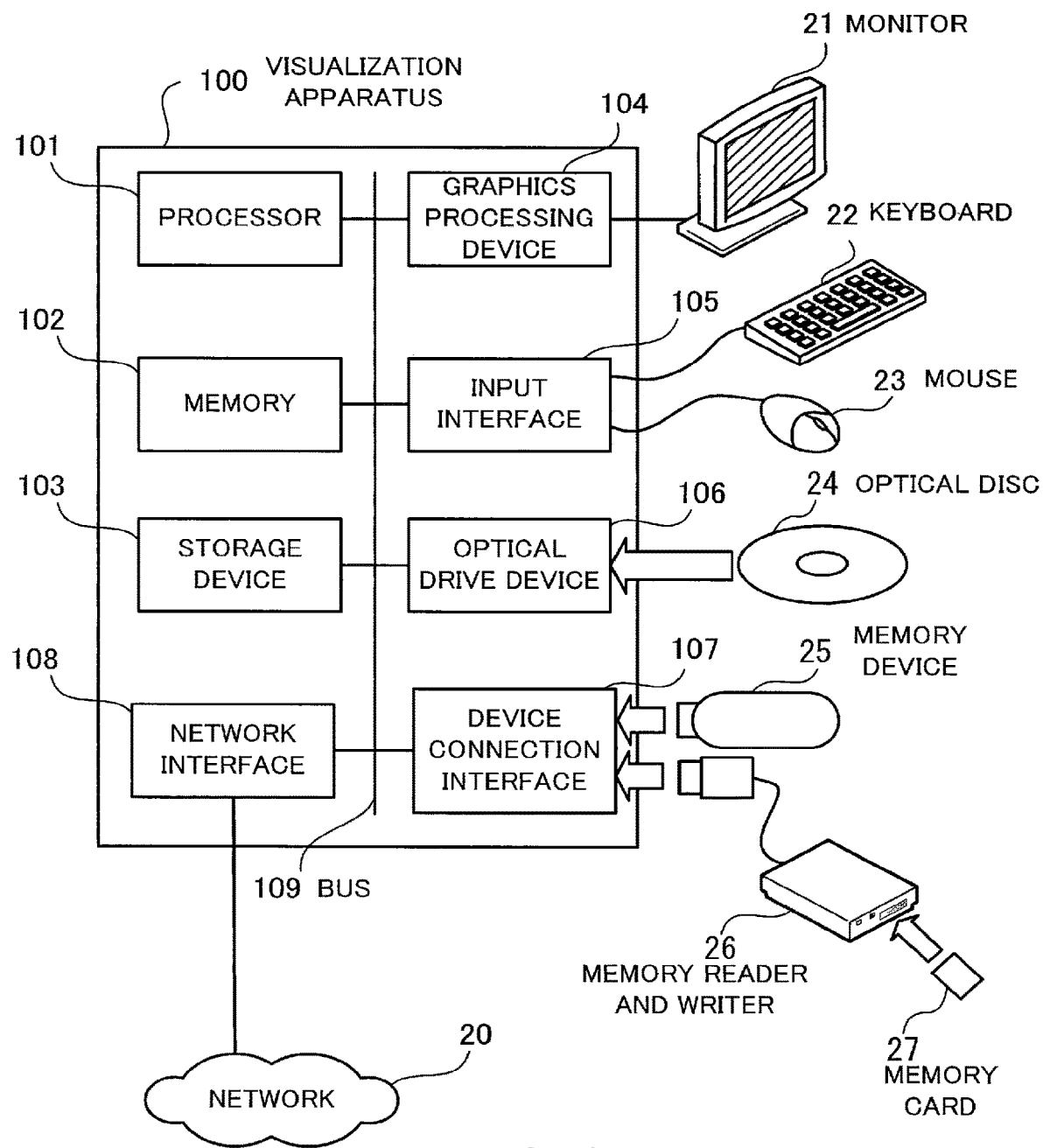
FIG. 3 illustrates a hardware configuration example of a visualization apparatus.

FIG. 3 illustrates a hardware configuration example of the visualization apparatus 100. The visualization apparatus 100 is comprehensively controlled by a processor 101. The processor 101 is connected to a memory 102 and a plurality of peripheral devices via a bus 109. The processor 101 may be a multiprocessor. The processor 101 is an arithmetic processing device such as a central processing unit (CPU), a micro processing unit (MPU), or a digital signal processor (DSP). At least a part of the functions realized by causing the processor 101 to perform a program may be realized by using an electronic circuit such as an application specific integrated circuit (ASIC) or a programmable logic device (PLD).

The memory 102 is used as a main storage device of the visualization apparatus 100. The memory 102 temporarily stores at least a part of an operating system (OS) program or an application program executed by the processor 101. In addition, the memory 102 stores various kinds of data needed for processing performed by the processor 101. For example, a volatile semiconductor storage device such as a random access memory (RAM) is used as the memory 102.

Examples of the peripheral devices connected to the bus 109 include a storage device 103, a graphics processing device 104, an input interface 105, an optical drive device 106, a device connection interface 107, and a network interface 108.

The storage device 103 electrically or magnetically writes and reads data on its storage medium. The storage device 103 is used as an auxiliary storage device of the visualization apparatus 100. The storage device 103 stores an OS program, an application program, and various kinds of data. For example, a hard disk drive (HDD) or a solid state drive (SSD) may be used as the storage device 103.

The graphics processing device 104 is connected to a monitor 21. The graphics processing device 104 displays an image on a screen of the monitor 21 in accordance with an instruction from the processor 101. Examples of the monitor 21 include a cathode ray tube (CRT) display device and a liquid crystal display (LCD) device.

The input interface 105 is connected to a keyboard 22 and a mouse 23. The input interface 105 transmits a signal transmitted from the keyboard 22 or the mouse 23 to the processor 101. The mouse 23 is a pointing device. A different pointing device such as a touch panel, a tablet, a touchpad, or a trackball may also be used.

The optical drive device 106 reads data stored on an optical disc 24 by using laser light or the like. The optical disc 24 is a portable storage medium storing data that is read by light reflection. Examples of the optical disc 24 include a digital versatile disc (DVD), a DVD-RAM, a compact disc read only memory (CD-ROM), and a CD-Recordable (R)/ReWritable (RW).

The device connection interface 107 is a communication interface for connecting peripheral devices to the visualization apparatus 100. For example, a memory device 25 or a memory reader and writer 26 may be connected to the device connection interface 107. The memory device 25 is a storage medium capable of communicating with the device connection interface 107. The memory reader and writer 26 is capable of reading and writing data on a memory card 27. The memory card 27 is a card-type storage medium.

The network interface 108 is connected to the network 20. The network interface 108 exchanges data with other computers or communication devices via the network 20.

The processing functions according to the second embodiment may be realized by the above hardware configuration. The apparatus described in the first embodiment may also be realized by a hardware configuration equivalent to that of the visualization apparatus 100 illustrated in FIG. 3.

The visualization apparatus 100 realizes the processing functions according to the second embodiment by executing a program stored in a computer-readable storage medium, for example. The program holding the processing contents executed by the visualization apparatus 100 may be stored in any one of various kinds of storage media. For example, the program executed by the visualization apparatus 100 may be stored in the storage device 103. The processor 101 loads at least a part of the program in the storage device 103 onto the memory 102 and executes the loaded program. The program executed by the visualization apparatus 100 may be stored in a portable storage medium such as the optical disc 24, the memory device 25, or the memory card 27. For example, after the program stored in the portable storage medium is installed by the processor 101 in the storage device 103, the program is executed by the processor 101. The processor 101 may directly read the program from the portable storage medium and execute the read program.

Next, streaklines will be described.

Figure 4:
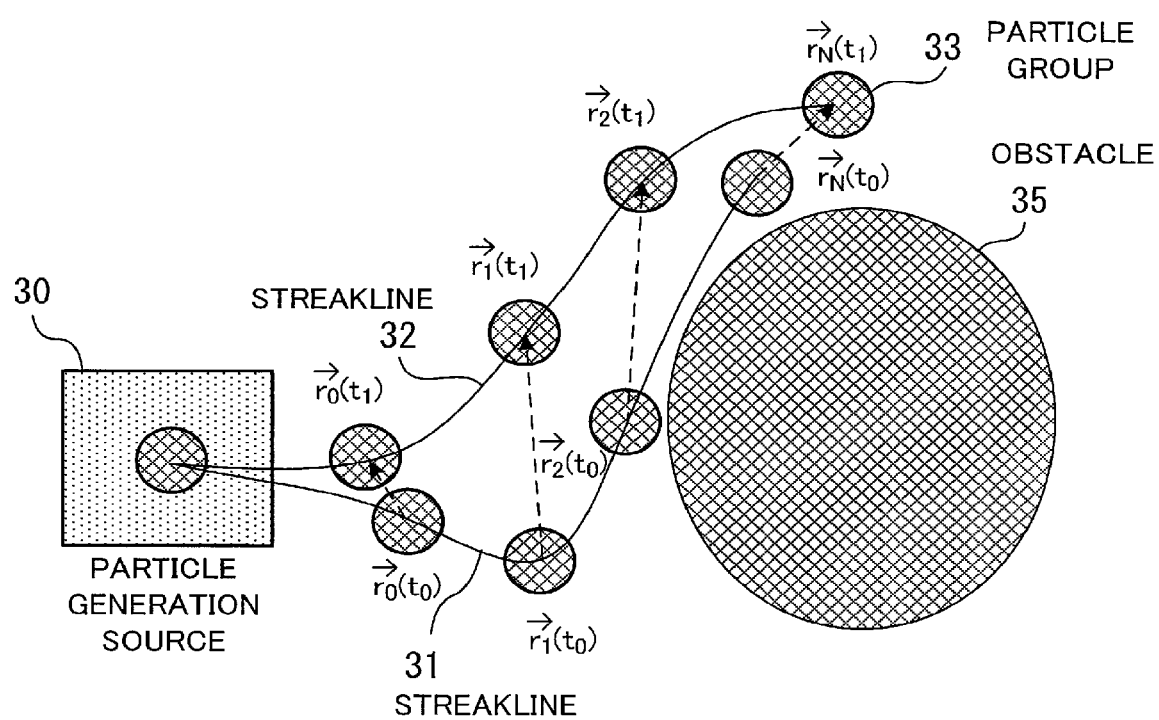
FIG. 4 illustrates a streakline calculation example.

FIG. 4 illustrates a streakline calculation example. The visualization apparatus 100 defines a particle generation source 30 in an analysis target space. When analysis is started, particle groups 33 are continuously emitted from the particle generation source 30. When the flow field does not change over time, the particle groups 33 form a fixed curve (a streamline). However, when the flow field changes over time, the curve formed by the particle groups 33 changes momentarily. Streaklines 31 and 32 are such curves that are formed when the flow field changes over time. In FIG. 4, the streakline 31 represents a series of particle groups 33 at the time point $t_0$, and the streakline 32 represents the series of particle groups 33 at the time point $t_1$. Since there is an obstacle 35, these streaklines 31 and 32 become very curvy.

These streaklines 31 and 32 are useful to visualize how the particle groups 33 are transferred in the time-varying flow field. For example, a case in which the obstacle 35 is an automobile will be described. To visualize the air resistance of a developed automobile, the particle generation source 30 is arranged in front of the automobile, and air is supplied toward the automobile from a fan or the like arranged where the particle generation source 30 is arranged.

In addition, in a fluid simulation in the visualization apparatus 100, particle groups 33 are continuously emitted, and trajectories of the particle groups 33 are measured as the streaklines 31 and 32. The streaklines 31 and 32 directly describe and visualize transfer of the fluid. Thus, streaklines are applicable to various fields.

A lot of research has been done on calculation and visualization of streaklines. In addition, a lot of research directed to turbulent flow, unstable flow, etc. has also been done. However, not much research has previously been done on visualization of streaklines in a simulation where an elastic body such as a heart, which is deemed as a wall surface by fluid, undergoes large deformation. Since hearts periodically pulsate and repeatedly expand and contract, they are a typical example of a system that undergoes large deformation. In addition, since this periodic motion plays an important role in the pumping action of the heart, evaluating transfer of the blood flow in the system in which the elastic body periodically undergoes large deformation is important in considering treatments of heart disease.

In the field of biological simulations, heart behaviors have been simulated on computers. Through a simulation on a computer, effectiveness of treatment obtained by an operation is evaluated without actually performing the operation. Thus, use of biological simulations enables doctors to consider the best treatment plans before actually performing an operation. In particular, a heart simulation is directed to a heart having a complex 3D structure, and the behavior of the heart dynamically changes. If streaklines representing transfer of the blood flow in the heart are visualized in coordination with the behavior of the heart, doctors may easily understand the state of the heart visually. Displaying the state of the heart visually easily is effective in preventing errors in judgement.

The following points are obstacles to be overcome to visualize streaklines in the blood flow in a heart.

1. When the myocardium (elastic body) largely deforms, it is difficult to accurately track the behaviors of pathlines and streaklines around the myocardium.

2. In the case of a pathline, calculation needs to be performed only at a single point. However, in the case of a streakline, calculation needs to be performed at all the N points that form the line, resulting in a significantly large amount of calculation.

3. Some low-quality meshes of a finite element model increase the overall calculation amount.

Thus, by using the following functions, the visualization apparatus 100 according to the second embodiment visualizes accurate streaklines with a feasible calculation amount.

1-1: The visualization apparatus 100 accurately determines whether an individual point on a streakline has entered the myocardium outside the moving region or has fallen outside the simulation target system.

1-2: When the visualization apparatus 100 determines that a point on a streakline has fallen outside the moving region, the visualization apparatus 100 adjusts the time step, which is, a parameter in a differential equation for the streamline, to prevent the point from falling outside the moving region.

1-3: To estimate information about a field at any time point, the visualization apparatus 100 interpolates the field by using an interpolation method.

1-4: To improve the accuracy of the motion of a streakline, the visualization apparatus 100 calculates the streakline by using an expression in which apparent force is reflected.

2-1: Since application of the function in 1-3 increases the calculation amount, the visualization apparatus 100 calculates the maximum distance that a point on a streakline moves and calculates only the information about the field inside a predicted sphere having a radius equal to the maximum distance. In this way, the visualization apparatus 100 maintains a certain calculation amount regardless of the data capacity.

2-2: By dividing the time step, the visualization apparatus 100 decreases the radius of the predicted sphere, needs a calculation amount less than that needed when no predicted sphere is used, and improves the accuracy at the same time.

3-1: Since most of the calculation is performed on high-quality meshes, the visualization apparatus 100 performs speculative calculation by assuming that all the meshes are high-quality meshes. In a case where the calculation fails, the visualization apparatus 100 performs accurate calculation. In this way, the calculation amount is reduced. In this speculative calculation, by allowing the possibility that the destination of a point on a streakline falls outside the predicted sphere, the visualization apparatus 100 decreases the radius of the predicted sphere. The case where the calculation fails is a case where the destination of a point on a streakline does not exist within the predicted sphere.

3-2: Since the visualization apparatus 100 performs speculative calculation in 3-1, the visualization apparatus 100 prepares a probability model and determines a parameter set that achieves the minimum calculation amount including a penalty needed when the calculation fails.

4-1: To efficiently perform the streakline calculation in which apparent force is reflected, coefficients based on the apparent force are previously calculated, and a streakline is calculated by referring to the calculation result per time step.

The following advantageous effects are obtained by implementing these functions on the visualization apparatus 100.

1. Even when the myocardium (elastic body) largely deforms, the visualization apparatus 100 is able to calculate streaklines while taking the motion of the myocardium (elastic body) into consideration.

2. The visualization apparatus 100 is able to calculate an individual point on a streakline quickly and accurately by using a predicted sphere and an expression in which the apparent force is reflected.

3. The visualization apparatus 100 is able to set the radius of the predicted sphere that minimizes the calculation cost by using a probability model.

Hereinafter, functions of the visualization apparatus 100 will be described in detail.

Figure 5:
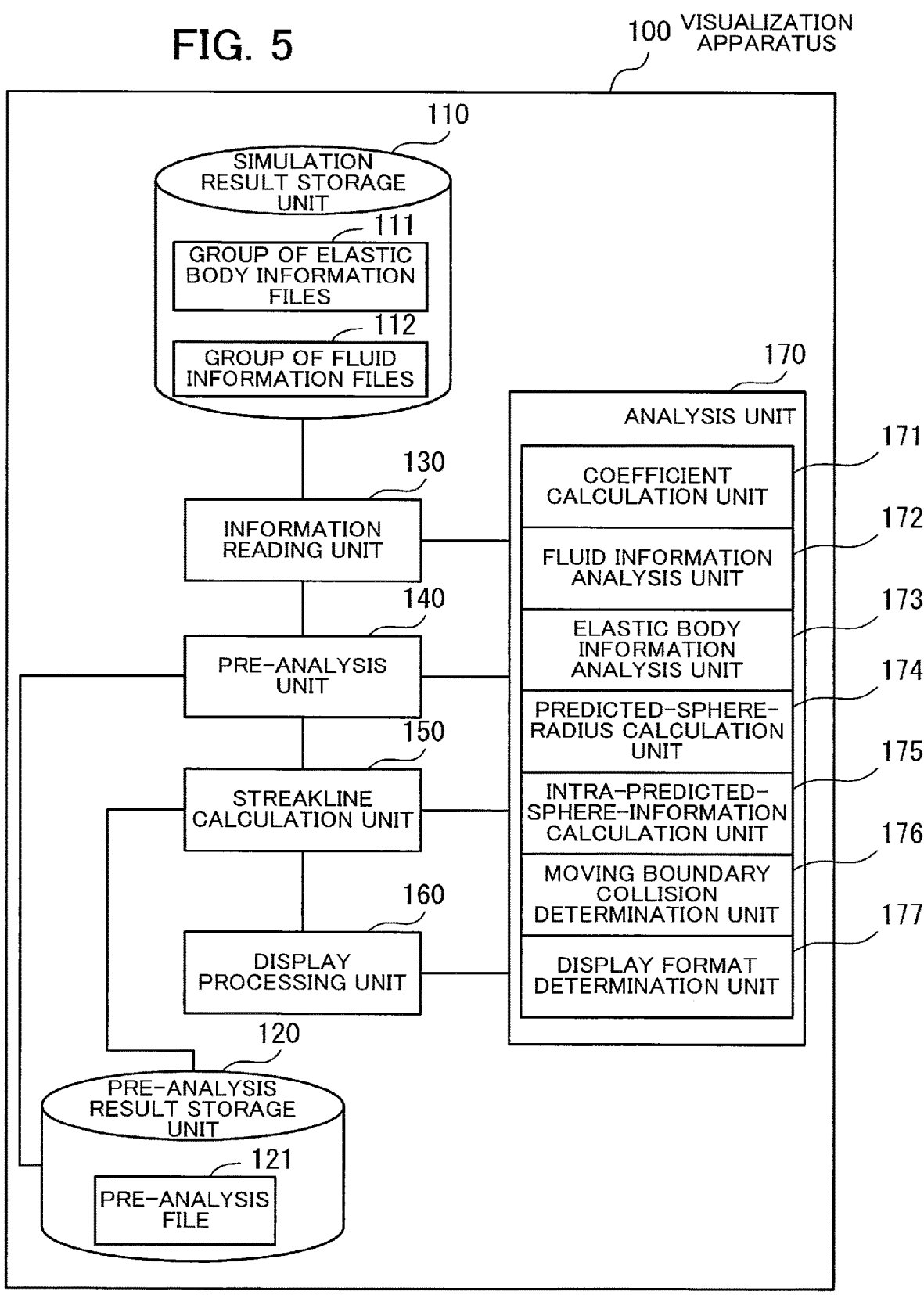
FIG. 5 is a block diagram illustrating functions of the visualization apparatus.

FIG. 5 is a block diagram illustrating functions of the visualization apparatus 100. The visualization apparatus 100 includes a simulation result storage unit 110 and a pre-analysis result storage unit 120 as information storage functions. The simulation result storage unit 110 stores simulation results acquired from the heart simulator 200. For example, when the heart simulator 200 performs a computational fluid dynamics simulation, simulation results about the dynamically-changing elastic body and fluid fields at L time points $t_0, t_1, \ldots, t_L$ (L is an integer of 1 or more) are stored in files. For example, information about the myocardium and information about the blood flow are stored as separate files in the simulation result storage unit 110. In the example in FIG. 5, information about the myocardium per time point is stored as a group of elastic body information files 111, and information about the blood flow per time point is stored as a group of fluid information files 112.

The pre-analysis result storage unit 120 stores apparent-force-based coefficients calculated by pre-analysis of apparent force. Hereinafter, a group of coefficients calculated by the pre-analysis will be referred to as a pre-analysis result Q.

For example, the pre-analysis result storage unit 120 stores a pre-analysis file 121 including the pre-analysis result Q.

By analyzing these simulation results stored in the simulation result storage unit 110, the visualization apparatus 100 calculates streaklines that describe information about the transfer of the blood flow. A time interval $\Delta t_i = t_{i+1} - t_i$ outputted as a simulation result does not need to match the time interval used when the heart simulator 200 solves a differential equation. To reduce the information amount, it is common to output only some of the simulation results. Thus, to accurately obtain streaklines, the visualization apparatus 100 uses an interpolation method or the like and estimates various physical quantities at target time points by using output files at a plurality of time points.

Next, processing functions of the visualization apparatus 100 will be described. The visualization apparatus 100 includes an information reading unit 130, a pre-analysis unit 140, a streakline calculation unit 150, a display processing unit 160, and an analysis unit 170.

The information reading unit 130 reads files indicating fluid analysis results from the simulation result storage unit 110. The pre-analysis unit 140 calculates coefficients for calculation of streaklines by using the information ready by the information reading unit 130. The pre-analysis unit 140 stores the pre-analysis file 121 including the pre-analysis result Q in the pre-analysis result storage unit 120. The streakline calculation unit 150 calculates streaklines by using the information read by the information reading unit 130 and the coefficients calculated by the pre-analysis unit 140. The display processing unit 160 visualizes the obtained result.

The analysis unit 170 is a group of functions commonly used by the information reading unit 130, the pre-analysis unit 140, the streakline calculation unit 150, and the display processing unit 160. When performing specific analysis processing, the information reading unit 130, the pre-analysis unit 140, the streakline calculation unit 150, and the display processing unit 160 request the analysis unit 170 to perform processing and obtain results.

The analysis unit 170 includes a coefficient calculation unit 171, a fluid information analysis unit 172, an elastic body information analysis unit 173, a predicted-sphere-radius calculation unit 174, an intra-predicted-sphere-information calculation unit 175, a moving boundary collision determination unit 176, and a display format determination unit 177. The coefficient calculation unit 171 calculates coefficients included in an interpolating polynomial in which apparent force is reflected. The fluid information analysis unit 172 analyzes the velocity field of the fluid, the positions of the discrete points, and the boundary surfaces. The elastic body information analysis unit 173 analyzes the positions of the discrete points of an elastic body such as the myocardium, which is not the fluid, and the boundary surfaces. The predicted-sphere-radius calculation unit 174 sets the radius of the predicted sphere used to improve the calculation speed and the calculation accuracy when streaklines are calculated. The intra-predicted-sphere-information calculation unit 175 calculates the velocity field and the myocardial position inside the predicted sphere, for example. The moving boundary collision determination unit 176 determines whether a point on a streakline has entered the myocardium as a result of a calculation error. The display format determination unit 177 determines how the obtained streaklines are displayed.

For example, the function of an individual element illustrated in FIG. 5 may be realized by causing a computer to perform a program module corresponding to the corresponding element.

Next, information obtained as simulation results will be described in detail.

FIG. 6 illustrates an example of the group of elastic body information files 111. The group of elastic body information files 111 is a group of elastic body information files 111a, 111b, and so on per simulation time point. Each of the elastic body information files 111a, 111b, and so on is given a file name such as "stru(X).inp". In this case, the "X" in an individual file name represents a number, and these numbers are given in ascending order in accordance with the chronological order of the simulation time points.

The elastic body information files 111a, 111b, and so on include myocardial data indicating the shape of the heart at the respective time points. The myocardial data includes coordinate values along the x, y, and z axes of an individual grid (vertexes arranged in 3D space), an individual grid ID indicating four vertexes of a tetrahedral element (TETRA) included in the myocardium, and force applied to an individual element.

FIG. 7 illustrates an example of the group of fluid information files 112. The group of fluid information files 112 is a group of fluid information files 112a, 112b, and so on per simulation time point. For example, each of the fluid information files 112a, 112b, and so on is given a file name such as "flui(Y).inp". In this case, the "Y" in an individual file name represents a number, and these numbers are given in ascending order in accordance with the chronological order of the simulation time points.

The fluid information files 112a, 112b, and so on include blood flow data indicating the blood flow at the respective time points. The blood flow data includes coordinate values along the x, y, and z axes of an individual grid (vertexes arranged in 3D space), an individual grid ID indicating four vertexes of a tetrahedral element (TETRA) included in a blood vessel, and an individual velocity field vector indicating the direction and velocity of blood flowing on an individual grid.

FIG. 8 illustrates an example of a pre-analysis file. In the pre-analysis file 121, grid numbers, time points, position coordinates, velocity fields (blood flow only), and interpolating polynomial coefficients are recorded so that at an interpolating polynomial (the following expression (2)) is reproducible at an individual time point and an individual grid point. For example, the pre-analysis file 121 includes an output time point index table 121a, a myocardium-side interpolating polynomial coefficient table 121b, and a fluid-side interpolating polynomial coefficient table 121c.

In the output time point index table 121a, a time point (Time) on a fluid analysis simulation is associated with a time point index (Time Index).

In the myocardium-side interpolating polynomial coefficient table 121b, the position in the axis direction (Position) and the coefficients (coefficients a to d) used in a myocardium-side interpolating polynomial are set in association with a set of a grid ID (GRID ID), a time point index (Time Index), and an axis index (Direction Index).

In the fluid-side interpolating polynomial coefficient table 121c, the position in the axis direction (Position), the velocity in the axis direction (Velocity), and the coefficients (coefficients a to d) used in a fluid-side interpolating polynomial are set in association with a set of a grid ID (GRID ID), a time point index (Time Index), and an axis index (Direction Index).

The fluid-side interpolating polynomial coefficient table 121c may include a calculation result of time differentiation of the velocity field of the fluid at an individual.

The visualization apparatus 100 calculates and visualizes streaklines on the basis of the simulation results illustrated in FIGS. 6 and 7 and the pre-analysis result Q illustrated in FIG. 8. Hereinafter, streakline visualization processing will be described in detail.

Figure 9:
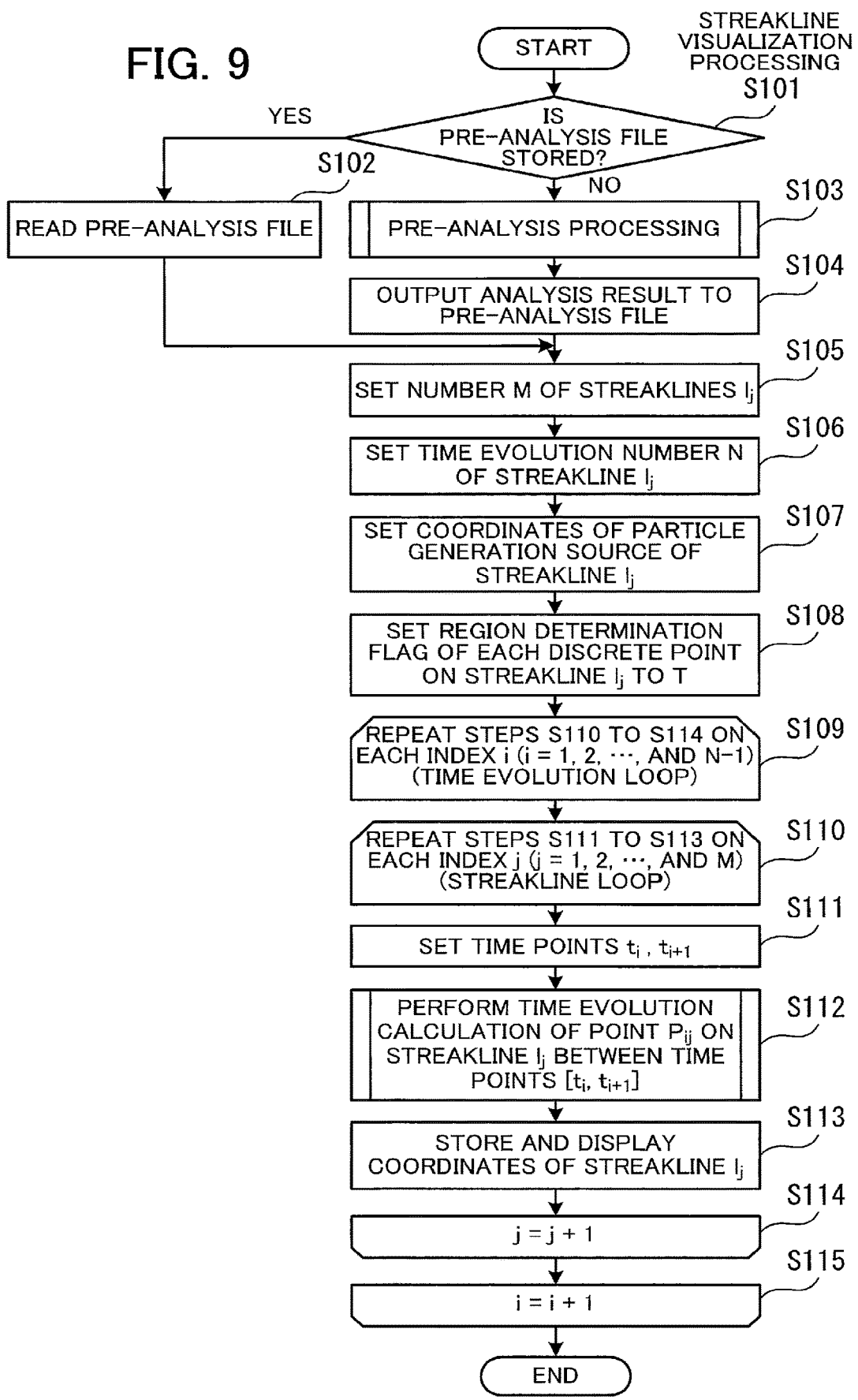
FIG. 9 is a flowchart illustrating an example of a procedure of streakline visualization processing.

FIG. 9 is a flowchart illustrating an example of a procedure of streakline visualization processing. Hereinafter, the processing illustrated in FIG. 9 will be described step by step.

[Step S101] The streakline calculation unit 150 determines whether the pre-analysis file 121 is stored in the pre-analysis result storage unit 120. If the streakline calculation unit 150 determines that the pre-analysis file 121 is stored, the processing proceeds to step S102. If not, the processing proceeds to step S103.

[Step S102] The streakline calculation unit 150 reads the pre-analysis file 121 from the pre-analysis result storage unit 120. Next, the processing proceeds to step S105.

[Step S103] The pre-analysis unit 140 performs pre-analysis processing for calculating interpolating polynomial coefficients. The pre-analysis processing will be described in detail below with reference to FIG. 10.

[Step S104] The pre-analysis unit 140 generates a pre-analysis file 121 including the coefficients calculated in the pre-analysis processing and stores the pre-analysis file 121 in the pre-analysis result storage unit 120.

Next, in steps S105 to S108, the streakline calculation unit 150 performs initial settings of an individual streakline.

[Step S105] The streakline calculation unit 150 sets the number M of streaklines to be calculated (M is an integer of 1 or more). For example, the streakline calculation unit 150 sets a value inputted by the user as the number M of streaklines.

[Step S106] The streakline calculation unit 150 sets the number N of streakline calculations (N is an integer of 1 or more). Hereinafter, the number N of streakline calculations will be referred to as "time evolution number". For example, the streakline calculation unit 150 sets a value inputted by the user as the time evolution number N.

Since streaklines change over time, a series of time points $t_0, t_1, \ldots$, and $t_N$, at which results of streaklines are outputted, are determined by setting the time evolution number N. When the specified time evolution number N is larger than the number L of files (L is an integer of 1 or more), the streakline calculation unit 150 may treat the (L+1)th file as a beat in the second cardiac cycle and uses the file at the time point $t_0$ for the (L+1)th file. For example, the time interval in the series of time points is set to be 0.01 second. However, alternatively, the series of time points may have irregular time intervals.

[Step S107] The streakline calculation unit 150 sets coordinates of a particle generation source of a streakline. For example, the streakline calculation unit 150 sets a point specified by the user in the analysis space as the coordinates of a particle generation source. For example, the user specifies a point in the space while referring to the myocardial information and the blood flow information. The streakline calculation unit 150 reads the coordinates of the specified point as a coordinate vector $X_0$. When the number of streaklines is 1, the particle generation source of the streakline is set to have the coordinate vector $X_0$. When the number of streaklines is a plural number, the streakline calculation unit 150 randomly sets a particle generation source of a streakline in a sphere having the coordinate vector $X_0$ as its center and having a radius r (r is a positive real number). The particle generation source of a streakline is selected from the coordinates in the blood flow. The streakline calculation unit 150 sets a coordinate vector $X_j$ of the set particle generation source as the particle generation source of the streakline.

Next, the streakline calculation unit 150 performs initial settings of the jth (j=1, 2, . . . , M) streakline $l_j$ as follows.

The jth streakline $l_j$ is formed by discrete points matching the time evolution number N. Thus, the streakline calculation unit 150 generates points $P_{ij}$ (i=0, 1, 2, . . . , N) indicating the discrete points included in the streakline $l_j$. The streakline calculation unit 150 sets coordinates of initial values of individual discrete points as coordinates of a particle generation source.

When a streakline $l_j$ at the time point $t=t_i$ is calculated, an individual point $P_{ij}$ (i=0, 1, 2, . . . , i) is subjected to time evolution calculation as the position of a streakline particle emitted from the corresponding generation source. Since no streakline particles corresponding to the point $P_{ij}$ (i=i+1, . . . , N) have been emitted from any generation sources, these streakline particles are not subjected to the calculation when the streakline $l_j$ at the time point $t=t_i$ is calculated. In addition, the streakline calculation unit 150 calculates the discrete points in ascending order of the value i. Thus, a discrete point calculated earlier has a longer time since the emission from the corresponding particle generation source.

[Step S108] The streakline calculation unit 150 performs settings for a case in which a point on a streakline $l_j$ has fallen in a large artery or the like, namely, outside a fluid boundary in the target system. The point $P_{ij}$ on a streakline $l_j$ could fall in a large artery or the like, namely, outside the system through a fluid boundary. In such cases, since no fluid velocity field is defined outside the system, the calculation of the point $P_{ij}$ at the next time point fails to be performed. Thus, the streakline calculation unit 150 sets a region determination flag to each point $P_{ij}$ as a parameter of the individual discrete point. When the point $P_{ij}$ has fallen within the target region, the region determination flag indicates "T". In contrast, when the point $P_{ij}$ has drifted by the flow of fluid in a large artery or the like and fallen outside the target region, the region determination flag indicates "F". Since the fluid includes all the points $P_{ij}$ in the initial settings, the streakline calculation unit 150 sets the region determination flag of each discrete point to "T".

[Step S109] The streakline calculation unit 150 repeats a group of steps S110 to S114 on each of the indexes i (i=1, 2, . . . , and N−1) in ascending order from index i=1.

[Step S110] The streakline calculation unit 150 repeats a group of steps S111 to S113 on each of the indexes j (j=1, 2, . . . , and M) in ascending order from index j=1.

[Step S111] The streakline calculation unit 150 sets a time point as the start of the time evolution and stores the time point in the memory 102. In the i-th calculation, the calculation start time point is set as $t=t_i$. The time evolution end time point is set as $t=t_{i+1}$.

[Step S112] The streakline calculation unit 150 performs time evolution calculation between the time points defined by $t_i \le t \le t_{i+1}$. Based on the time evolution calculation, all the points $P_{ij}$ (i=0, 1, 2, . . . , and i) emitted from the particle generation source of the streakline $l_j$ at each time point $t=t_i$ are subjected to time evolution, and all the points on the line are updated momentarily. As a result of the time evolution calculation of the individual points $P_{ij}$ on the streakline $l_j$ at the time point $[t_i, t_{i+l}]$, coordinate values are acquired, which are set as the coordinates $P_{i+1,j}$ at the next time point $t=t_{i+1}$.

[Step S113] The streakline calculation unit 150 stores the acquired calculation results in a memory. Based on the calculation results, the display processing unit 160 visualizes the streakline $l_j$. In addition, the streakline calculation unit 150 is capable of outputting the coordinate values of the streakline $l_j$ to a file.

[Step S114] Each time the streakline calculation unit 150 performs the group of steps S111 to S113, the streakline calculation unit 150 adds 1 to the index j. After performing steps S111 to S113 on the index j=M, the streakline calculation unit 150 performs step S115.

[Step S115] Each time the streakline calculation unit 150 performs the group of steps S110 to S114, the streakline calculation unit 150 adds 1 to the index i. After performing steps S110 to S114 on the index i=N−1, the streakline calculation unit 150 ends the streakline visualization processing.

Next, the pre-analysis processing (step S103) will be described in detail. The pre-analysis processing is processing for generating coefficients used to estimate the structure information about the myocardium and the velocity field of the blood flow portion at any time point t.

First, output data as a premise will be described. The output data is given a simulation time point $t=t_i$. Hereinafter, the structure information about the myocardium will be denoted as a vector M (vector r, $t_i$). On the myocardium, a finite number of discrete point vectors $r_k$ is given. These items of information have been outputted to elastic body information files 111a, 111b, etc. about the myocardium as illustrated in FIG. 6. The discrete points are uniquely identified by the respective GRID IDs, and the corresponding coordinates are stored. An individual coordinate value per axis is an element of an individual discrete point vector $r_k$ indicating a discrete point corresponding to a GRID ID.

In a finite element method, calculation is performed by using, as elements, figures (for example, tetrahedral figures) each having these discrete points as vertexes. Each of the elements is uniquely identified by a TETRA ID in the elastic body information file 111a, 111b, etc. in FIG. 6, and a GRID ID of a discrete point constituting an element is stored. While tetrahedral elements are used in the example in FIG. 6, the elements may have a different figure other than a tetrahedral figure. The shape of the myocardium is determined by the positions of the discrete points and the arrangement of the infinite elements.

The structure information about the fluid portion is also determined in the same way as the myocardium. The structure information about the fluid portion will be denoted as a vector B (vector r, $t_i$). The fluid portion is also formed by a finite number of discrete points and finite elements, and these items of information have been outputted to the fluid information files 112a, 112b, etc. as illustrated in FIG. 7. The difference between the fluid and the myocardium is that velocity field information (velocity vector v (vector $r_k$, $t_i$)) indicating the fluid velocity field on the individual discrete grid point (vector $r_k$) has also been outputted as the fluid information. The pre-analysis unit 140 performs the pre-analysis processing by using the structure of the myocardium, the structure of the blood flow, and the velocity field information at all the time points $t_0, t_1, \ldots, t_L$.

Figure 10:
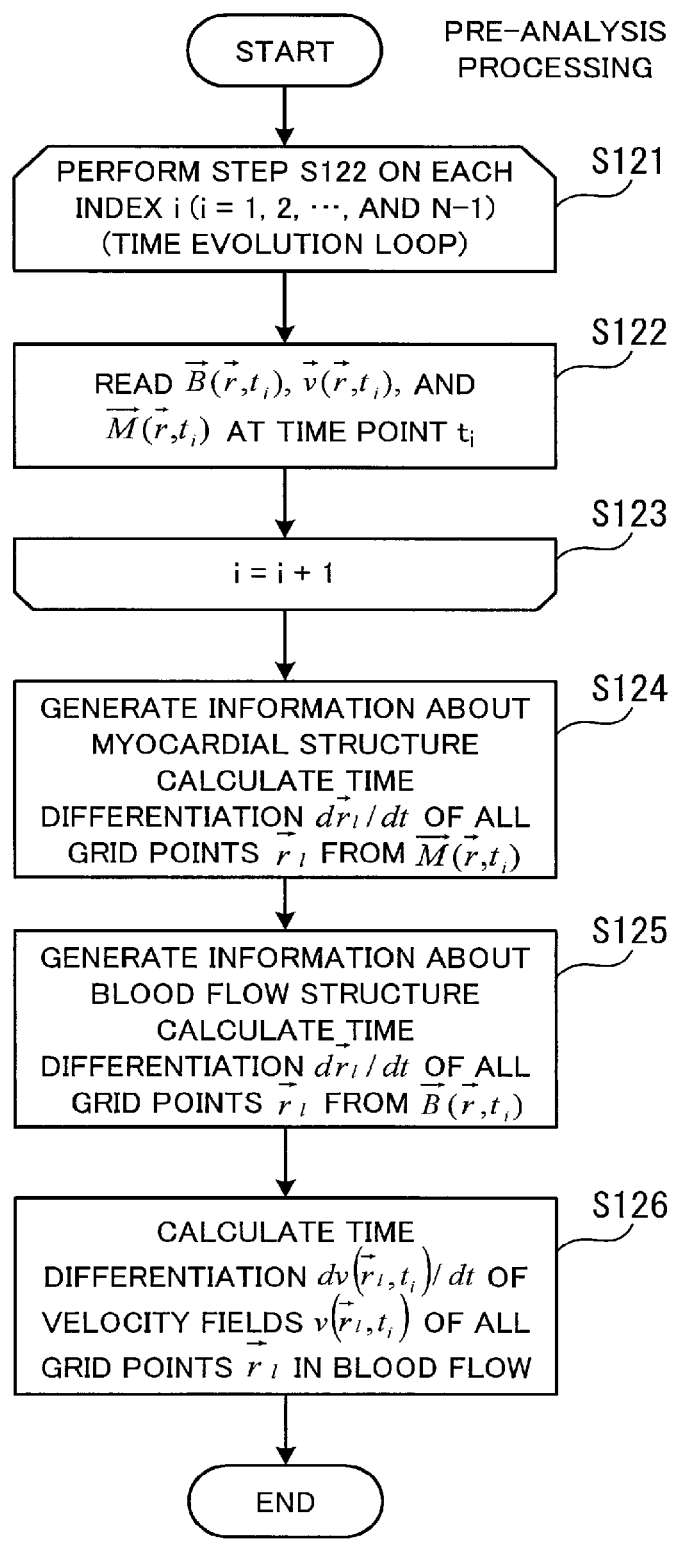
FIG. 10 is a flowchart illustrating an example of a procedure of pre-analysis processing.

FIG. 10 is a flowchart illustrating an example of a procedure of pre-analysis processing. Hereinafter, the processing illustrated in FIG. 10 will be described step by step.

[Step S121] The pre-analysis unit 140 performs step S122 on each of the indexes i sequentially from i=1 to i=N−1.

[Step S122] The pre-analysis unit 140 reads a vector B (vector r, $t_i$), a vector v (vector r, $t_i$), and a vector M (vector r, $t_i$) at the time point $t_i$ from the simulation result storage unit 110 via the information reading unit 130.

[Step S123] Each time the pre-analysis unit 140 performs step S122, the pre-analysis unit 140 adds 1 to the index i. After the pre-analysis unit 140 performs step S122 on the index i=N−1, the processing proceeds to step S124.

[Step S124] The pre-analysis unit 140 calculates a value of a time differential vector $dr_l/dt$ on a grid coordinate vector $r_l$ at the time point $t_i$ constituting the vector M (vector r, $t_i$), which is the myocardial structure information. The pre-analysis unit 140 performs this calculation for all the time points and all the grid points.

[Step S125] The pre-analysis unit 140 calculates a value of a time differential vector $dr_l/dt$ on a grid coordinate vector $r_l$ at the time point $t_i$ constituting the vector B (vector r, $t_i$), which is the blood flow structure information. The pre-analysis unit 140 performs this calculation for all the time points and all the grid points.

[Step S126] The pre-analysis unit 140 calculates a time differential vector dv (vector $r_l$, $t_i$)/dt of a velocity field vector v (vector $r_l$, $t_i$) on a grid coordinate vector $r_l$ at the time point $t_i$ of the blood flow. The pre-analysis unit 140 performs this calculation for all the time points and all the grid points.

The index l in steps S124 to S126 indicates a grid number. In addition, the present example assumes that $N_{M,elem}$ grid coordinates exist in total regarding the myocardium and that $N_{B,elem}$ grid coordinates exist in total regarding the blood flow.

Next, a method for calculating the values of the time differential vectors $dr_l/dt$ at the time point $t_i$ on the grid coordinate vectors $r_l$ of the myocardium and the blood flow portion will be described in detail. The values of the time differential vectors $dr_l/dt$ at all the grid points are calculated in the same way.

First, the pre-analysis unit 140 specifies a grid number l and acquires information about a position vector sequence $r_k(t_i)$ (i=0, 1, 2, . . . , n−1). Next, the pre-analysis unit 140 extracts the X, Y, and Z components of the vectors from the acquired information and stores the extracted components as coordinate sequences $X_l(t_i)$ (i=0, 1, 2, . . . , n−1), $Y_l(t_i)$ (i=0, 1, 2, . . . , n−1), and $Z_l(t_i)$ (i=0, 1, 2, . . . , n−1) in which n represents the number of files (n is an integer of 1 or more).

Next, regarding the X component, the pre-analysis unit 140 uses an interpolation method to calculate a smooth and continuous curve $X_l(t)$ that passes through all the points $X_l(t_i)$. As the interpolation method, a cubic spline may be used, for example. Any interpolation method other than a cubic spline may alternatively be used. In the cubic spline, the curve $X_l(t)$ is defined by expression (1) using an interpolating polynomial $X_{(l,i)}(t)$ defined per section $t_i \leq t \leq t_{(i+1)}$.

$$X_l(t)=X_{l,i}(t)(t_i \leq t \leq t_{i+1})(i=0,1,2,\ldots,n-1) \tag{1}$$

The following expression (2) is a specific form of the interpolation curve $X_{l,i}(t)$.

$$X_{l,i}(t)=a_{l,i}+b_{l,i}(t-t_i)+c_{l,i}(t-t_i)^2+d_{l,i}(t-t_i)^3 \tag{2}$$

However, since n represents one heart cycle, the pre-analysis unit 140 sets a cyclic boundary condition so that the (n+1)th value will correspond to the 0th value. For example, the pre-analysis unit 140 sets $t_{n+m}=t_m$. In addition, the pre-analysis unit 140 sets $X_{l,n+m}=S_{l,m}$ regarding a function value of the interpolation curve $X_{l,i}(t)$. In expression (2), while the coefficients $a_{l,i}$, $b_{l,i}$, $c_{l,i}$, and $d_{l,i}$ are unknown, by adding a condition for a smooth and continuous curve including the differentiation per section $t_i \leq t \leq t_{i+1}$, a linear simultaneous equation is established. By computationally solving this simultaneous equation, all sets of coefficients $a_{l,i}$, $b_{l,i}$, $c_{l,i}$, and $d_{l,i}$ are calculated (see "Numerical Recipes in C: The Art of Scientific Computing"). In addition, $dX_l/dt$ is directly calculated by the following expression (3).

$$dX_l/dt = b_{l,i} + 2c_{l,i}(t-t_i) + 3d_{l,i}(t-t_i)^2 \qquad (3)$$

In this way, a value of $dX_l/dt$ at the time point $t_i$ is calculated so that the first-order differentiation and second-order differentiation with respect to time are continuous.

Next, the pre-analysis unit 140 stores the sequence of coefficients $a_{l,i}$, $b_{l,i}$, $c_{l,i}$, and $d_{l,i}$ in the pre-analysis result Ω. An interpolation equation may also be calculated for the Y and Z components in accordance with the same procedure. The pre-analysis unit 140 calculates these coefficients for all the myocardium grid points and blood flow grid points. As a result, the values of the vectors $dr_l/dt$ are calculated.

Next, a procedure of calculating the time differential vector dv (vector $r_l$, $t_i$)/dt of the velocity field vector v (vector $r_l$, $t_i$) will be described. This time differential vector dv (vector $r_l$, $t_i$)/dt represents the acceleration of a grid point, assuming that the grid point is fixed in fluid and moves with the fluid. This is called Lagrangian coordinates in the field of fluid mechanics.

When the analysis target is incompressible fluid, if the acceleration is multiplied by the density of the fluid, the force applied to a particle on the grid point is obtained. Thus, calculating the acceleration of the grid point is calculating the magnitude and direction of the force applied to the particle on the grid point in incompressible fluid.

The components of the velocity field of the fluid may be displayed as velocity field vector $v=(v_x, v_y, v_z)$. While the x component $(v_x)$ of the velocity field will hereinafter be described, the y component $(v_y)$ of the velocity field may be calculated in the same way. When calculating the z component $(v_z)$ of the velocity field, the pre-analysis unit 140 calculates differentiation of a composite function. As a result, the following expression (4) is established.

$$\frac{dv_x(\vec{r}_l(t_i), t_i)}{dt} = \frac{d\vec{r}_l(t_i)}{dt} \cdot \nabla v_x(\vec{r}_l(t_i), t_i) + \frac{\partial v_x(\vec{r}_l(t_i), t_i)}{\partial t} \qquad (4)$$

From expression (4), time differentiation of the x component $(v_x)$ of the velocity field at the time point $t=t_i$ at the individual grid point (grid number k) is obtained. The vector $dr_k/dt$ at the coordinate vector $r_k$ of the grid number k has already been calculated by the interpolating polynomial. $\nabla v_x$ may be calculated by referring to "Finite Element Analysis Chapter 4 Finite Element Approximation" or the like. The partial differentiation with respect to time of the remaining velocity field is calculated by using the following expression (5).

$$\frac{\partial v_x(\vec{r}_l(t_i), t_i)}{\partial t} = \vec{a}_{ave} - \vec{v}_{ave} \cdot \nabla v_x(\vec{r}_l(t_{i+1}), t_{i+1}) \qquad (5)$$

In this expression (5) the vector $a_{ave}$ represents the average acceleration vector at a grid point of the grid number k on the Lagrangian coordinates, and the vector $v_{ave}$ represents the average velocity vector. The vector $a_{ave}$ and the vector $V_{ave}$ are defined by the following expressions (6) and (7).

$$\vec{a}_{ave} = \frac{\vec{v}(\vec{r}_l(t_{i+1}), t_{i+1}) - \vec{v}(\vec{r}_l(t_i), t_i)}{t_{i+1} - t_i} \qquad (6)$$

$$\vec{v}_{ave} = \frac{\vec{r}_l(t_{i+1}) - \vec{r}_l(t_i)}{t_{i+1} - t_i} \qquad (7)$$

Expression (5) includes the term of the average acceleration (vector $a_{ave}$) of an individual grid point on the Lagrangian coordinates and the term of the average velocity (vector $v_{ave}$). This is, since the individual grid point moves, to correct the apparent force attributable to the motion of the grid point.

As an analysis method used when an individual grid point performs accelerated motion, there is ALE (Arbitrary Lagrangian-Eulerian) method, for example.

Figure 11:
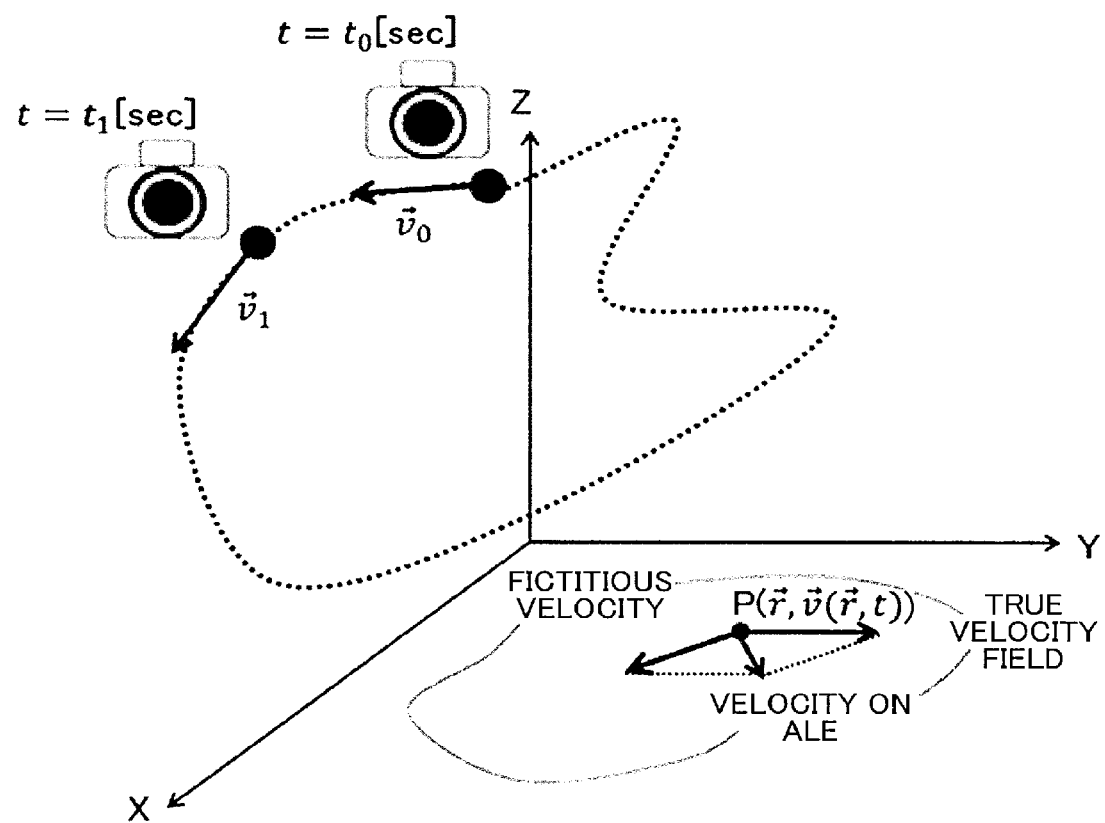
FIG. 11 illustrates a principle of apparent force that occurs when a grid point itself controlled based on an Arbitrary Lagrangian-Eulerian method is in motion.

FIG. 11 illustrates a principle of apparent force that occurs when a grid point itself controlled based on an ALE method is in motion. After a grid point controlled based on an ALE method moves based on a beat in accordance with cardiac contraction, the grid point returns to its original position and moves in accordance with a heartbeat. In this case, since the velocity of the grid point changes momentarily, acceleration occurs. However, if an observation device is set at the grid point, the observer interprets that the observer is stationary. It looks as if the effect due to the accelerated motion of the observer acts on the fluid as apparent force. Thus, correction based on the accelerated motion of the observer needs to be made. The procedure of correcting the apparent force is included in expressions (5) to (7). In this way, time differentiation of the velocity field at the time point $t=t_i$ at the individual grid point is calculated. The pre-analysis unit 140 calculates the time differentiation of the individual velocity field of the blood flow at all the grid points and stores a data set including the time differentiation of the velocity field at the individual grid point in the pre-analysis result storage unit 120 as the pre-analysis result Q.

Next, the time evolution calculation processing (step S112) will be described in detail.

Figure 12:
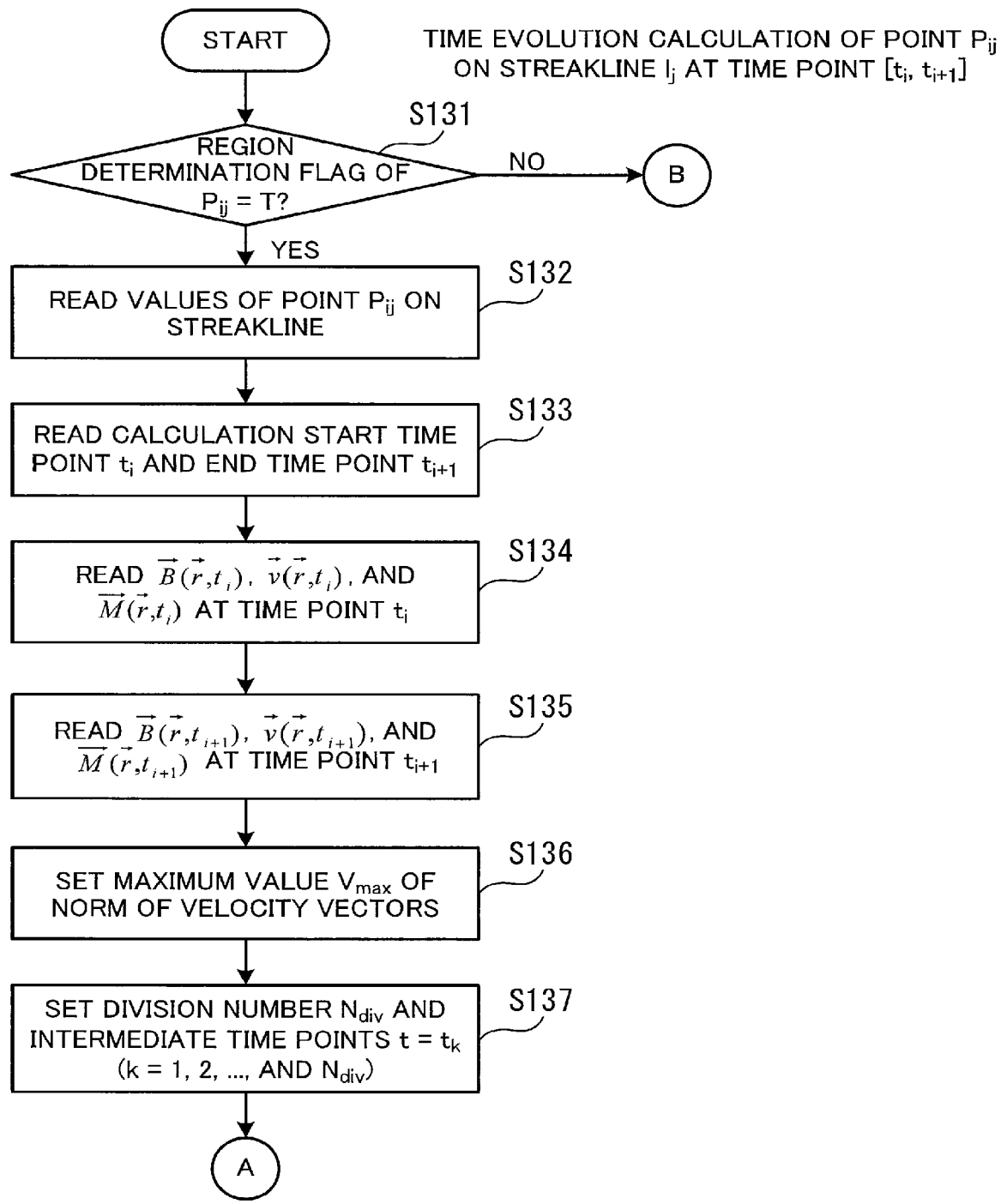
FIGS. 12 and 13 are a flowchart illustrating a procedure of time evolution calculation processing.
Figure 13:
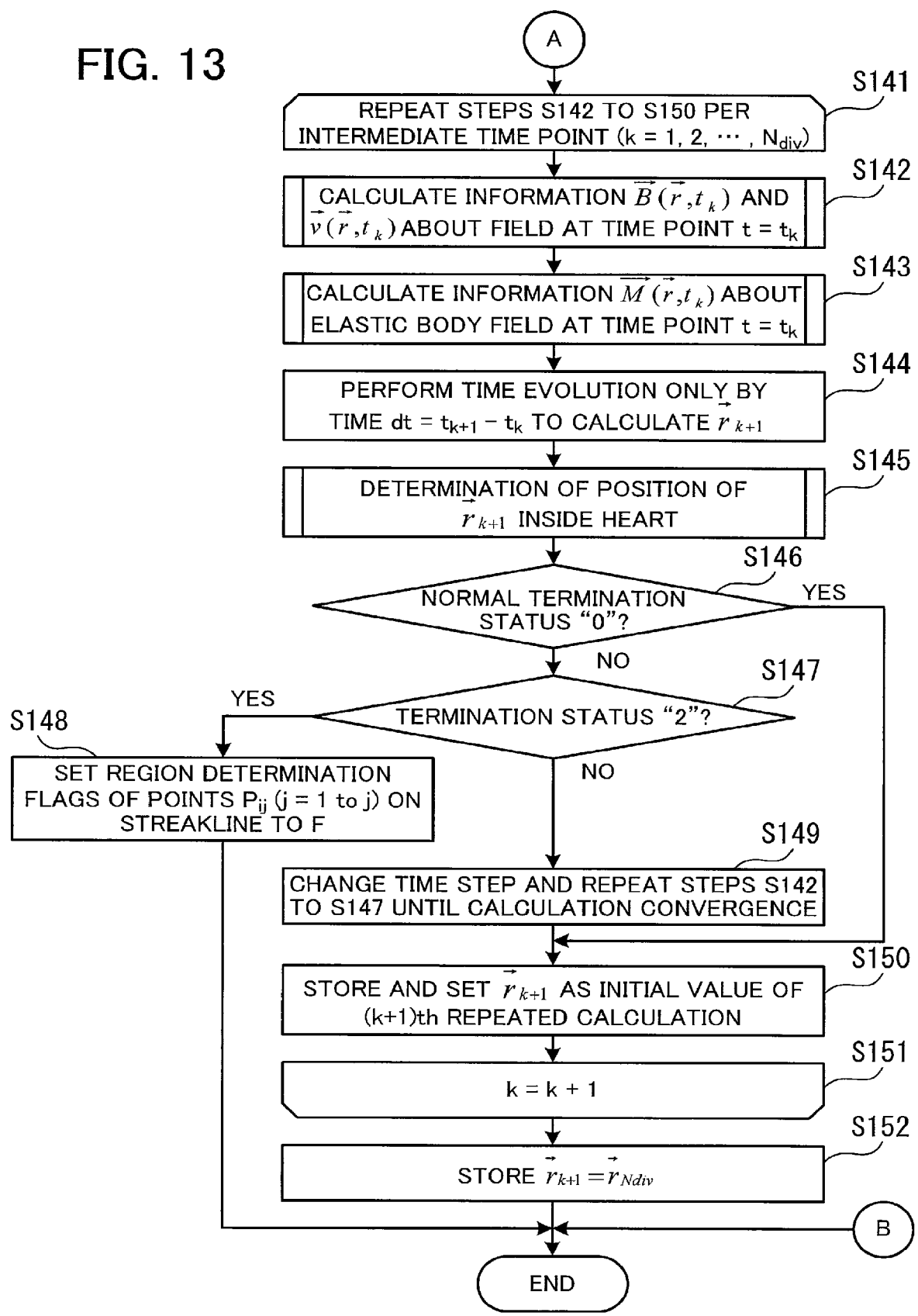

FIGS. 12 and 13 are a flowchart illustrating a procedure of the time evolution calculation processing. Hereinafter, the processing illustrated in FIG. 12 will be described step by step.

[Step S131] The streakline calculation unit 150 reads the region determination flag of the point $P_{ij}$. The streakline calculation unit 150 determines whether the region determination flag indicates "T". When the region determination flag indicates "T", the processing proceeds to step S132. When the region determination flag indicates "F", the streakline calculation unit 150 determines that this point has fallen outside the region and ends the time evolution calculation processing without performing the calculation. Thus, when the region determination flag indicates "F", the streakline calculation unit 150 does not update the coordinate values.

[Step S132] The streakline calculation unit 150 reads the coordinate values of the point $P_{ij}$.

[Step S133] The streakline calculation unit 150 reads calculation start time point $t=t_i$ and calculation end time point $t=t_{i+1}$ from the memory 102.

[Step S134] The streakline calculation unit 150 reads a grid information vector B (vector r, $t_i$) and a velocity field vector v (vector r, $t_i$) of the fluid portion at the calculation start time point $t=t_i$ from the file flui(i).inp via the information reading unit 130. In addition, the streakline calculation unit 150 reads a vector M (vector r, $t_i$), which is the grid information about the elastic body of the myocardium portion (information about the structure of the myocardium), from the file stru(i).inp via the information reading unit 130.

[Step S135] The streakline calculation unit 150 reads a grid information vector B (vector r, $t_{i+1}$) and a velocity field vector v (vector r, $t_{i+1}$) of the fluid portion at the calculation end time point t=$t_{i+1}$ from the file flui(i+1).inp via the information reading unit 130. In addition, the streakline calculation unit 150 reads a vector M (vector r, $t_{i+1}$) from the file stru(i+1).inp via the information reading unit 130.

[Step S136] The streakline calculation unit 150 calculates the norm of the velocity field vectors of the grid points indicated by the file flui(i).inp and the file flui(i+1).inp (the length of the velocity field vectors) and calculates the maximum value of the velocity in the corresponding time section by using an interpolating expression. The streakline calculation unit 150 stores the calculated maximum value in the memory 102 as $V_{max}$.

[Step S137] If the streakline calculation unit 150 calculates the section [$t_i$, $t_{i+1}$] in a single time evolution, the accuracy is not sufficient. Thus, the streakline calculation unit 150 equally divides the section [$t_i$, $t_{i+1}$] by $N_{div}$ ($N_{div}$ is an integer of 1 or more) and sets intermediate time points (t=$t_k$ (k=1, 2, ..., and $N_{div}$)). In this way, the section is divided into [$t_i$, $t_i+\Delta t$], [$t_i+\Delta t$, $t_i+2\Delta t$], ..., and [$t_i+(N_{div}-1)\Delta t$, $t_{i-1}$]. The streakline calculation unit 150 sets an optimum value as the division number $N_{div}$ by itself. The division number $N_{div}$ may be given externally. Next, the processing proceeds to step S141 in FIG. 13.

Hereinafter, the processing illustrated in FIG. 13 will be described step by step.

[Step S141] The streakline calculation unit 150 performs the time evolution calculation by repeating a group of steps S142 to S150 per intermediate time point (t=$t_k$ (k=1, 2, ..., and $N_{div}$)) from k=1 to k=$N_{div}$. As a result, a coordinate vector $r_k$ is obtained for each intermediate time point t=$t_k$, and a coordinate vector $r_{Ndiv}$=vector $r_{i+1}$ of a point $P_{i+1,j}$ at the time point t=$t_{i+1}$ is obtained.

[Step S142] The streakline calculation unit 150 calculates information about the field at the time point t=$t_k$ (a fluid structure information vector B (vector r, $t_k$) and a velocity field vector v (vector r, $t_k$)). This step will be described in detail below with reference to FIG. 17.

[Step S143] The streakline calculation unit 150 calculates information about the elastic body field at the time point t=$t_k$ (a myocardium structure information vector M (vector r, $t_k$)). This step will be described in detail below with reference to FIG. 18.

[Step S144] The streakline calculation unit 150 performs time evolution only by time dt=$t_{k+1}-t_k$ to calculate a vector $r_{k+1}$.

The streakline calculation unit 150 may perform the time evolution per intermediate time point in steps S142 to S144 as follows. Assuming that the point $P_{ij}$ is at the vector $r_k(t_k)$ when the time point t=$t_k$, a streakline equation is expressed by expression (8).

$$\frac{d\vec{r}(t_k)}{dt} = \vec{v}(\vec{r}(t_k), t_k) \quad (8)$$

In expression (8), the vector v (vector r, t) is the velocity (field) at the time point t and the position vector r. Thus, the coordinates after the time $\Delta t$ are calculated by numerically solving the expression (8), which is an ordinary differential equation. The following calculation expressions are obtained by solving expression (8) with the fourth-order Runge-Kutta method. This idea is also applicable to a higher order Runge-Kutta type formula, and accurate calculation is achieved (see "LOW-ORDER CLASSICAL RUNGE-KUTTA FORMULAS WITH STEPSIZE CONTROL AND THEIR APPLICATION TO SOME HEAT TRANSFER PROBLEMS"). Herein, as a typical example, a fourth-order Runge-Kutta formula will be described.

With a fourth-order Runge-Kutta formula, the following expressions (9) and (10) are established.

$$\vec{r}(t_{k+1}) = \vec{r}(t_k) + \frac{\Delta t}{6}\sum_{I=1}^{4}\vec{V}_I \quad (9)$$

$$\vec{V}_I = v(\vec{r}(t_k) + \alpha_I \vec{V}_{I-1}, t_k + \beta_I) \quad (10)$$

The streakline calculation unit 150 acquires a coefficient $\alpha_I$ and a coefficient $\beta_I$ in expression (10) from a table of Runge-Kutta coefficients.

FIG. 14 illustrates an example of the table of Runge-Kutta coefficients. In the table of Runge-Kutta coefficients illustrated in FIG. 14, coefficients $\alpha_I$ and $\beta_I$ are stored per I (I is an integer from 1 to 4). For example, the table of Runge-Kutta coefficients as illustrated in FIG. 14 is stored in advance in the memory 102.

The velocity field vector v (vector r, $t_k$) at any position vector r when the time point t=$t_k$ may be calculated from the vector v (vector r, $t_i$), the vector v (vector r, $t_{i+1}$), the vector B (vector r, $t_i$), the vector B (vector r, $t_{i+1}$), the vector M (vector r, $t_i$), and the vector M (vector r, $t_{i+1}$). Assuming that the moving boundary surface at the time point t=$t_k$ is denoted by $S_k$, information about the velocity filed on the moving boundary surface $S_k$ used in steps S142 and 143 may also be calculated. Hereinafter, the moving boundary surface will simply be referred to as a "boundary surface". Thus, intermediate values needed for time evolution may be calculated by using expressions (9) and (10) and the table of Runge-Kutta coefficients illustrated in FIG. 14. By substituting these results into expression (8), a vector r ($t_{k+1}$) is calculated. The time evolution processing will be described in detail below with reference to FIG. 20. The following description returns to FIG. 13.

[Step S145] The streakline calculation unit 150 performs determination of the position of the vector $r_{k+1}$ inside the heart. The streakline calculation unit 150 performs this processing because the calculated vector $r_{k+1}$ includes an infinite time width error and could enter the myocardium. After the position determination as a subroutine, a status indicating the result of the position determined is acquired. For example, when the vector has not crossed or entered the myocardium, "0" or "2" as a normal termination status is acquired. When the vector $r_{k+1}$ indicates a position in an element in the analysis target fluid (for example, in an atrium or a ventricle), the status "0" is acquired. When the vector $r_{k+1}$ indicates a position outside an element in the analysis target fluid (for example, in an artery), the status "2" is acquired. This step will be described below in detail with reference to FIG. 23.

[Step S146] The streakline calculation unit 150 determines whether the determination result indicates the status "0" indicating normal termination. When the determination result indicates the status "0", the processing proceeds to step S150. When the determination result does not indicate the status "0", the processing proceeds to step S147.

[Step S147] The streakline calculation unit 150 determines whether the determination result indicates the status "2" indicating termination. The case in which the status "2" is acquired corresponds to a case in which the point $P_{ij}$ has moved to an external element outside the system such as to a large artery through the fluid boundary during the calculation. When the determination result indicates the status "2", the processing proceeds to step S148. Otherwise, the processing proceeds to step S149.

[Step S148] When the point $P_{ij}$ has fallen outside the system, the streakline calculation unit 150 sets the region determination flags of the points (j=1 to j) on the streakline to "F". The individual region determination flag "F" indicates that the corresponding point $P_{ij}$ has fallen outside the analysis region. Next, the streakline calculation unit 150 ends the time evolution calculation processing. In this way, when the termination status indicates "2", the streakline calculation unit 150 determines that the point $P_{ij}$ has fallen outside the system and sets the region determination flags to "F". A streakline is drawn by connecting curves formed by sequentially connecting points $P_{i1}, P_{i2}, P_{i3}, \ldots,$ and $P_{iN}$. Thus, when any point $P_{ij}$ is determined to have fallen outside the region, there is no reason to draw the previous points emitted from the particle generation source. Thus, the streakline calculation unit 150 sets all the region determination flags of the points $P_{ij}$ (j=1 to j) to "F" and ends the processing.

[Step S149] When the determination result does not indicate normal termination (when the status is neither "0" nor "2"), the streakline calculation unit 150 decreases the time step functioning as a control parameter. Namely, the streakline calculation unit 150 further divides the calculation by more time points and repeats the group of steps S142 to S147. The streakline calculation unit 150 continues the repletion of steps S142 to S147 until the calculation converges in accordance with a variable time stepping method. After decreasing the time step, when the streakline calculation unit 150 determines normal termination, the processing proceeds to step S150.

When the vector $r_{k+1}$ has fallen outside the predicted sphere, the streakline calculation unit 150 does not determine normal termination, either. In this case, for example, by increasing the radius of the predicted sphere and performing recalculation, the streakline calculation unit 150 is able to prevent the vector $r_{k+1}$ from falling outside the predicted sphere.

[Step S150] The streakline calculation unit 150 stores the vector $r_{k+1}$ in a memory and sets the stored value as the initial value of the (k+1)th repeated calculation.

[Step S151] Each time the streakline calculation unit 150 performs the group of step S142 to S150, the streakline calculation unit 150 adds 1 to the index k and repeats the processing. When the streakline calculation unit 150 completes the time evolution calculation on all the intermediate time points (k=$N_{div}$), the processing proceeds to step S152.

[Step S152] The streakline calculation unit 150 stores the finally calculated vector $r_{Ndiv}$ as the vector $r_{k+1}$ in a memory.

The coordinates of the points on a streakline are updated by the processing illustrated in FIGS. 12 and 13.

FIG. 15 illustrate data examples of streaklines. As illustrated in FIG. 15, the coordinate values of the points on the streaklines are set per analysis time point. As the initial values of the points on the streaklines at the time point $t=t_0$, the coordinate values of the particle generation sources are set. When the time point $t=t_1$, the coordinate values of the points indicating the positions of the initially emitted particles are updated. Next, as the time point is updated, new particles are emitted, and the coordinate values of the points indicating the positions of the new and old particles emitted are updated. In FIG. 15, the coordinate values of the points whose positions have been changed from their previous time points are underlined.

Next, a procedure of obtaining the field information at a time point $t_k$ for which no output data has been given (the vector B (vector r, $t_k$), the vector v (vector r, $t_k$), and the vector M (vector r, $t_k$)) will be described. These items of field information are used in the calculation of the above expressions (9) and (10) described in the time evolution based on the Runge-Kutta method.

As the simulation result, only the data at the time point $t=t_i$ and $t=t_{i+1}$ has been outputted. Namely, since no grid coordinates and velocity fields at the intermediate time $t_k$, which are calculated by the Runge-Kutta method, are defined, the streakline calculation unit 150 calculates approximate values of the field information from the velocity fields of the output files. A key consideration for this calculation is to move the grid position momentarily when the simulation is executed. While the grid position may be determined in any way, an Arbitrary Lagrangian-Eulerian (ALE) method is often used to solve a problem in which a boundary of an object such as a heart moves. In the ALE method, the coordinates used in a simulation are independently determined so as not to deteriorate the accuracy of the solution of a partial differential equation described. In many cases, a partial differential equation is used for this determination. However, the governing equation for determining the grid position is not available to one in the position of the data analysis while only the output values of the grid points given are available. In this case, the positions of the grid points continuously change over time.

Figure 16:
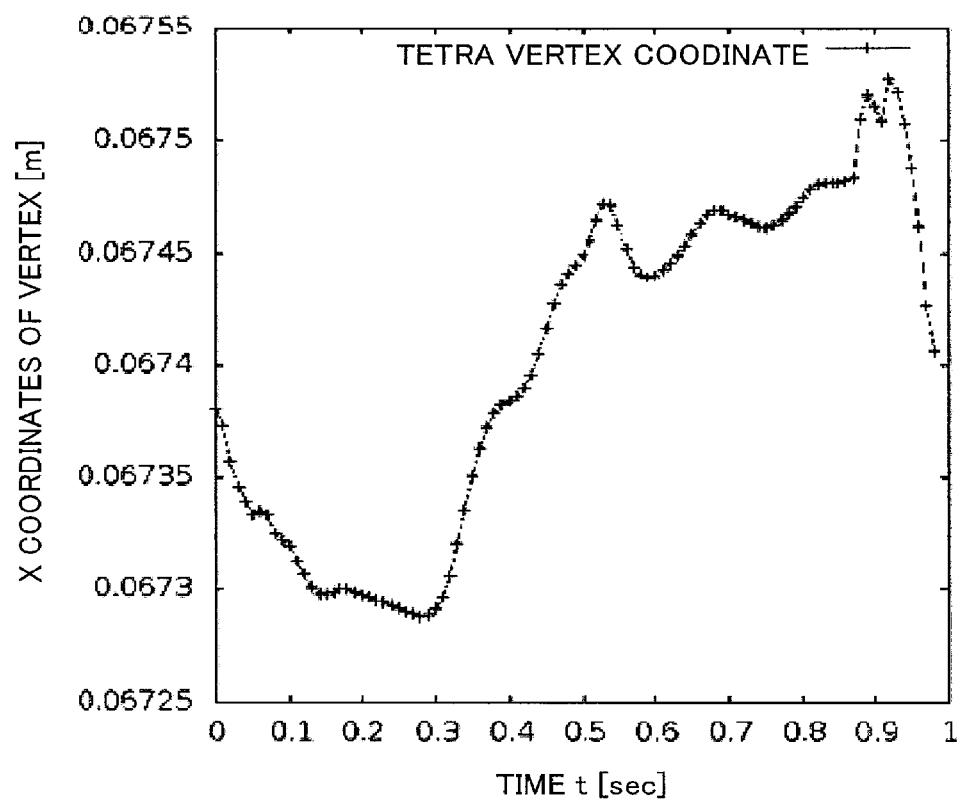
FIG. 16 illustrates how the position of a grid point continuously changes over time.

FIG. 16 illustrates how the position of a grid point continuously changes over time. In FIG. 16, the horizontal axis represents time, and the vertical axis represents X coordinate values of a grid point (vertex). As illustrated in FIG. 16, the position of an individual grid point continuously changes over time. Thus, in view of this fact, the streakline calculation unit 150 estimates a grid position at any time point by using an interpolation method.

Figure 17:
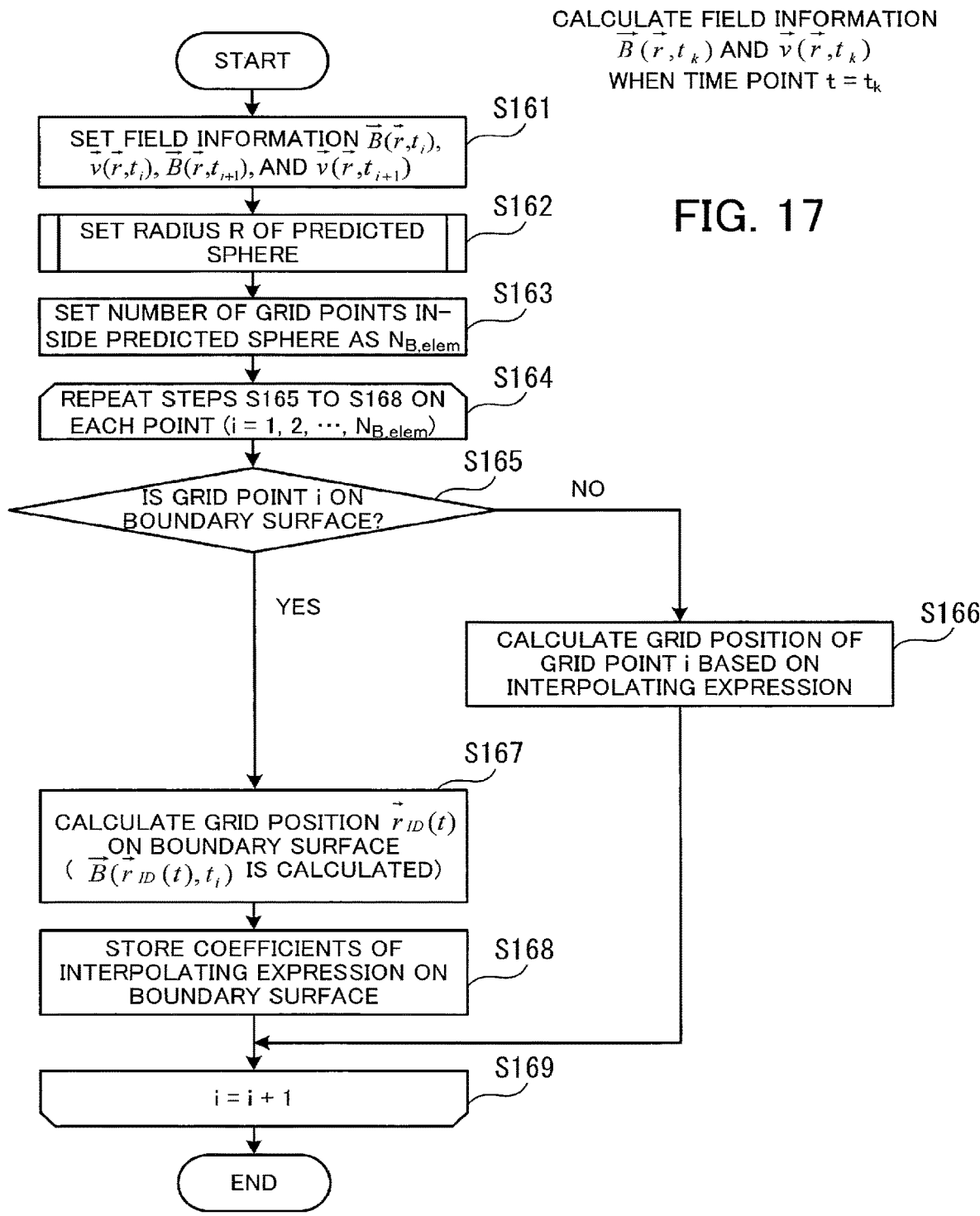
FIG. 17 is a flowchart illustrating an example of a procedure of processing for calculating field information when a time point $t=t_k$.

FIG. 17 is a flowchart illustrating an example of a procedure of processing for calculating field information when the time point $t=t_k$. Hereinafter, the processing illustrated in FIG. 17 will be described step by step.

[Step S161] The streakline calculation unit 150 sets field information at the time point $t_k$ in a memory. The set information includes the vector B (vector r, $t_i$), the vector v (vector r, $t_i$), the vector B (vector r, $t_{i+1}$), and the vector v (vector r, $t_{i+1}$).

The time point $t_k$ satisfies $t_i \leq t_k \leq t_{i+1}$. In addition, the vector B (vector r, $t_i$), the vector v (vector r, $t_i$), the vector M (vector r, $t_i$), the vector B (vector r, $t_{i+1}$), the vector v (vector r, $t_{i+1}$), and the vector M (vector r, $t_{i+1}$) are known. These vector values have already been read from files in steps S134 and S135.

First, the streakline calculation unit 150 performs the following processing on the grid points that define the structure of the fluid portion. However, for reduction of the calculation amount, the streakline calculation unit 150 theoretically calculates the maximum moving distance of the point $P_{i+1j}$ and performs the processing on only the grid points inside a sphere having a radius R equal to the maximum moving distance. This sphere will hereinafter be referred to as a "predicted sphere".

[Step S162] The streakline calculation unit 150 sets the radius R of the predicted sphere. This processing will be described in detail below with reference to FIG. 26.

[Step S163] The streakline calculation unit 150 searches for fluid grid points inside the radius R of the predicted sphere and sets the number of grid points inside the predicted sphere as $N_{H,elem}$.

[Step S164] The streakline calculation unit 150 performs a group of steps S165 to S168 on each of the $N_{B,elem}$ grid points inside the radius R of the predicted sphere.

[Step S165] The streakline calculation unit 150 determines whether the grid point i is on a boundary surface. If the grid point i is on a boundary surface, the processing proceeds to step S167. If not, the processing proceeds to step S166.

Depending on the determination of whether the grid point i is on a boundary surface in step S165, the processing proceeds to a different step. This is to calculate the coordinates of the grid point i at any time point $t_k$ by interpolation. When the grid point i is on a boundary surface S(t) between the myocardium and the blood flow, a slip-free boundary condition is set on the blood flow with respect to the myocardium.

[Step S166] On the basis of an interpolating expression about the grid point i, the streakline calculation unit 150 calculates the grid position. For example, the interpolating expression is the above expression (2). The pre-analysis result Ω holds the result of the interpolating expression (expression (2)) about the coordinates of the grid point i with respect to time. Thus, the streakline calculation unit 150 is able to determine the grid coordinates at any time point from the pre-analysis result Ω. Next, the processing proceeds to step S169.

[Step S167] If the grid point i is on the boundary surface S(t), the streakline calculation unit 150 calculates the position of the grid point i as follows so that the boundary condition is met.

When the grid point i is on the boundary surface S(t), a point in the topology space formed by the corresponding velocity field is assumed to be (vector $r_{ID}(t)$, vector $v_{ID}(t)$). Since values at the time points $t_i$ and $t_{i+1}$ have been outputted, a curve passing through two points (vector $r_{ID}(t_i)$, vector $v_{ID}(t_i)$) and (vector $r_{ID}(t_{i+1})$, vector $v_{ID}(t_{i+i})$) may be calculated. A relationship represented by the following expression (11) is established regarding the grid position vector $r_{ID}(t)$ and the velocity field vector $v_{ID}(t)$.

$$\frac{d}{dt}\vec{r}_{ID}(t) = \vec{v}_{ID}(t) \tag{11}$$

Thus, there are four conditional expressions. Regarding the grid point i on the boundary surface S(t), by defining the vector $_{ID}(t)$ with a three-order equation with respect to time, the four conditions are satisfied. Thus, the vector $r_{ID}(t)$ is determined from the following expression (12).

$$\vec{r}_{ID}(t) = \sum_{k=0}^{3} \vec{a}_k (t - t_i)^k \tag{12}$$

Regarding a coefficient vector $a_i$, assuming that components of the vector $r_{ID}(t)$ are expressed by $\xi_{ID}(\xi=x, y, z)$ and the corresponding differential components are expressed by $v\xi(\xi=x, y, z)$, the following expressions are obtained.

$$a_{3\xi} = -2\frac{\Delta\xi_{ID}}{(\Delta t_i)^3} + \frac{v_\xi(t_i) + v_\xi(t_{i+1})}{(\Delta t_i)^2} \tag{13}$$

-continued $$a_{2\xi} = \frac{1}{2}\frac{\Delta v_\xi}{\Delta t_i} - \frac{3}{2}\frac{v_\xi(t_i) + v_\xi(t_{i+1})}{\Delta t_i} + 3\frac{\Delta\xi_{ID}}{(\Delta t_i)^2} \tag{14}$$

$$a_{1\xi} = v_\xi(t_i) \tag{15}$$

$$a_{0\xi} = \xi_{ID}(t_i) \tag{16}$$

In these expressions, the following relationships are used.

$$\Delta t_i = t_{i+1} - t_i \tag{17}$$

$$\Delta\xi_{ID} = \xi_{ID}(t_{i+1}) - \xi_{ID}(t_i) \tag{18}$$

$$\Delta v_\xi = v_\xi(t_{i+1}) - v_\xi(t_i) \tag{19}$$

In this way, a group of position vectors $r_{ID}(t)$ on the boundary surface S(t) at any time point is acquired. Thus, by calculating the positions of all the grid points i in the fluid, the streakline calculation unit 150 is able to determine the vector B (vector r, $t_k$), which is the information about the structure of the fluid.

[Step S168] The streakline calculation unit 150 stores the coefficients calculated by using the interpolating expression (expression (12)) in the memory 102. With expression (12), the velocity field may be calculated simultaneously. The velocity field may be calculated here or by using expressions (11) and (12) as needed. Thus, the streakline calculation unit 150 stores only the coefficient calculated by using the interpolating expression (expression (12)).

[Step S169] Each time the streakline calculation unit 150 performs the group of steps S165 to S168, the streakline calculation unit 150 adds 1 to the index i and repeats the group of steps S165 to S168. When the streakline calculation unit 150 has completed the calculation on the index i=$N_{B,elem}$, the streakline calculation unit 150 has completed the calculation of the positions of all the grid points i inside the predicted sphere.

As in the case of the field information, also for the vector M (vector r, t), which is the myocardium structure information, the streakline calculation unit 150 is able to calculate the grid point information at any time point.

Figure 18:
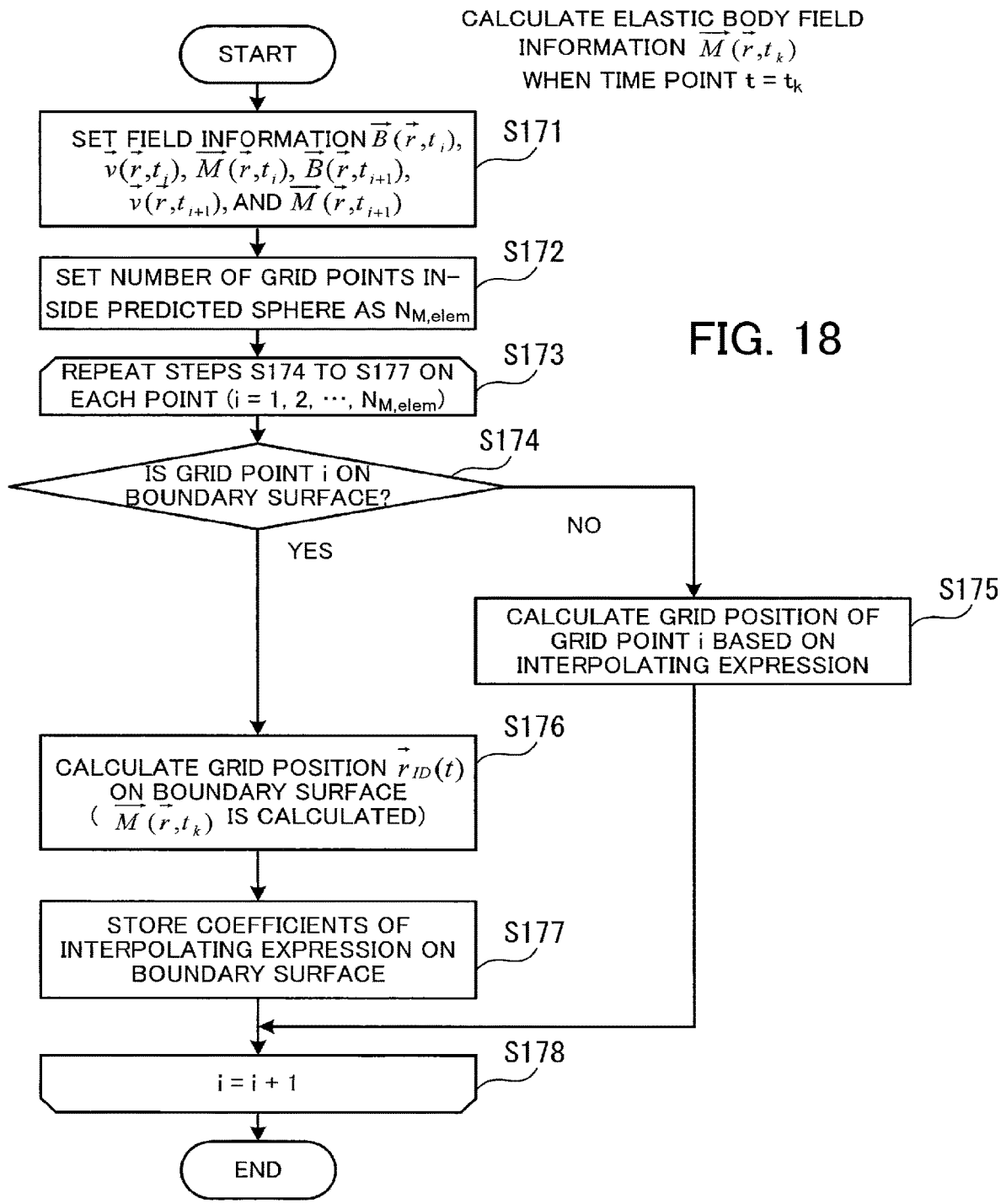
FIG. 18 is a flowchart illustrating an example of a procedure of processing for calculating elastic body field information when the time point $t=t_k$.

FIG. 18 is a flowchart illustrating an example of a procedure of processing for obtaining elastic body field information when the time point t=$t_k$. Hereinafter, the processing illustrated in FIG. 18 will be described step by step.

[Step S171] The streakline calculation unit 150 sets the read myocardium structure information in a memory. The set information includes the vector B (vector r, $t_i$), the vector v (vector r, $t_i$), the vector M (vector r, $t_i$), the vector B (vector r, $t_{i+1}$), the vector v (vector r, $t_{i+1}$), and the vector M (vector r, $t_{i+1}$).

[Step S172] The streakline calculation unit 150 searches for the structure of the myocardium inside the predicted sphere based on the radius R thereof and searches for the grid points i of the myocardium. The radius R of the predicted sphere is the same radius R as used in the processing performed on the fluid portion. The streakline calculation unit 150 sets the detected number of grid points i as $N_{M,elem}$.

[Step S173] The streakline calculation unit 150 performs a group of steps S174 to S177 on each of the grid points i inside the radius R of the predicted sphere.

[Step S174] The streakline calculation unit 150 determines whether the grid point i is on the boundary surface S(t). If the grid point i is on the boundary surface S(t), the processing proceeds to step S176. If not, the processing proceeds to step S175.

[Step S175] The streakline calculation unit 150 calculates the position of the grid point i in accordance with the interpolating expression (expression (2)) by using the pre-analysis result Ω. Next, the processing proceeds to step S178.

[Step S176] The streakline calculation unit 150 calculates the coordinates of the grid point i in accordance with expression (12). By calculating the positions of all the grid points i in the fluid, the vector M (vector r, $t_k$), which is the fluid structure information, is determined.

[Step S177] The streakline calculation unit 150 stores the coefficients calculated by using the interpolating expression (expression (12)) in the memory 102. If the processing on the fluid is performed first, there is a grid point i whose position is the same as that of a grid point i on the fluid side. Thus, instead of performing steps S176 and S177, the streakline calculation unit 150 may acquire the coordinates of the grid point i from the calculation result in step S167 and store the coordinates.

[Step S178] Each time the streakline calculation unit 150 performs the group of steps S174 to S177, the streakline calculation unit 150 adds 1 to i and repeats the group of steps S174 to S177. When the streakline calculation unit 150 completes the calculation on the index i=$N_{M,elem}$, the streakline calculation unit 150 ends the processing for calculating the elastic body structure information when the time point t=$t_k$. In this way, the streakline calculation unit 150 is able to calculate the myocardium structure information vector M (vector r, $t_k$).

Next, a method for calculating a velocity field vector $v_I$ (vector $r_I(t)$, t) at a grid coordinate vector $r_I(t)$ in the blood flow at any time point t will be described.

This velocity field vector $v_I$ (vector $r_I(t)$, t) is used in the calculation of expressions (9) and (10) used to perform the time evolution of a point on a streakline with the Runge-Kutta method. When the time point for which output data is available is $t_i$, an integer i satisfying $t_i \leq t \leq t_{i+1}$ is acquired. The pre-analysis result Q holds the value of the grid coordinate vector $r_I(t_i)$ of the individual vertex at the time point $t_i$, the value of the velocity field vector $v_I$ (vector $r_I(t_i)$, $t_i$) at that point, and the time differential vector dv (vector $r_I(t_i)$, $t_i$)/dt of the velocity field. Thus, at the time points $t_i$ and $t_{i+1}$, the velocity fields and differentials have been given. Thus, a continuous curve including the differentials is assumed to be an interpolation curve. Since the velocity fields and the time differentials are given at the two time points, a three-order polynomial having four unknown variables as represented by expression (20) may be used as an interpolation curve.

$$\vec{v}_I(t) = \sum_{k=0}^{3} \vec{b}_{k,i}(t-t_i)^k \quad (t_i \leq t \leq t_{i+1}) \tag{20}$$

A coefficient vector $b_{k,i}$ is determined so that the velocity field vectors $v_i(t)$ at the two time points $t_i$ and $t_{i+1}$ are connected smoothly and continuously. When ξ=x, y, z, the coefficient are determined by using expressions (21) to (26). In the following expressions, the time differentials of the velocities in the individual axial directions are expressed by using "'" such as "$v'_x(t)$", "$v'_y(t)$", and "$v'_z(t)$".

$$b_{2,\xi} = 3\frac{v_\xi(t_{i+1}) - v_\xi(t_i)}{(t_{i+1}-t_i)^2} - (2v'_\xi(t_i) + v'_\xi(t_{i+1})) \tag{21}$$

-continued $$b_{3,\xi} = \frac{v'_\xi(t_i) + v'_\xi(t_{i+1})}{(t_{i+1}-t_i)^2} - 2\frac{v_\xi(t_{i+1}) - v_\xi(t_i)}{(t_{i+1}-t_i)^3} \tag{22}$$

$$\vec{b}_0 = (v_x(t_i), v_y(t_i), v_z(t_i)) \tag{23}$$

$$\vec{b}_1 = (v'_x(t_i), v'_y(t_i), v'_z(t_i)) \tag{24}$$

$$\vec{b}_2 = (b_{2,x}, b_{2,y}, b_{2,z}) \tag{25}$$

$$\vec{b}_3 = (b_{3,x}, b_{3,y}, b_{3,z}) \tag{26}$$

In this way, a velocity field at a given grid point i at any time point t is calculated.

Next, a method for calculating a velocity field vector v (vector r, t) at any coordinate vector r in the fluid at any time point t will be described.

Since any coordinate vector r in given blood flow belongs in the blood flow, an infinite element $I_I$ in the blood flow including the coordinate vector r is obtained. Assuming that the coordinates of the vertexes belonging to the infinite element $I_I$ are represented by a vector $r_I(t)$ and the velocity field by vector $v_I$ (vector $r_I(t_i)$, t), the velocity field vector v (vector r, t) at the coordinate vector r is determined from the following expression (27).

$$\vec{v}(\vec{r}, t) = \sum_{i=1}^{4} N_i(\vec{r}, t)\vec{v}_i(\vec{r}_i, t) \tag{27}$$

In expression (27), $N_i$ (vector r,t) is called a structure function. Next, a specific method for calculating a structure function of a first-order tetrahedral element.

Figure 19:
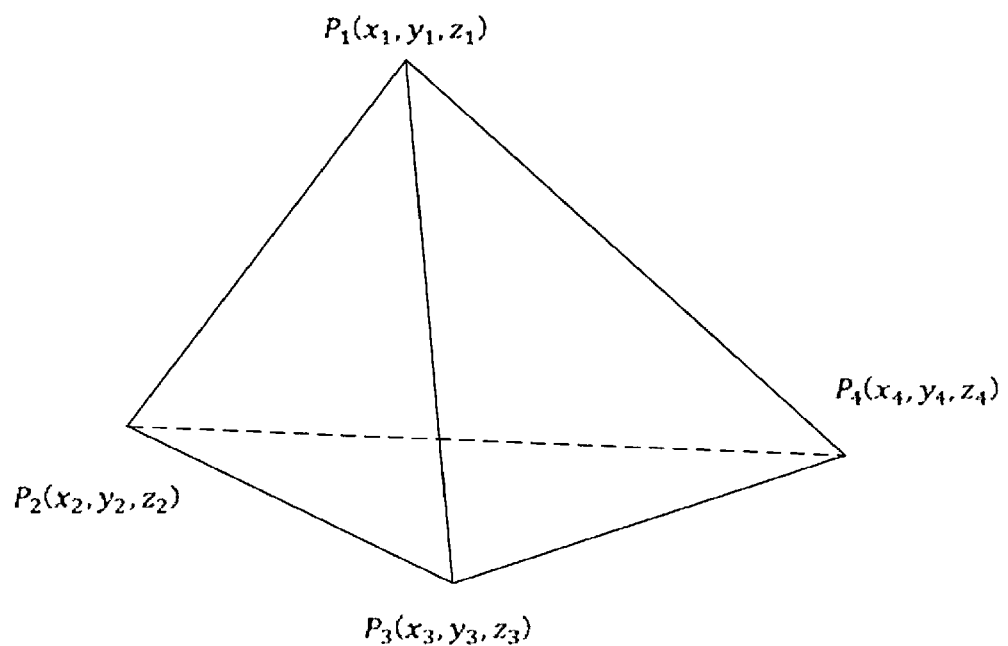
FIG. 19 illustrates an example of a tetrahedral element.

FIG. 19 illustrates an example of a tetrahedral element. Assuming that the coordinates of the vertexes of a tetrahedral element $I_I$ are $P_1(x_1,y_1,z_1)$, $P_2(x_2,y_2,z_2)$, $P_3(x_3,y_3,z_3)$, and $P_4(x_4,y_4,z_4)$, a structure function is given as expression (28).

$$N_i(x, y, z) = \frac{1}{6V}(a_i x + b_i y + c_i z + d_i) \tag{28}$$

In expression (28), V is the volume of the tetrahedral element $I_I$, and the coefficients $a_i$, $b_i$, and $c_i$ are obtained as a normal vector of an equation of a plane formed by three points other than i. For example, $N_1$ is determined from a normal vector of a plane formed by the three points $P_2$, $P_3$, and $P_4$ other than the point $P_1$. Assuming that the normal vector is a vector $n_1$, the calculation may be performed as vector $n_1$=($a_1$, $b_1$, $c_1$)=vector ($P_2P_3$)×vector ($P_2P_4$). The vector ($P_2P_3$) is a vector from the point $P_2$ to the point $P_3$. The vector ($P_2P_4$) is a vector from the point $P_2$ to the point $P_4$. "×" is a cross product of the vectors. Regarding the direction of the normal vector, when the tetrahedral element is seen from the triangle formed by $P_2$, $P_3$, and $P_4$ on the bottom surface, the direction of the vertex $P_1$ is positive. In addition, the coefficient $d_i$ is determined since the equation of the plane $a_i x+b_i y+c_i z+d_i=0$ passes through the point $P_2$ (or the point $P_3$ or $P_4$). Thus, when any point vector r is a point in the tetrahedral element $I_I$, the value of the structure function is determined in accordance with expression (28). In addition, the velocity field vector v (vector r, t) at the location is calculated from expression (27) (see "Finite Element Analysis Chapter 4 Finite Element Approximation").

Next, the time evolution processing based on the Runge-Kutta method will be described in detail.

After the positions of the myocardium and blood flow grid points i at any time point in steps S142 and S143 in FIG. 13 are obtained, the time evolution of the point vector $r(t_k)$ on the streakline is performed based on the Runge-Kutta method in step S144.

Figure 20:
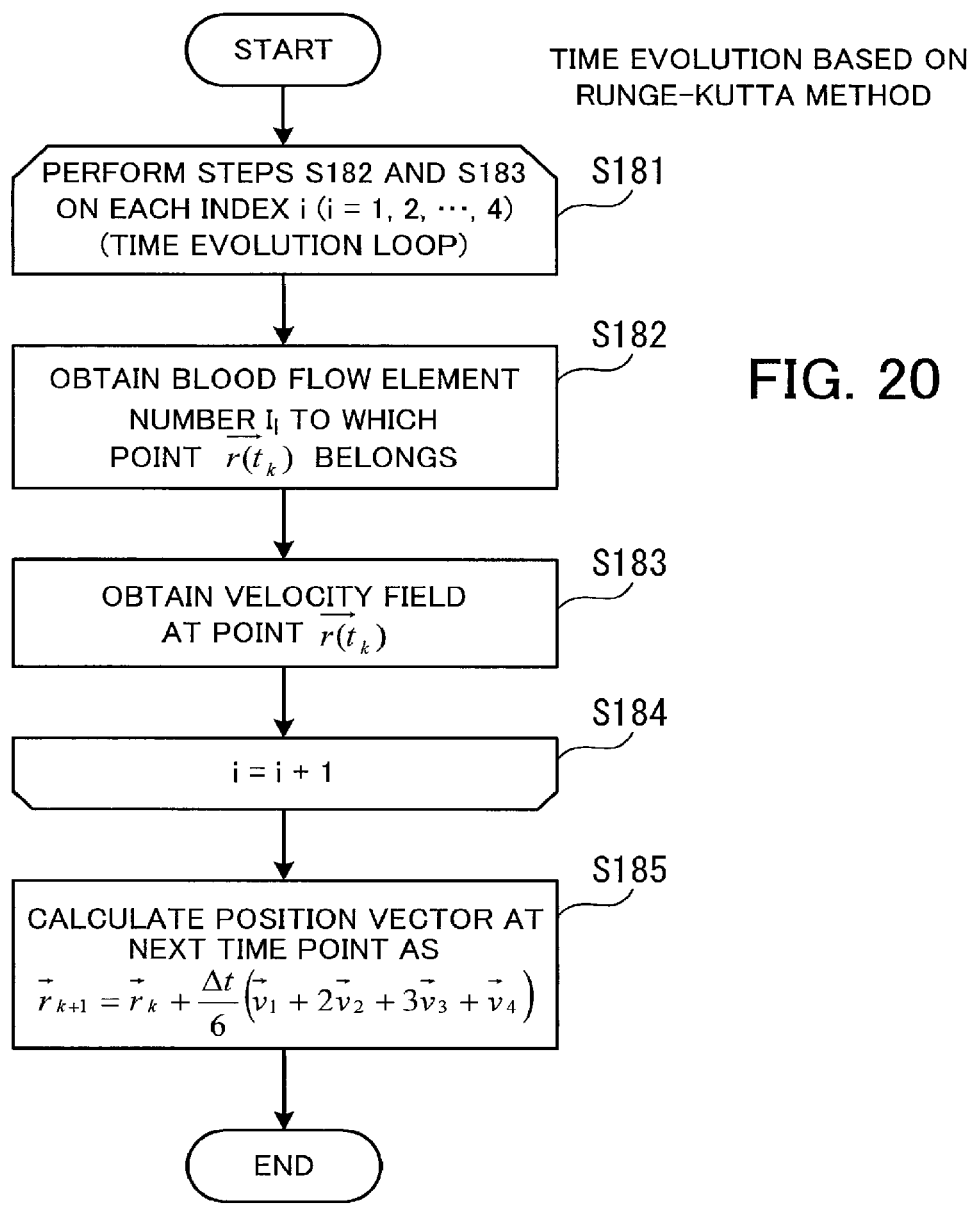
FIG. 20 is a flowchart illustrating an example of a procedure of time evolution processing based on a Runge-Kutta method.

FIG. 20 is a flowchart illustrating an example of a procedure of the time evolution processing based on the Runge-Kutta method. Next, the processing illustrated in FIG. 20 will be described step by step.

[Step S181] The streakline calculation unit 150 repeats a pair of steps S182 to S183 on each of the indexes i (i=1, 2, 3, 4) sequentially from i=1.

[Step S182] The streakline calculation unit 150 obtains a blood flow element number $I_l$ to which the vector $r(t_k)$ belongs and acquires information element for calculating the velocity vector based on expression (27).

[Step S183] The streakline calculation unit 150 calculates intermediate velocity vectors $v_i$ (i=1, 2, 3, 4) used in the Runge-Kutta method by using expressions (9) and (10). In the calculation of the vectors $v_i$, the velocity field at any coordinate in the fluid at any time point for which no data is given is also calculated. For example, while the vector $v_j$ is the value of the velocity field at the coordinate vector $r(t_k)$ at the time point $t_k$, the time point $t_k$ is not always a time point for which data is given by pre-analysis. In addition, the coordinate vector $r_k$ does not always represent coordinates of a grid point i in the fluid for which data is given. Thus, the velocity field at any coordinate vector r at any time point t is calculated.

For example, since the coordinate vector $r(t_k)$ and the time point $t_k$ are given, the velocity field is calculated from the above calculation method (expression (27)) of the velocity field vector v (vector r, t) at any coordinate vector r in the blood flow at any time point t. A vector $v_2$ includes information about the vector $v_1$, and the vector $v_1$ has already been calculated. Thus, the velocity field may also be calculated from the calculation method (expressions (20) and (27)) of the velocity field vector $v_1$ (vector $r_i(t)$, t) at the grid coordinate vector $r_i(t)$ in the blood flow at any time point t.

[Step S184] Each time the streakline calculation unit 150 performs the pair of steps S182 and S183, the streakline calculation unit 150 adds 1 to i and repeats the pair of steps S182 and S183. When the streakline calculation unit 150 completes the calculation on i=4, the streakline calculation unit 150 completes the calculation of all the vectors $v_i$ (i=1, 2, 3, 4), and the processing proceeds to step S185.

[Step S185] The streakline calculation unit 150 calculates a coordinate vector $r(t_{k+1})$ of the streakline at the next time point $t_{k+1}$ from expression (9).

Next, the determination of the position inside the myocardium will be described in detail.

Hereinafter, a procedure of determining the position of the vector $r_{k+1}$ obtained as a result of the time evolution inside the heart will be described. Since the Runge-Kutta method and the like include finite errors, the position vector $r_{k+1}$ obtained as a calculation result could fall on an unrealistic location.

Figure 21:
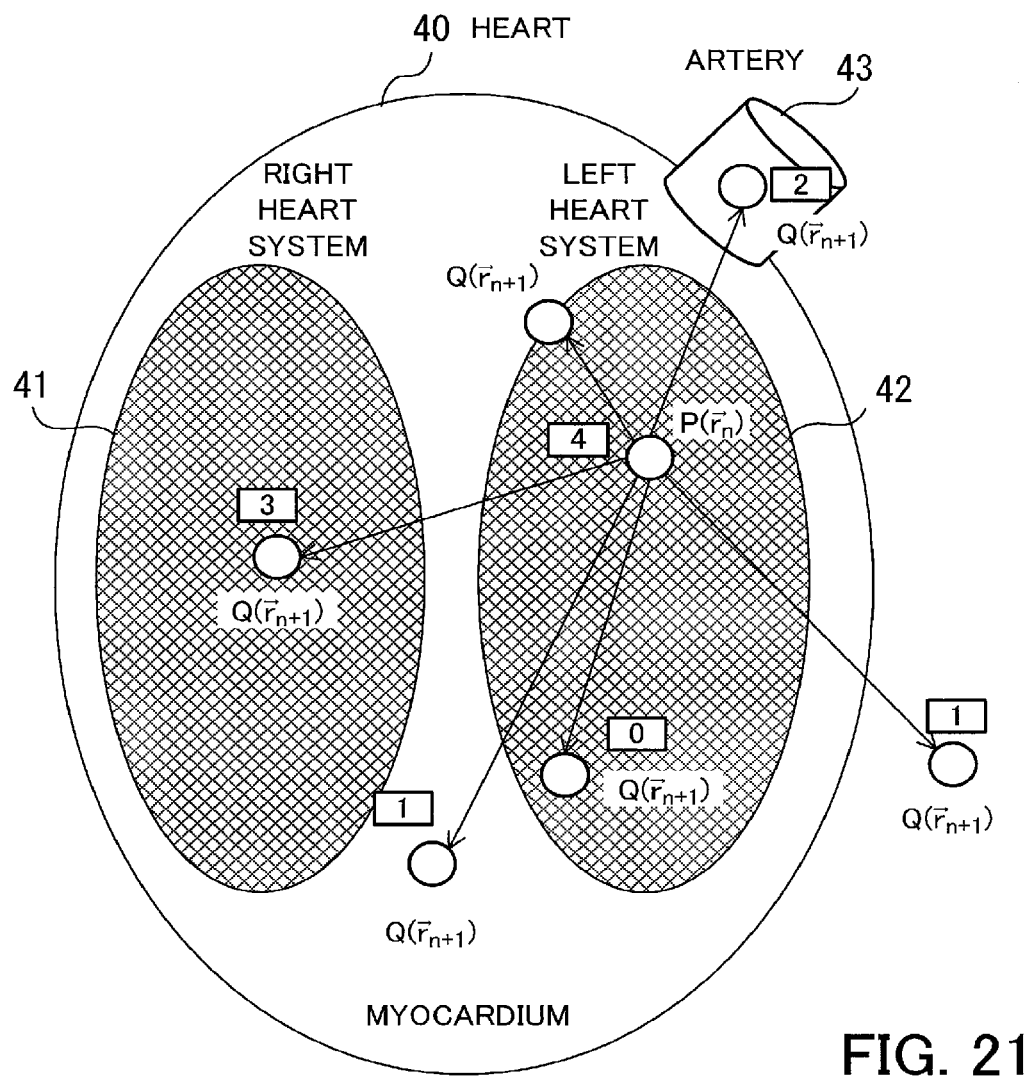
FIG. 21 illustrates examples of the positions that could be obtained as a result of calculation.

FIG. 21 illustrates examples of the positions that could be obtained as a result of calculation. The inside portions of a right heart system 41 and a left heart system 42 of a heart 40 are regions in which the analysis target fluid exists. The right heart system 41 includes a right atrium and a right ventricle.

In the second embodiment, the left heart system 42 includes a left atrium and a left ventricle. The blood flow inside an artery 43 connected to the left heart system 42 is not the analysis target. However, a part of the large artery may be included in the simulation.

When a point $P_{kj}$ exists in the fluid at the time point $t=t_k$, there are five possible destinations after the movement by time evolution as illustrated in FIG. 21. Each of the destinations is given a corresponding status variable (status). When the point has not moved over a myocardial wall and has fallen within an element of the analysis target fluid, the status variable represents "0". When the point has moved over a myocardial wall and has fallen outside an element of the analysis target fluid, the status variable represents "1". When the point has not moved over a myocardial wall and has fallen outside an element of the analysis target fluid, the status variable represents "2". When the point has moved over a myocardial wall and has fallen inside an element of the analysis target fluid, the status variable represents "3". When the point has not moved over a myocardial wall and has fallen on a boundary between the myocardium and an element of the analysis target fluid, the status variable represents "4".

FIG. 22 is a truth table indicating the status variables. The following description assumes that "P" represents a point before time evolution, which always exists in the fluid, and "Q" represents the destination point of the point P after time evolution. In addition, the following description assumes that the streakline calculation unit 150 performs determination only on the point Q. The streakline calculation unit 150 is able to set the status variable of the point Q by performing two kinds of determination processing.

The first determination processing is fluid determination in which the streakline calculation unit 150 determines whether the destination point Q exists in the fluid. If the point Q exists in the fluid, T is determined. If not, F is determined.

The second determination is line determination in which the streakline calculation unit 150 determines whether a line PQ formed by connecting the initial point P and the destination point Q crosses the myocardium or a surface thereof. If the line PQ crosses the myocardium (surface), T is determined. If not, F is determined. In the line determination, the number of intersections is also determined.

When the point Q exists in the fluid and the line PQ does not cross the myocardium, the streakline calculation unit 150 determines normal movement and sets "0" as the status variable.

When the point Q does not exist in the fluid and the line PQ crosses the myocardium (surface), the following two cases are possible: (1) the point Q has moved over the myocardium and fallen outside the system and (2) the point Q has been embedded in the myocardium. In either case, since recalculation needs to be performed, the streakline calculation unit 150 sets "1" as the status variable.

When the point Q does not exist in the fluid and the line PQ does not cross the myocardium (surface), the streakline calculation unit 150 determines that the point Q has fallen outside the simulation system via a large artery or the like and sets "2" as the status variable.

Even when the point Q exists in the fluid, there are cases in which impossible movement such as movement from the left atrium to the right atrium is determined. In such cases, while T is determined as the fluid determination, T is also determined as the line determination, and the number of intersections is always plural. Thus, when the number of intersections is 2 or more, the streakline calculation unit 150 sets "3" as the status variable.

When T is determined as the fluid determination and as the line determination, if the number of intersections is 1, the streakline calculation unit 150 determines that the point has fallen on a boundary surface of the fluid and the myocardium. Thus, the streakline calculation unit 150 sets "4" as the status variable.

Next, a procedure of the above status determination processing will be described.

Figure 23:
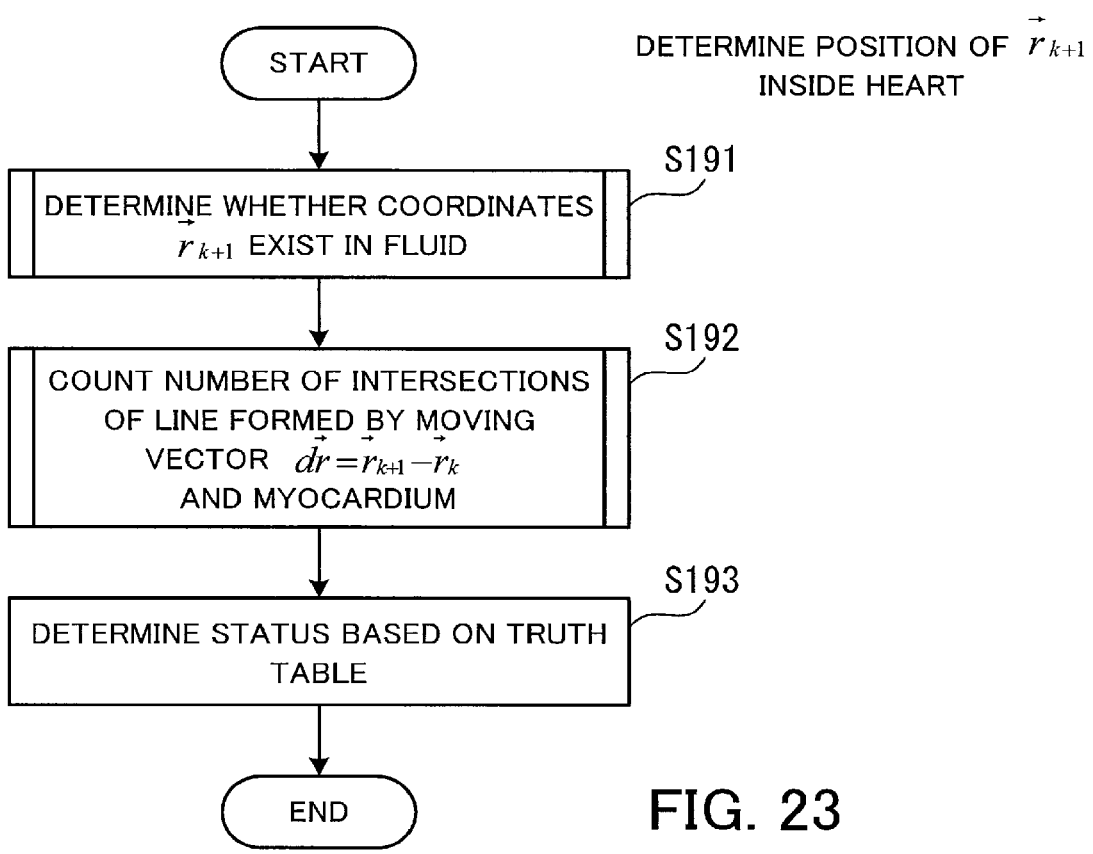
FIG. 23 is a flowchart illustrating an example of a procedure of processing for determining positions inside the heart.

FIG. 23 is a flowchart illustrating an example of a procedure of a processing for determining positions inside the heart. Hereinafter, the processing illustrated in FIG. 23 will be described step by step.

[Step S191] The streakline calculation unit 150 determines whether the coordinate vector $r_{k+1}$ after time evolution exists in the fluid. This processing will be described in detail with reference to FIG. 24.

[Step S192] The streakline calculation unit 150 determines whether a line having an infinite length formed by a moving vector dr=vector $r_{k+1}$–vector $r_k$ crosses the myocardium and counts the number of intersections of this line and the myocardium (surface). This processing will be described in detail with reference to FIG. 25.

[Step S193] The streakline calculation unit 150 determines the status based on the truth table illustrated in FIG. 22. Namely, each of the results of steps S191 and S192 is obtained as a truth value, i.e., true (T) or false (F). The result of step S193 is obtained as an integer of 0 or more. The streakline calculation unit 150 refers to the truth table and determines any one of the values "0" to "4" as the status variable of the heart corresponding to the return values obtained as the results of steps S191 to S193. The streakline calculation unit 150 uses the determination result as the position determination result.

In this way, the position determination is performed, and the status variable is determined.

Next, the processing (step S191) for determining whether a post-time-evolution position falls within the fluid will be described in detail.

Figure 24:
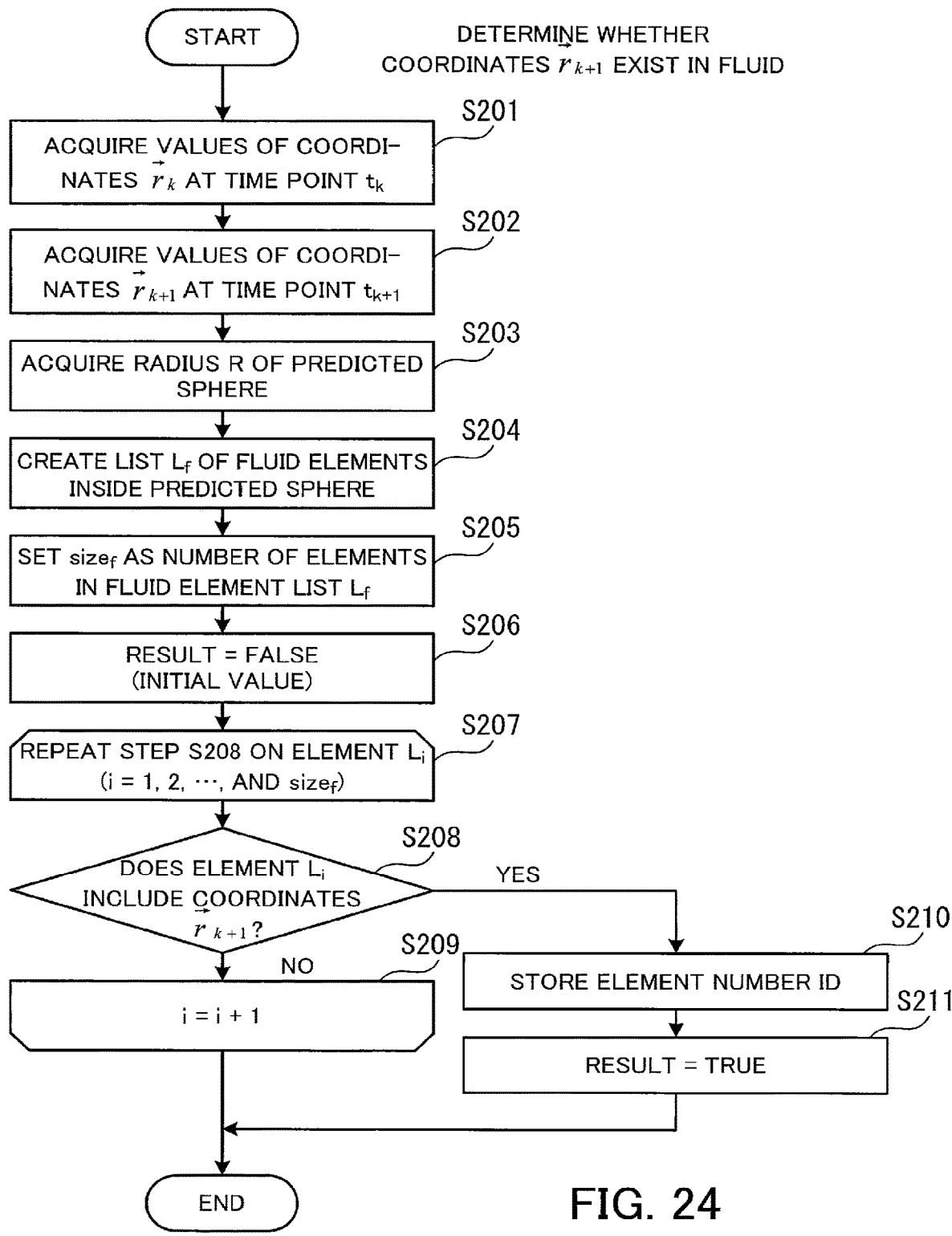
FIG. 24 is a flowchart illustrating an example of a procedure of processing for determining whether a post-time-evolution position falls within fluid.

FIG. 24 is a flowchart illustrating an example of a procedure of the processing for determining whether a post-time-evolution position falls within the fluid. In the example in FIG. 24, the streakline calculation unit 150 determines whether the coordinate vector $r_{k+1}$ exists in the fluid. Hereinafter, the processing illustrated in FIG. 24 will be described step by step.

[Step S201] The streakline calculation unit 150 acquires the coordinate vector $r_k$ at the time point $t_k$.

[Step S202] The streakline calculation unit 150 acquires the coordinate vector $r_{k+1}$ at the time point $t_{k+1}$.

[Step S203] The streakline calculation unit 150 acquires the radius R of the predicted sphere.

[Step S204] The streakline calculation unit 150 acquires a list (fluid element list $L_f$) of elements inside the predicted sphere having the coordinate vector $r_k$ as its center and having the radius R.

[Step S205] The streakline calculation unit 150 sets $size_f$ as the number of elements in the fluid element list $L_f$.

[Step S206] The streakline calculation unit 150 sets "F (False)" as the initial value of the result.

[Step S207] The streakline calculation unit 150 repeats step S208 on an individual element $L_i$ in the element list (i=1, 2, . . . , and $size_f$).

[Step S208] The streakline calculation unit 150 determines whether the element $L_i$ in the element list includes the coordinate vector $r_{k+1}$. If so, the processing proceeds to step S210. If not, the streakline calculation unit 150 proceeds to step S209.

[Step S209] Each time the streakline calculation unit 150 performs step S208, the streakline calculation unit 150 adds 1 to the index i and repeats step S208. When the streakline calculation unit 150 completes the processing on i=$size_f$, the streakline calculation unit 150 ends the processing for determining whether the post-time-evolution position falls within the fluid.

[Step S210] The streakline calculation unit 150 stores an element number ID of the element $L_i$ in a memory.

[Step S211] The streakline calculation unit 150 changes the result to "T (True)".

In this way, when the coordinates of the destination point are included in any of the elements, the streakline calculation unit 150 determines that the coordinate vector $r_{k+1}$ exists in the fluid and sets the return value to I (True). However, when the coordinates of the destination point are not included, the streakline calculation unit 150 sets the return value to F (False).

Next, the processing (step S192) for searching for an elastic body element through which a moving vector dr in the predicted sphere passes will be described in detail.

Figure 25:
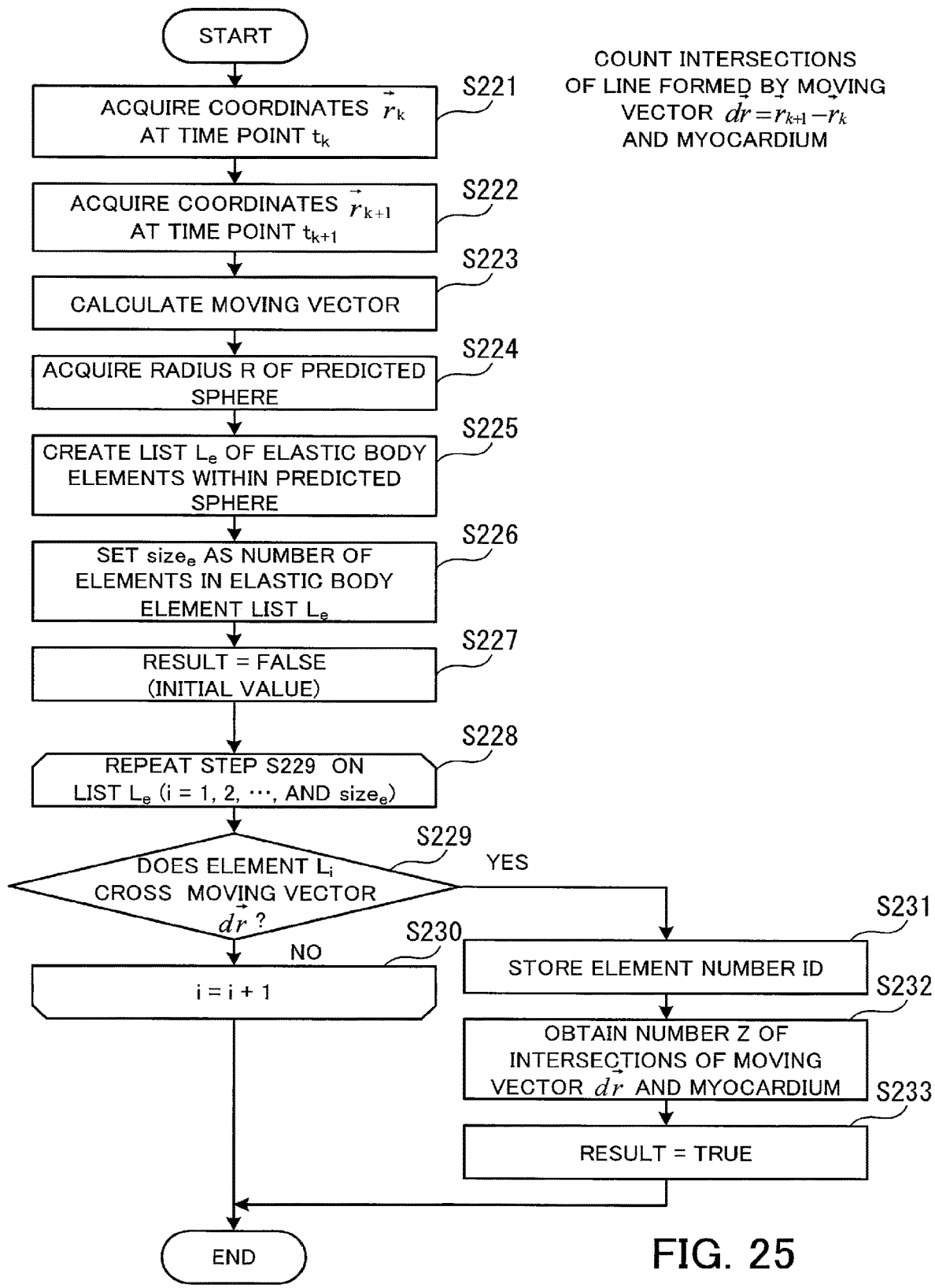
FIG. 25 is a flowchart illustrating an example of a procedure of processing for counting intersections of a line formed by a moving vector and a myocardium.

FIG. 25 is a flowchart illustrating an example of a procedure of the processing for counting intersections of a line formed by a moving vector and the myocardium. Hereinafter, the processing illustrated in FIG. 25 will be described step by step.

[Step S221] The streakline calculation unit 150 acquires the coordinate vector $r_k$ at the time point $t_k$.

[Step S222] The streakline calculation unit 150 acquires the coordinate vector $r_{k+1}$ at the time point $t_{k+1}$.

[Step S223] The streakline calculation unit 150 calculates the moving vector dr=vector $r_{k+1}$–vector $r_k$ from the acquired information. As a result, a line indicating the moving path of the point is defined.

[Step S224] The streakline calculation unit 150 acquires the value of the radius R of the predicted sphere.

[Step S225] The streakline calculation unit 150 creates a list (elastic body element list $L_e$) of elastic body elements inside the radius R of the predicted sphere.

[Step S226] The streakline calculation unit 150 sets $size_e$ as the number of elements in the elastic body element list $L_e$.

[Step S227] The streakline calculation unit 150 sets "F (False)" as the initial value of the result.

[Step S228] The streakline calculation unit 150 repeats step S229 on an individual element $L_i$ in the element list (i=1, 2, . . . , and $size_e$).

[Step S229] The streakline calculation unit 150 determines whether the i-th element $L_i$ crosses the line vector dr. Since the element $L_i$ is a polyhedron, the streakline calculation unit 150 obtains intersections of the line vector dr with respect to all of the surfaces of the element $L_i$. If the streakline calculation unit 150 determines no intersection on any of the surfaces of the element $L_i$, the streakline calculation unit 150 determines that the line vector dr does not cross the element. In this case, the processing proceeds to step S230. If the streakline calculation unit 150 determines that the line vector dr crosses the element, the processing proceeds to step S231.

[Step S230] Each time the streakline calculation unit 150 performs step S229, the streakline calculation unit 150 adds 1 to the index i and repeats step S229. When the streakline calculation unit 150 completes the processing on i=$size_e$, the streakline calculation unit 150 ends the processing for searching for an elastic body element through which the moving vector dr passes.

[Step S231] The streakline calculation unit 150 stores an element number ID of the element $L_i$ in a memory.

[Step S232] The streakline calculation unit 150 obtains the number Z (Z is an integer of 1 or more) of intersections of the moving vector dr indicating a line and the myocardial surface and stores the number Z in the memory 102.

[Step S233] The streakline calculation unit 150 changes the result to True.

As described above, when there is no intersection, the streakline calculation unit 150 determines that the line vector dr does not cross the element and sets the return value to F. In contrast, when there is at least one intersection, the streakline calculation unit 150 determines that the line vector dr crosses the element and sets the return value to T. In this case, the element number of the element having at least one intersection with the line vector dr and the number Z of intersections with the myocardial surface are stored.

By performing the above processing, the streakline calculation unit 150 is able to appropriately determine the status of the destination of the point. When the streakline calculation unit 150 determines the destination in this processing, by examining the elements in the predicted sphere as the destination determination targets, the streakline calculation unit 150 is able to perform the processing more efficiently. Next, a method for setting the radius R of the predicted sphere will be described in detail.

The streakline calculation unit 150 sets the predicted sphere based on how long the coordinate vector $r_k$ before time evolution is able to move within the time step $\Delta t$. In the case of the four-order Runge-Kutta method, the following inequality is established from expression (9).

$$|\vec{r}_{i+1} - \vec{r}_i| = \left|\frac{\Delta t}{6}(\vec{v}_1 + 2\vec{v}_2 + 2\vec{v}_3 + \vec{v}_4)\right| \leq \qquad (29)$$
$$\left|\frac{\Delta t}{6}(\vec{v}_{max} + 2\vec{v}_{max} + 2\vec{v}_{max} + \vec{v}_{max})\right| \leq |\Delta t \vec{v}_{max}|$$

Thus, by defining the radius R as indicated by expression (30), the radius R represents the maximum distance that the point P on the streakline moves within the time step $\Delta t$.

$$R = |\Delta t \vec{v}_{max}| \qquad (30)$$

In addition, the point P certainly exists inside the sphere after the time step $\Delta t$. In addition, the intermediate vector $v_i$ is also a point that exists inside the sphere having the radius R, which will be indicated as follows. Namely, expression (31) is established assuming that I=1 in expression (9), for example.

$$|\vec{r}_{i+1} - \vec{r}_i| = \left|\frac{\Delta t}{2}\vec{v}_1\right| \leq \left|\frac{\Delta t}{2}\vec{v}_{max}\right| \leq |\Delta t \vec{v}_{max}| \qquad (31)$$

Thus, coordinates indicated by the intermediate vector represent a point inside the sphere having the radius R. By performing the same operation when I=1, 2, 3, 4 in expressions (9), it is seen that all the intermediate vectors $v_I$ are also points inside the sphere having the radius R. This radius R is set as the radius of the predicted sphere. The streakline calculation unit 150 calculates the maximum value from the velocity field of the fluid for which the predicted sphere radius is set, as will be described below.

In accordance with expression (20), the velocity field is interpolated by a three-order polynomial. Thus, maximum values are numerically obtained at velocity field sections $[t_i, t_{i+1}]$ at individual grid points i. By selecting a maximum value from the obtained maximum values of the velocity fields at the individual grid points i, a point corresponding to the maximum norm of the velocity fields between these two time points is set as the maximum velocity |vector $v_{max}$|. Since this processing needs to be performed only once on a data set, if the maximum velocity |vector $v_{max}$| is stored as the pre-analysis result $\Omega$, this processing does not need to be performed subsequently. Next, when the time step width $\Delta t$ in the Runge-Kutta method is set, the maximum moving distance is determined to be R=|$\Delta t$ vector $v_{max}$|.

However, if the time step $\Delta t$ is too small, the predicted sphere radius R set as described above becomes smaller than the grid width (distance between neighboring grid points). Thus, there is a minimum value $R_{min}$ in discretization of grid points i. For example, the initial value of this minimum value $R_{min}$ is set to 0.001 [m] as an empirical minimum value. The minimum value may be calculated from a statistical analysis of grids.

Figure 26:
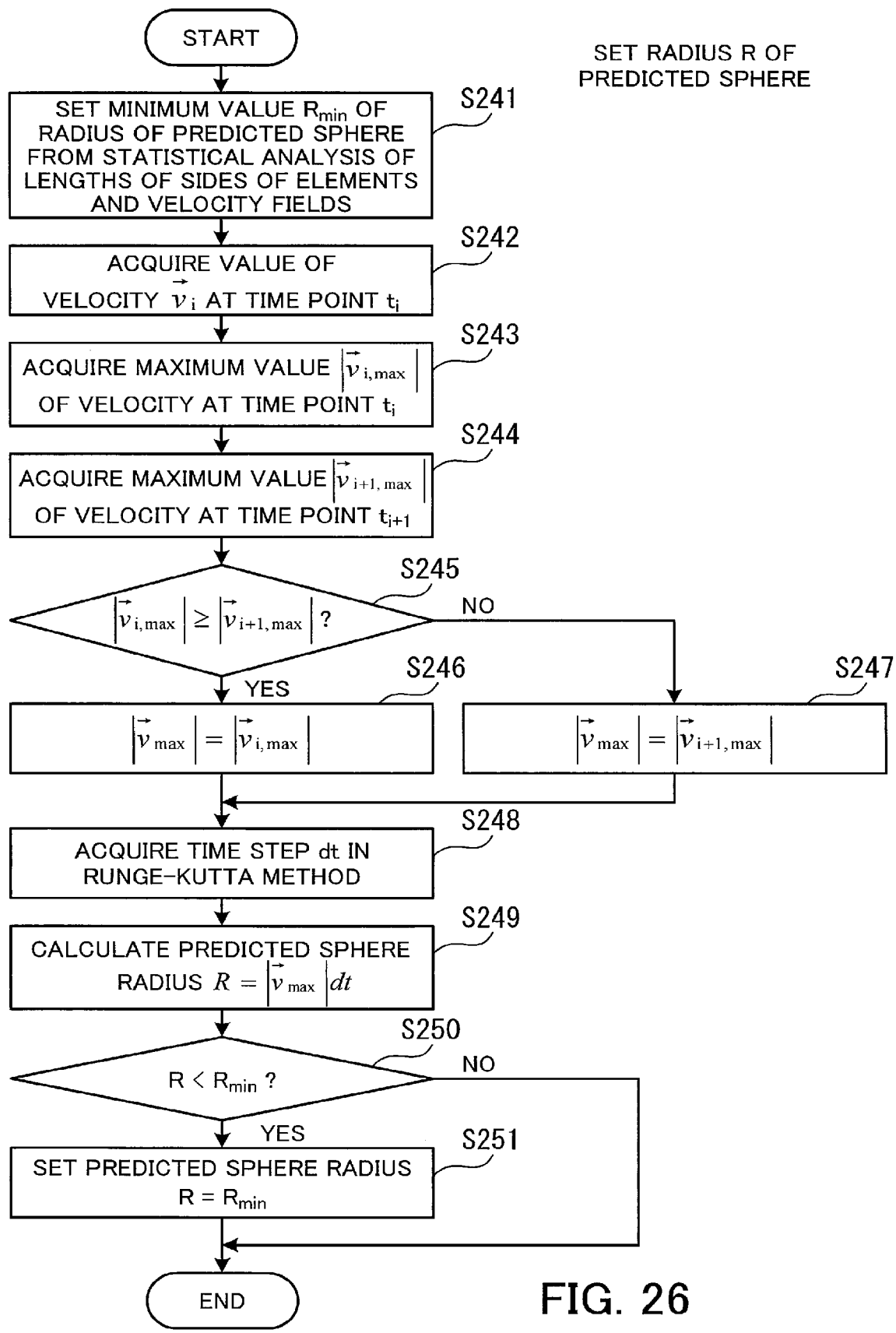
FIG. 26 is a flowchart illustrating an example of a procedure of processing for setting the radius of a predicted sphere.

When the radius R of the predicted sphere becomes smaller than the calculated $R_{min}$, the radius R of the predicted sphere is set to $R_{min}$. In this way, a situation where no element exists inside the predicted sphere is avoided. FIG. 26 illustrates a procedure of processing for setting the predicted sphere radius R as described above.

FIG. 26 is a flowchart illustrating an example of a procedure of processing for setting the predicted sphere radius. Hereinafter, the processing illustrated in FIG. 26 will be described step by step.

[Step S241] The streakline calculation unit 150 sets the minimum value $R_{min}$ of the radius of the predicted sphere from a statistical analysis of the velocity fields and the lengths of sides of elements.

[Step S242] The streakline calculation unit 150 acquires a value of a velocity vector $v_i$ at the time point $t_i$.

[Step S243] The streakline calculation unit 150 acquires a maximum value |vector $v_{i,max}$| of the velocity at the time point $t_i$.

[Step S244] The streakline calculation unit 150 acquires a maximum value |vector $v_{i+1,max}$| of the velocity at the time point $t_{i+1}$.

[Step S245] The streakline calculation unit 150 determines whether |vector $v_{i,max}$| is equal to or more than |vector $v_{i+1,max}$|. When |vector $v_{i,max}$| is equal to or more than |vector $v_{i+1,max}$|, the processing proceeds to step S246. When |vector $v_{i,max}$| is less than |vector $V_{i+1,max}$|, the processing proceeds to step S247.

[Step S246] The streakline calculation unit 150 sets |vector $v_{i,max}$| to |vector $v_{max}$|. Next, the processing proceeds to step S248.

[Step S247] The streakline calculation unit 150 sets |vector $v_{i+1,max}$| to |vector $v_{max}$|. Next, the processing proceeds to step S248.

[Step S248] The streakline calculation unit 150 acquires a time step dt in the Runge-Kutta method.

[Step S249] The streakline calculation unit 150 calculates |vector $v_{max}$|dt and sets the calculation result as the predicted sphere radius R.

[Step S250] The streakline calculation unit 150 determines whether the predicted sphere radius R is smaller than the minimum value $R_{min}$ of the predicted sphere radius. When the predicted sphere radius R is smaller than the minimum value $R_{min}$, the processing proceeds to step S251.

When the predicted sphere radius R is equal to or more than the minimum value $R_{min}$, the streakline calculation unit 150 ends the present processing.

[Step S251] The streakline calculation unit 150 sets the minimum value $R_{min}$ as the predicted sphere radius R. Next, the streakline calculation unit 150 ends the present processing.

By performing the above processing, the streakline calculation unit 150 is able to set an appropriate radius R for the predicted sphere.

In the second embodiment, the processing may be performed more quickly by performing the following processing.

[Improvement in Calculation Accuracy and Speed by Division Method]

In step S137 in FIG. 12, the time section $t_i \le t \le t_{i+1}$ at which output files are given is divided into $N_{div}$ time points. How the time section is divided will be described in detail.

In streakline calculation, of all the elements, only a small number of elements relate to the points on a single streakline. Thus, for reduction of the storage capacity and the calculation time, a predicted sphere is used. The calculation cost of a streakline increases in proportion to the radius $R^3$ of the predicted sphere. This will be explained as follows.

The number $N_{elem}$ of elements as the calculation targets is given by the following expression, assuming that the density of the spatial element number is ρ (vector r) as a function of a coordinate vector r.

$$N_{elem} = \frac{4\pi}{3}\rho(\vec{r})R^3 \tag{32}$$

Assuming that the density ρ (vector r) is approximately uniform, ρ (vector r)=$\rho_0$. Thus, $N_{elem} \propto R^3$.

Figure 27:
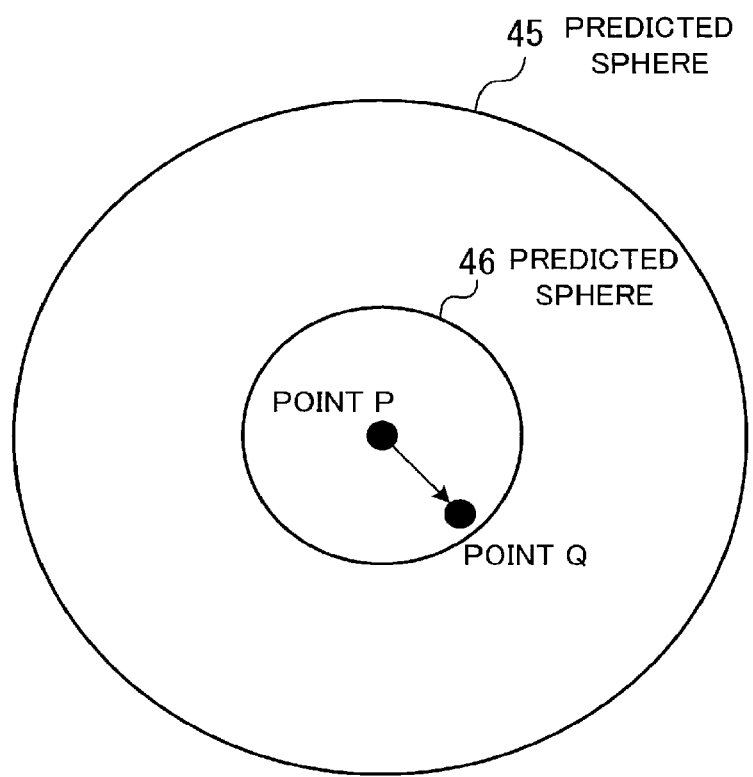
FIG. 27 illustrates a concept of reduction of the calculation amount achieved by time division.

When the time section $t_i \le t \le t_{i+1}$ is divided into $N_{div}$ time points, the number of time evolutions based on the Fourth-order Runge-Kutta method is $N_{div}$. Meanwhile, the predicted sphere radius is determined by expression (30). Thus, when the time step is $1/N_{div}$, the predicted sphere radius becomes also $1/N_{div}$. Since a single calculation amount is in proportion to the radius $R^3$ of the predicted sphere, the calculation amount is expressed by $N_{div}^{-3}$. Since this calculation is repeated $N_{div}$ times, the total calculation amount is expressed by $N_{div}^{-2}$. FIG. 27 schematically illustrates a concept of this calculation.

FIG. 27 illustrates a concept of reduction of the calculation amount achieved by time division. FIG. 27 assumes a case in which, a point Q, which is the destination of a point P, is calculated. When time division is not performed and a long time step is used, a large predicted sphere 45 having the point P as its center is analyzed. On the other hand, when time division is performed and a short time step is used, the movable range of the particle at the point P is reduced. Thus, it is preferable to analyze a predicted sphere 46 smaller than the predicted sphere 45. Namely, rather than performing a single calculation on the large predicted sphere 45, the streakline calculation unit 150 obtains the smaller predicted sphere 46 by dividing the time section into $N_{div}$ time points and obtaining segmented paths. As a result, the number of elements as the calculation targets is reduced, and the calculation amount is reduced.

Figure 28:
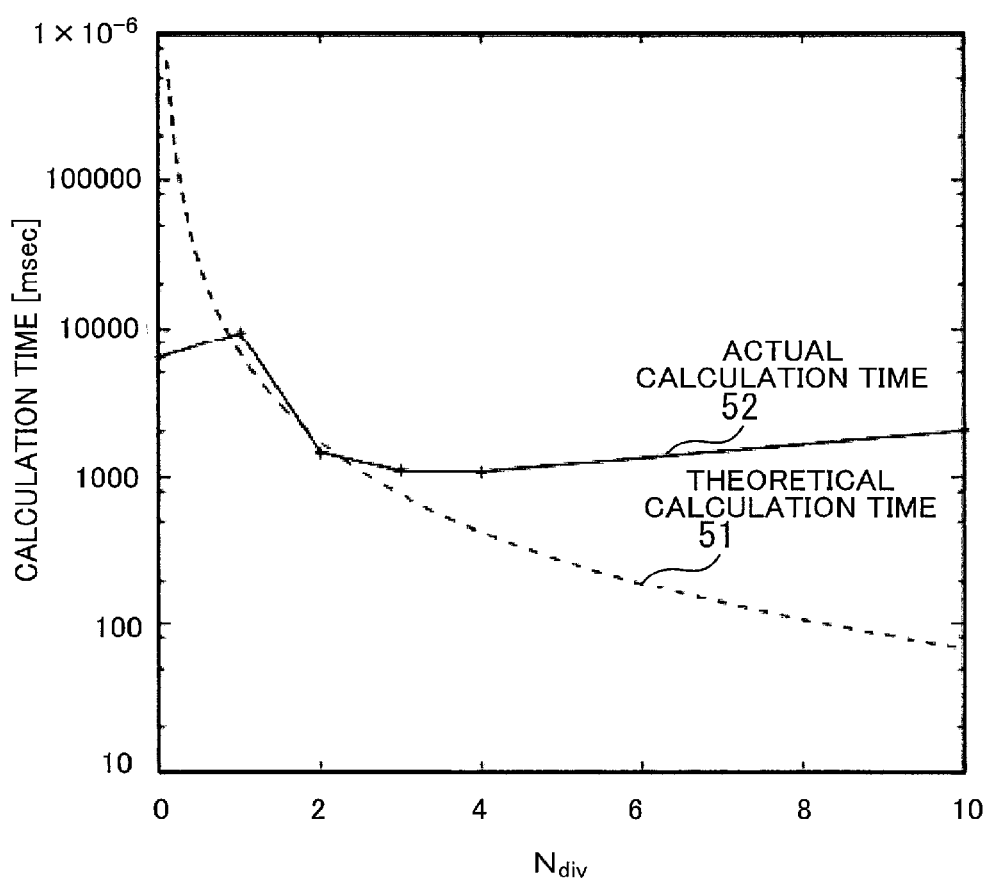
FIG. 28 illustrates an example of change of the total calculation time in accordance with the time division number.

FIG. 28 illustrates an example of change of the total calculation time in accordance with the time division number. In the graph in FIG. 28, the horizontal axis represents the division number $N_{div}$, and the vertical axis is the calculation time. In FIG. 28, a dashed line denotes transition of theoretical calculation time 51, and a solid line denotes transition of actual calculation time 52. The actual calculation time 52 is a measurement result of the total calculation time in the time section $t_i \le t \le t_{i+1}$. When $N_{div}$=0, a predicted sphere is not used, and all the elements are used as the calculation targets.

Theoretically, the larger the division number $N_{div}$ is, the shorter the calculation time will be. However, in practice, if the division number is too large, the number of times of processing performed per post-division unit time is increased, such as creation of a list of elements in the predicted sphere. Consequently, the processing time is increased. Thus, there is an optimum value as the division number $N_{div}$. For example, the streakline calculation unit 150 measures the optimum value as the division number $N_{div}$ in advance with respect to the target system while changing the division number $N_{div}$ before starting the calculation of a streakline.

[Determination Method of Minimum Value of Predicted Sphere Radius by Statistical Analysis]

A fluid simulation is performed by using a finite number of items of discrete point information. Thus, if an excessively small predicted sphere radius is set, no item of discrete point information could be included in the predicted sphere. This signifies that there is a lower limit as the predicted sphere radius. Simultaneously, since the predicted sphere radius is set by expression (30), there is a lower limit as the time step. When calculation is performed by using a predicted sphere, the lower limit $R_{min}$ as the predicted sphere radius is set. When the predicted sphere radius is equal to or less than the lower limit, the lower limit $R_{min}$ is set as the predicted sphere radius. When the predicted sphere radius is equal to or less than the lower limit, since $R_{min}$ larger than the predicted sphere radius is used, the point on the streakline does not fall outside the predicted sphere. Thus, to stably proceed with the calculation, setting the lower limit $R_{min}$ is important. In addition, the value of the lower limit $R_{min}$ relates to the setting of the time division number $N_{div}$. Since $R_0$=|Δt vector $v_{max}$| is the maximum moving distance, when the value of the lower limit $R_{min}$ is determined, the division number $N_{div}$ is set from the following expression by using a ceiling function.

$$N_{div} = \left\lceil \frac{R_0}{R_{min}} \right\rceil \tag{33}$$

Since the value of the division number $N_{div}$ relates to the calculation speed and the calculation accuracy, setting the lower limit $R_{min}$ is also important in the calculation speed and the calculation accuracy.

However, care needs to be taken in setting the lower limit $R_{min}$. Specifically, a probability model is introduced, and the streakline calculation unit 150 performs speculative calculation that allows calculation failure. When calculation fails, the streakline calculation unit 150 performs calculation by using parameters with which the calculation certainly succeeds. The time needed for this recalculation is considered as a penalty. The lower limit $R_{min}$ that statistically minimizes the calculation time including the penalty is set. Next, how the lower limit $R_{min}$ is set will be described in detail.

First, the streakline calculation unit 150 sets a radius $R_w$ as the worst value used as the penalty. The longest length of a side of an element used in the simulation is used as the radius $R_w$.

Figure 29:
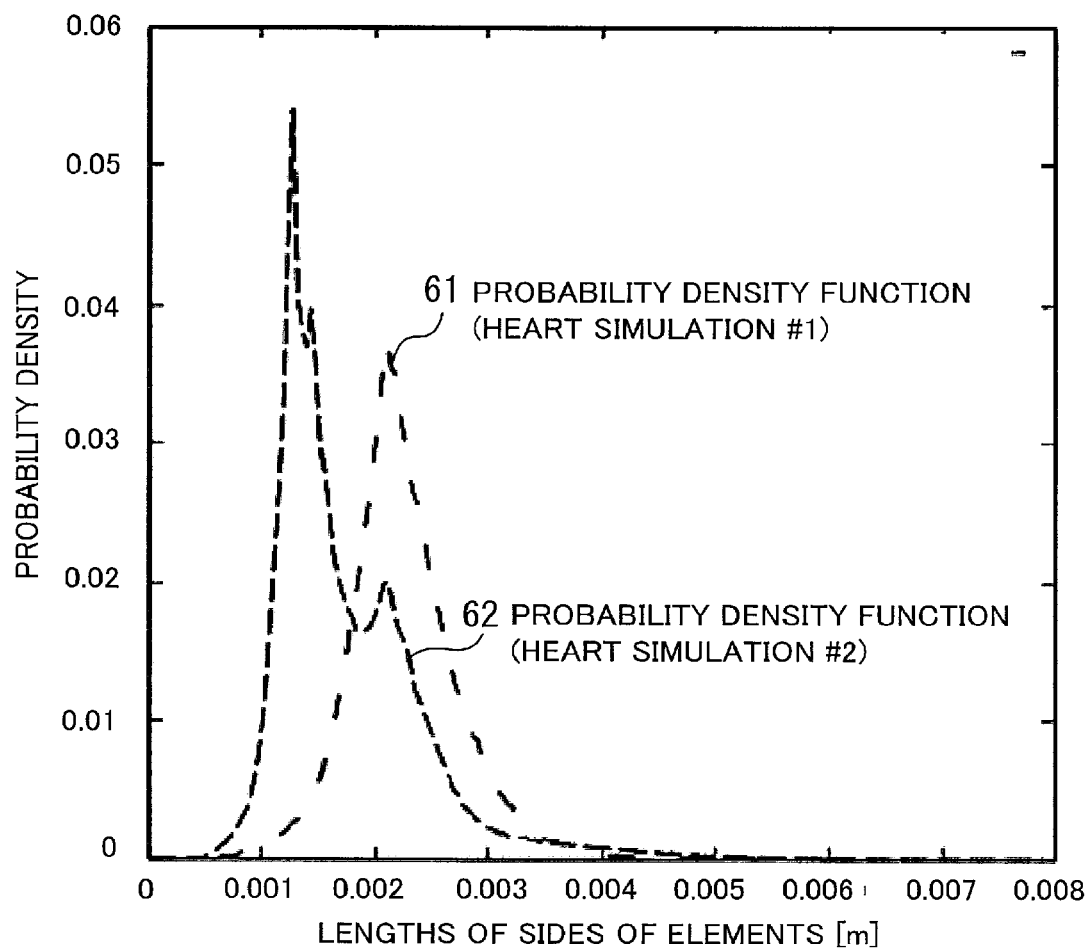
FIG. 29 illustrates an example of a distribution of lengths of sides of elements.

FIG. 29 illustrates an example of distribution of a length of a side of an element. In the graph in FIG. 29, the horizontal axis represents a length of a side of an element, and the vertical axis represents the probability density indicating each of the lengths of sides. In the graph, probability density functions 61 and 62 of two kinds of heart simulations #1 and #2 are represented by dashed lines.

In the example in FIG. 29, some of the elements used in the simulations are very rough, and the longest side is 0.008 [m]. Thus, if these elements are directly used for calculation, the division number $N_{div}$ is also decreased, and the speed is also decreased. However, most calculation may be performed without using the longest side.

After the radius $R_w$ as the worst value is set, the streakline calculation unit 150 sets the lower limit $R_{min}$ used for calculation. In this operation, the streakline calculation unit 150 calculates the statistical calculation cost while assuming failure of the calculation. In addition, in view of execution of speculative calculation, the streakline calculation unit 150 selects, as the lower limit $R_{min}$, a radius that minimizes the calculation amount including a penalty that occurs when the calculation fails. While this significantly depends on a probability model assumed, the speculative calculation will be described by using a simple example. First, the calculation using a point on a streakline assumes that all the elements could be analysis targets with equal probability. In this case, the calculation succeeds in accordance with the probability density functions 61 and 62 in FIG. 29.

The following description assumes that the calculation time is T when the radius is R. In this case, the corresponding calculation amount is in proportion to $R^3$. In addition, the following description assumes that the calculation succeeds with the probability p[%] by reducing the radius to βR (0<β≤1). A case in which the calculation succeeds is a case in which the destination of the point falls inside the predicted sphere having the radius R. When the calculation fails, recalculation is performed by using the radius R. In this case, calculation time T' including the penalty is expressed by expression (34).

$$\frac{T'}{T} = 1 - \int_0^{\beta R} p(L)dL + \beta^3 \tag{34}$$

Figure 30:
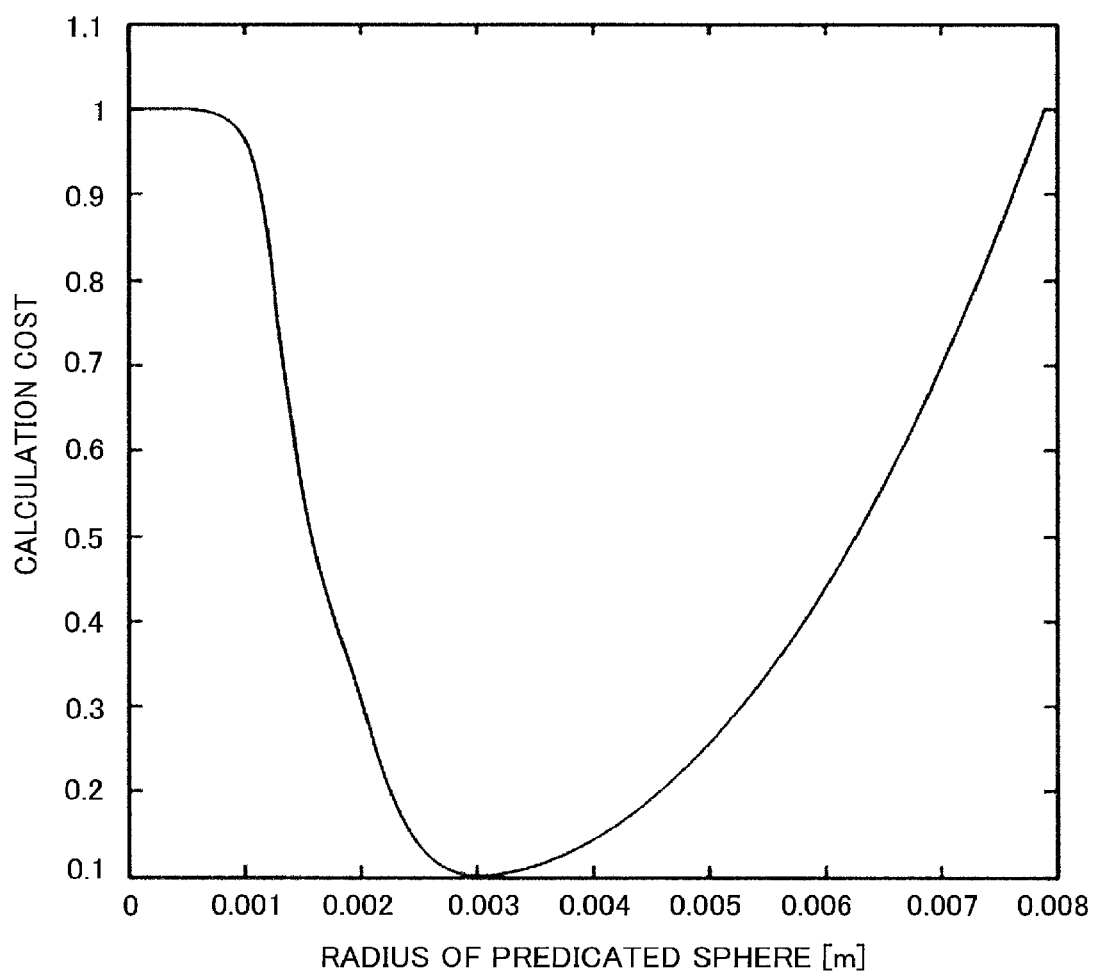
FIG. 30 illustrates change of the calculation cost based on the predicted sphere radius.

FIG. 30 illustrates change of the calculation cost based on the predicted sphere radius. In FIG. 30, the vertical axis represents the calculation cost (T'/T), and the horizontal axis represents the predicted sphere radius R. As illustrated in FIG. 30, it is seen that the cost including the penalty when the predicted sphere radius R is about 0.003 [m] is less than the cost including the penalty when the predicted sphere radius is the worst value radius $R_{max}$ (0.008 [m]) approximately by 10%. Namely, it is seen that there is a radius that achieves a statistically minimum calculation amount including the penalty. In practice, since a finite number of times of calculation is performed, all the elements are not used as the analysis targets with the equal probability. Thus, a smaller value than the above value is used as the radius.

In this case, while the fact that there is an optimum predicted sphere radius R may be indicated, the optimum value itself tends to be overestimated. Thus, to prevent such an overestimate, a distribution of moving distances as illustrated in FIG. 31 may be obtained by obtaining the norm of the velocity field at an individual discrete point and multiplying the time step by the norm.

Figure 31:
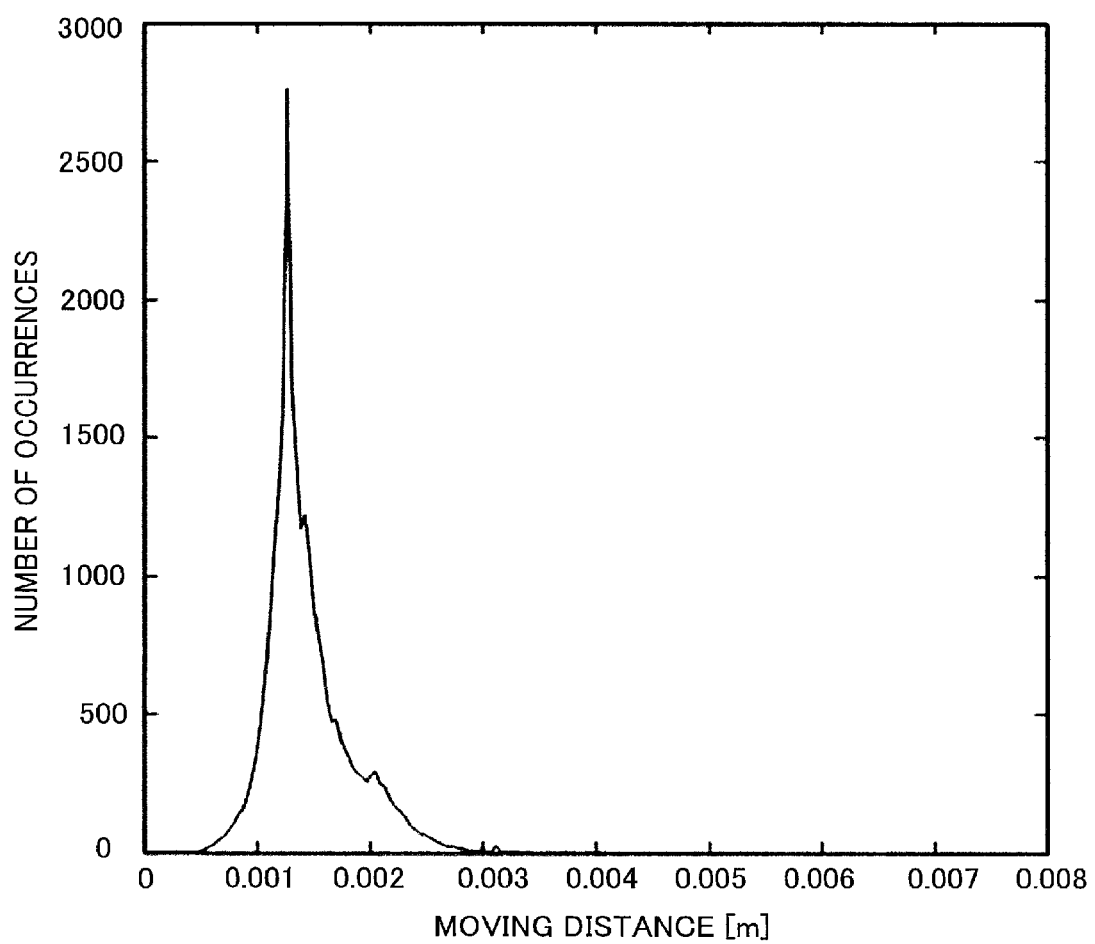
FIG. 31 illustrates a probability distribution of moving distances.
Figure 32:
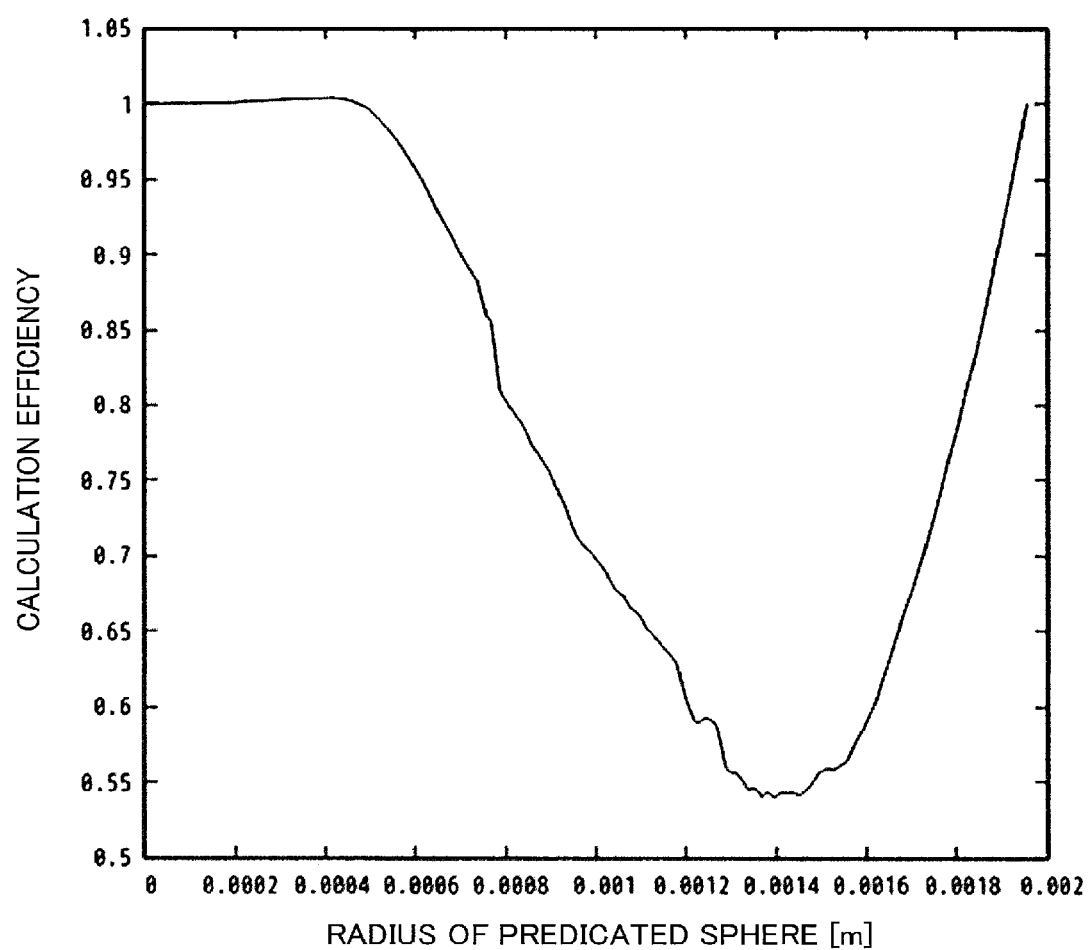
FIG. 32 illustrates a calculation efficiency curve when a probability distribution is assumed.

FIG. 31 illustrates a probability distribution of moving distances. In FIG. 31, the horizontal axis represents the moving distance, and the vertical axis represents the number of occurrences. Even when there are two tetrahedrons having the same shape and size, if the magnitude of the velocity field on one tetrahedron is twice as large as that on the other tetrahedron, the time needed for a point to pass through the target tetrahedron is reduced by half. FIG. 32 illustrates calculation efficiency including the penalty as a function of the predicted sphere radius R by using expression (34) based on the distribution of moving distances.

FIG. 32 illustrates a calculation efficiency curve when a probability distribution is assumed. In FIG. 32, the horizontal axis represents the predicted sphere radius R, and the vertical axis represents the calculation efficiency. A smaller calculation efficiency value indicates better efficiency. From FIG. 32, the best calculation efficiency corresponds to the predicted sphere radius R in the range of approximately from 0.0012 [m] to 0.0016 [m]. This is a model supporting that the empirical optimum value $R_{min}$=0.0015±0.0005 [m].

In this way, the optimum value of the predicted sphere radius R is obtained. Namely, while the streakline calculation unit 150 needs to perform recalculation as a penalty when a discrete point falls outside the predicted sphere, the streakline calculation unit 150 is able to set the most efficient radius R of the predicted sphere in view of this penalty. As a result, the efficiency of the streakline calculation is improved.

Specific Calculation Example

Hereinafter, the calculation speed measured when a streakline is actually calculated by causing the heart simulator to analyze the myocardium and coronary circulation will specifically be described.

First, data used in the calculation will be described. A simulation result corresponding to a single heartbeat was outputted, and 100 heart state data was outputted per 0.01 [sec]. Since the heart pulsates, the velocity field changes over time. Thus, the velocity field is an unsteady flow. In addition, the myocardium repeats relaxation and contraction because of the pulsation. Thus, the myocardial surfaces also move, resulting in a moving boundary problem. To describe transfer of the blood flow in the heart in this system, particle generation sources were arranged at a plurality of points in the heart, and streaklines were calculated.

When the visualization apparatus 100 read information about the myocardium and the fluid from the outside, the number M of streaklines and the number N of times of calculation were inputted to the visualization apparatus 100. In addition, the positions of the streakline generation sources were inputted to the visualization apparatus 100. The streakline generation sources were arranged in the left ventricle and the right atrium in the heart. In accordance with the instruction of the arrangement of the streakline generation sources, for example, the visualization apparatus 100 randomly arranged streakline generation sources in the individual fluid portion inside the sphere having a radius of 0.05 [m]. In addition, the number of times of calculation was set to 30, which corresponded to 0.3 heartbeat. The time evolution calculation was performed by using the fourth-order Runge-Kutta method.

After setting the above initial conditions, when the visualization apparatus 100 started streakline calculation, particles were generated from the particle generation sources per step. The position of an individual particle after the time step Δt=0.01 [sec] was calculated in accordance with the streakline calculation flowchart illustrated in FIG. 9. The streaklines calculated were displayed on the monitor 21.

Figure 33:
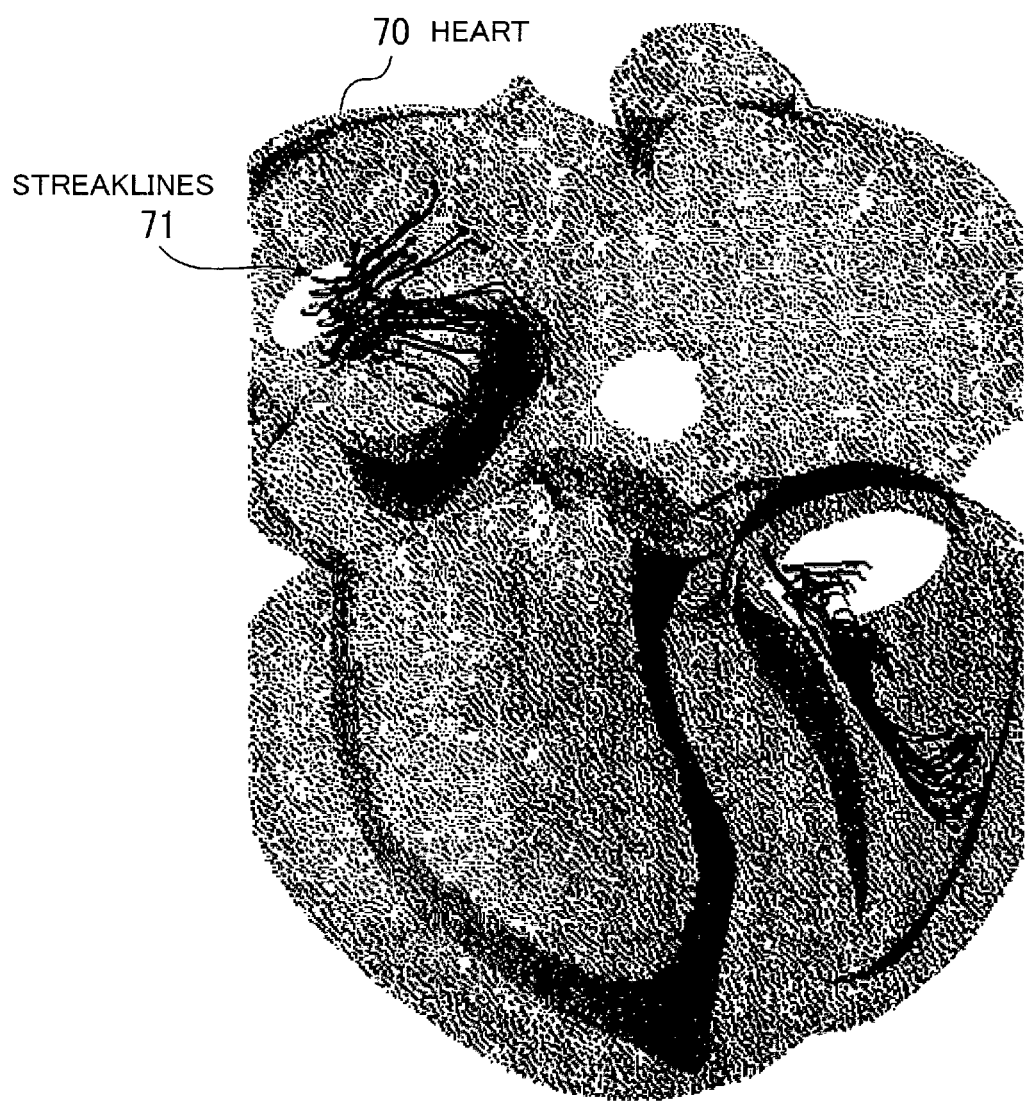
FIG. 33 illustrates an example of display of streaklines.

FIG. 33 illustrates an example of display of streaklines. In the example in FIG. 33, a plurality of streaklines 71 are superimposed on a sectional image of a heart 70.

When calculating streaklines, the streakline calculation unit 150 uses a predicted sphere to reduce the calculation amount and improve the calculation accuracy. In the calculation using a predicted sphere, the time step $\Delta t=0.01$ [sec] was further divided by the division number $N_{div}$. As the division number $N_{div}$, an optimum value that would achieve a statistically minimum calculation amount was automatically set. In this simulation, the division number $N_{div}$ was set to approximately 3 to 7.

The calculation speed was quantitatively measured through optimization by using the division number $N_{div}$, and FIG. 28 illustrates a result of the measurement. The example in FIG. 28 also illustrates the calculation time of a streakline when no predicted sphere was used, so as to clarify the advantageous effect obtained by use of a predicted sphere. $N_{div}=0$ corresponds to the time needed when no predicted sphere was used, namely, when all the elements were used as the calculation targets.

When a predicted sphere is used ($N_{div}=1$), namely, when the time division is not performed substantially, time is needed to establish the predicted sphere. Thus, more time is needed than the case in which no predicted sphere is used (about 1.47 times). However, when $N_{div}=2$, the effect of the reduction of the calculation cost in proportion to $N_{div}^{-2}$ becomes larger than the fixed cost of establishing the predicted sphere. Thus, the calculation time is reduced by about 22.9%, compared with the case in which no predicted sphere is used. While the calculation time shortens as the division number $N_{div}$ increases, it is seen that there is an upper limit in performance improvement because of the fixed cost of establishing the predicted sphere. In the example in FIG. 28, the best division number is 4. If the division number $N_{div}$ is increased further, since the effect of the fixed cost has more impact, the calculation time starts to increase. When $N_{div}=10$, the performance is deteriorated by about 53%, compared with the best case.

As described above, while there is an optimum value for the division number $N_{div}$, the best division number is set before a streakline is calculated in actual calculation. In addition, in the calculation in FIG. 28, since the number of grid points is no more than approximately 50,000, the calculation time is shorter in the case in which no predicted sphere is used than the case in which the predicted sphere is used and the division number $N_{div}$ is 1. However, if the simulation system is increased, the calculation amount of the case in which no predicted sphere is used increases in proportion to the number of grid points. For example, if the grid number is increased 10 times, the time is increased 10 times. However, when a predicted sphere is used, since the predicted sphere radius R is set only based on the maximum value of the velocity and the time step and is always constant, the calculation amount is also constant. Thus, the larger the system on which the simulation is performed is, the greater the advantageous effect obtained by use of the predicted sphere will be.

In addition, another advantageous effect, which is improvement in accuracy, obtained by the time division on a predicted sphere will be described. While expressions (9) to (10) are given in the case of the fourth-order Runge-Kutta method, it is known that the error order is given as $O(\Delta t^4)$. Thus, when the time is divided by the division number $N_{div}$, the error in a single Runge-Kutta operation results in $N_{div}^{-4}$ times. Even when calculation based on the Runge-Kutta method $N_{div}$ times in total in the time section $t_i \le t \le t_{i+1}$ and the error is accumulated $N_{div}$ times, the total error remains $N_{div}^{-3}$. When the division number $N_{div}$ is 4, the total error is 1/64 times.

Figure 34:
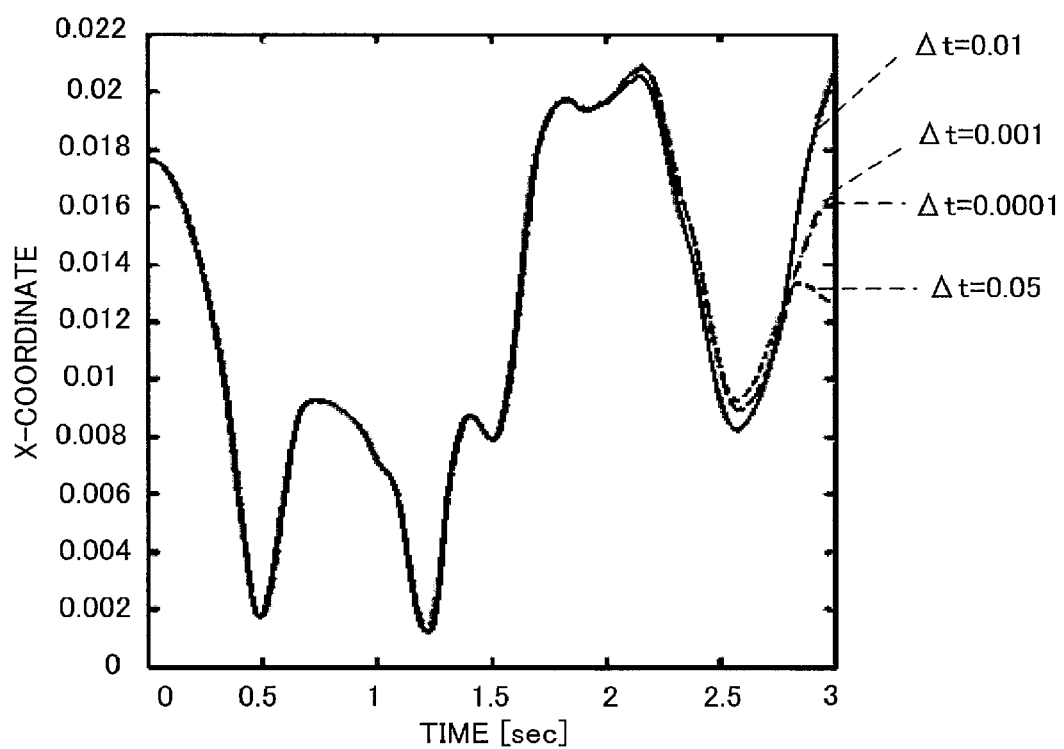
FIG. 34 illustrates change of the accuracy of a trajectory when the time step is changed.

FIG. 34 illustrates change of the accuracy of a trajectory when the time step is changed. In FIG. 34, the horizontal axis represents the simulation time, and the vertical axis represents the x coordinates of a discrete point. The example in FIG. 34 illustrates the temporal change (trajectory) of the x coordinates of a certain discrete point when the time step $\Delta t$ is set to "0.01", "0.05", "0.001", and "0.0001".

When the coordinate change amount after the integration is small or when the number of integration operations is small, the trajectory does not change regardless of the time step. However, in a region (time $t>2.5$ [sec]) in which the number of integration operations is large, the trajectory corresponding to when the time step $\Delta t=0.01$ [sec] is significantly shifted from the trajectories corresponding to when the time step $\Delta t=0.001$ [sec] and 0.0001 [sec], respectively. However, the trajectories corresponding to when the time step $\Delta t=0.001$ [sec] and $\Delta t=0.0001$ [sec] are very close to each other. Thus, it is seen that accumulation of calculation errors is prevented by reducing the time step.

As described above, setting the division number $N_{div}$ is important in the calculation speed and the calculation accuracy. In addition, the division number $N_{div}$ is set depending on the minimum value $R_{min}$ of the predicted sphere radius. In actual calculation, a probability model is assumed in view of both the velocity field and lengths of sides of elements as illustrated in FIG. 31, and a probability distribution is calculated. In addition, from the probability distribution, the calculation efficiency is calculated by using expression (34), and the minimum value $R_{min}$ that achieves the best calculation efficiency is calculated. Namely, as illustrated in FIG. 32, there is a minimum value as the radius of the predicted sphere, and the minimum value $R_{min}$ is about $0.0015 \pm 0.0005$ [m]. Thus, the calculation is always performed at the minimum calculation cost.

Next, calculation stability will be described. In the second embodiment, the individual velocity field is calculated in accordance with expression (4) by taking into consideration correction based on the motion of ALE grid coordinates.

Figure 35:
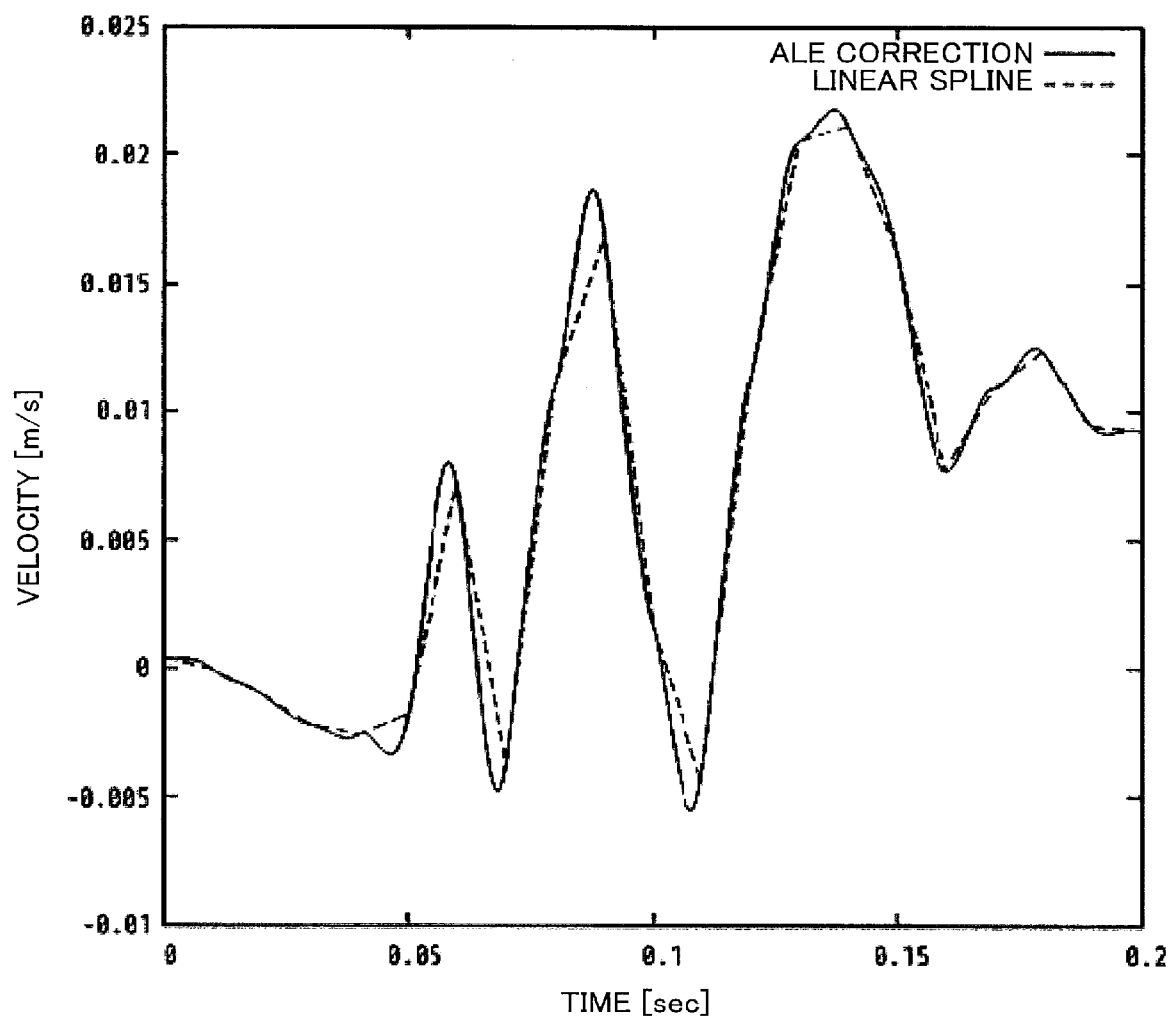
FIG. 35 illustrates an example of a velocity field to which correction of the motion of ALE grid points has been added.

FIG. 35 illustrates an example of a velocity field to which correction of the motion of ALE grid points has been added. FIG. 35 illustrates a calculation result of change of the velocity (a dotted line) when evaluation of a velocity field is performed by linear interpolation and a calculation result of change of a velocity (a solid line) when correction of the apparent force caused by the motion of ALE grid coordinates is performed in accordance with expression (4).

While there are cases in which linear interpolation approximation achieves a very good result, if linear approximation is used for evaluation of a velocity field in a region ($[0.03 \le t \le 0.1]$) in which the velocity field rapidly changes with respect to time, the evaluation accuracy of the velocity field is deteriorated. In such a region in which the evaluation accuracy of the velocity field is poor, since a large numerical error occurs, a streakline could enter the myocardium when the streakline is calculated. This is schematically illustrated in FIG. 36.

Figure 36:
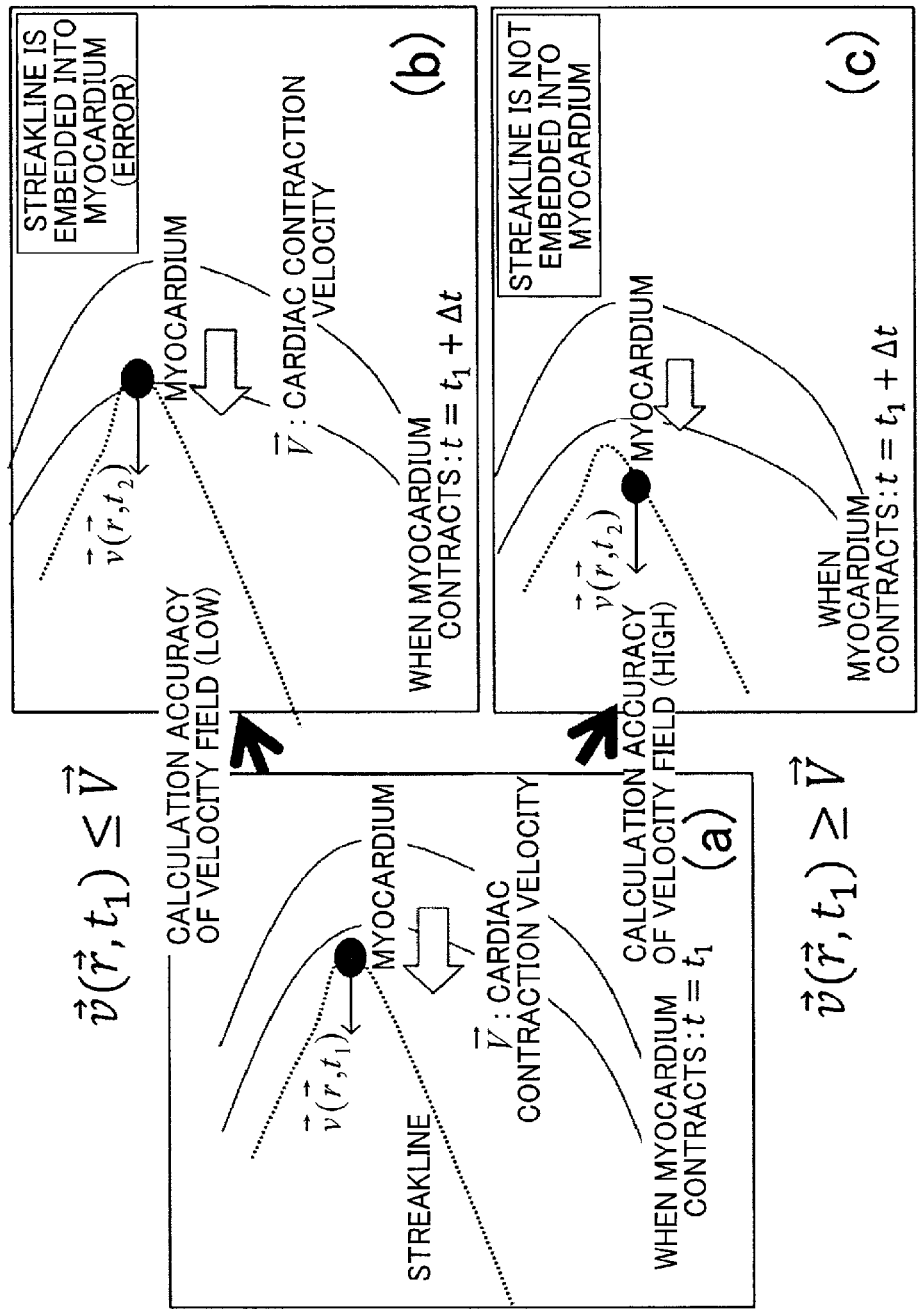
FIG. 36 illustrates an advantageous effect of preventing streaklines from being embedded into the myocardium, the effect obtained as a result of improvement in calculation accuracy.

FIG. 36 illustrates an advantageous effect of preventing streaklines from being embedded into the myocardium, the effect obtained as a result of improvement in calculation accuracy. When a streakline exists near the myocardium in a cardia contraction period, the points on the streakline near the myocardium motion in the moving direction of the myocardium.

If the calculation accuracy of the velocity field is low, the velocity field is underestimated, and the velocity of a point on the streakline could be calculated lower than an accurate value. If the velocity of a point on the streakline near the myocardium is underestimated and is lower than the cardiac contraction velocity, the myocardium overtakes the point on the streakline. As a result, the streakline is embedded into the myocardium. Once a point on the streakline is embedded into the myocardium, since no velocity field of the fluid is defined on the myocardium, the calculation fails.

To avoid this circumstance, the second embodiment corrects the motion of ALE grid coordinates in accordance with expression (4) when a velocity field is calculated. In this way, since the calculation accuracy of the velocity field is improved, the velocity of an individual point on a streakline near the myocardium is less frequently made lower than the cardiac contraction velocity and the myocardium less frequently overtakes any point on the streakline. As a result, the circumstance in which a streakline is embedded into the myocardium is avoided.

As described above, by correcting the apparent force caused by the accelerated motion of an individual grid point itself, the calculation stability of the streakline visualization apparatus is improved.

OTHER EMBODIMENTS

The points on a streakline are independent of each other without interacting with each other. Thus, since parallelization is suitably applicable, calculation of streaklines may be performed in a parallel manner by using Message Passing Interface (MPI) or Open Multi-Processing (OpenMP). In this way, the calculation speed is improved.

In addition, while an example in which streaklines of the blood flow are visualized by using results of a heart simulation has been illustrated in the second embodiment, the second embodiment is also applicable to results of other fluid simulations. For example, when a variable wing mechanism is arranged on a rear portion of an automobile, the flow of the air around the variable wing mechanism when the variable wing mechanism is activated may be simulated and analyzed. By using the visualization apparatus 100 according to the second embodiment, the flow of the air around the variable wing mechanism when the variable wing mechanism is activated is visualized by streaklines. In addition, the second embodiment is also applicable to fluid simulation results indicating the flow of the air around a swing wing of an airplane when the wing swings.

According to one aspect, streaklines are tracked even when the structure deforms.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A streakline visualization apparatus comprising:
a memory configured to store fluid information including position information indicating positions of a plurality of grid points that move with accelerated motion in an analysis space as analysis time of a fluid simulation progresses, at each of a plurality of first time points having a first time interval and including velocity information indicating velocities of fluid on the plurality of grid points at each of the plurality of first time points; and
a processor coupled to the memory and configured to perform a procedure including:
calculating, based on the position information, a grid point moving velocity and a grid point moving acceleration of each of the plurality of grid points at each of the plurality of first time points;
calculating, based on the fluid information and by using an expression including the grid point moving velocity and the grid point moving acceleration as variables for correcting an error attributable to the accelerated motion of the plurality of grid points represented by the position information, time differential values of the velocities of the fluid on the plurality of grid points at each of the plurality of first time points,
calculating, based on the velocities and the time differential values of the velocities of the fluid on the plurality of grid points at each of the plurality of first time points, positions of a series of particles sequentially output from a particle generation source as the analysis time progresses at each of a plurality of second time points having a second time interval shorter than the first time interval, and
generating display information about a streakline indicating the series of the particles.

2. The streakline visualization apparatus according to claim 1, wherein calculating the positions includes generating interpolation curves, each of which connects first positions indicating the velocities of the fluid on a corresponding one of the plurality of grid points at the plurality of first time points, each of which has a slope based on the time differential values of the velocities of the fluid indicated by the first positions respectively corresponding to the plurality of first time points, and each of which represents change in velocity of the fluid over time, and calculating, based on the individual interpolation curves of the plurality of grid points, the positions of the series of the particles at each of the plurality of second time points.

3. The streakline visualization apparatus according to claim 1,
wherein the memory further stores structure information indicating change of a shape of a structure in the analysis space over time, and
wherein, when calculating a second streakline at a second analysis time point, based on a first streakline at a first analysis time point, the procedure further includes setting a partial region including a discrete point at a first position on the first streakline in the analysis space as an analysis target region of the discrete point, calculating, based on the velocities of the fluid in the analysis target region, the velocities indicated by the fluid information, a second position indicating a destination of a particle on the discrete point at the second analysis time point, determining, based on information about the structure in the analysis target region, the information indicated by the structure information, a region occupied by the structure in the analysis target region at the second analysis time point, determining entrance or non-entrance of the second streakline into the occupied region, based on the first position and the second position, and generating display information about the second streakline passing through the second position, when determining that the second streakline does not enter the occupied region.

4. The streakline visualization apparatus according to claim 1, wherein the procedure further includes displaying the streakline, based on the display information.

5. A streakline visualization method comprising:
calculating, by a processor, based on fluid information including position information indicating positions of a plurality of grid points that move with accelerated motion in an analysis space as analysis time of a fluid simulation progresses, at each of a plurality of first time points having a first time interval and including velocity information indicating velocities of fluid on the plurality of grid points at each of the plurality of first time points, a grid point moving velocity and a grid point moving acceleration of each of the plurality of grid points at each of the plurality of first time points;
calculating, by the processor, based on fluid information, by using an expression including the grid point moving velocity and the grid point moving acceleration as variables for correcting an error attributable to the accelerated motion of the plurality of grid points represented by the position information, time differential values of the velocities of the fluid on the plurality of grid points at each of the plurality of first time points;
calculating, by the processor, based on the velocities and the time differential values of the velocities of the fluid on the plurality of grid points at each of the plurality of first time points, positions of a series of particles sequentially output from a particle generation source as the analysis time progresses at each of a plurality of second time points having a second time interval shorter than the first time interval; and
generating display information about a streakline indicating the series of the particles.

6. The streakline visualization method according to claim 5, wherein calculating the positions includes generating interpolation curves, each of which connects first positions indicating the velocities of the fluid on a corresponding one of the plurality of grid points at the plurality of first time points, each of which has a slope based on the time differential values of the velocities of the fluid indicated by the first positions respectively corresponding to the plurality of first time points, and each of which represents change in velocity of the fluid over time, and calculating, based on the individual interpolation curves of the plurality of grid points, the positions of the series of the particles at each of the plurality of second time points.

7. The streakline visualization method according to claim 5, further comprising:
storing structure information indicating change of a shape of a structure in the analysis space over time, and
wherein, when calculating a second streakline at a second analysis time point, based on a first streakline at a first analysis time point, further including setting a partial region including a discrete point at a first position on the first streakline in the analysis space as an analysis target region of the discrete point, calculating, based on the velocities of the fluid in the analysis target region, the velocities indicated by the fluid information, a second position indicating a destination of a particle on the discrete point at the second analysis time point, determining, based on information about the structure in the analysis target region, the information indicated by the structure information, a region occupied by the structure in the analysis target region at the second analysis time point, determining entrance or non-entrance of the second streakline into the occupied region, based on the first position and the second position, and generating display information about the second streakline passing through the second position, when determining that the second streakline does not enter the occupied region.

8. A non-transitory computer-readable storage medium storing a computer program that causes a computer to perform a procedure comprising:
calculating, by a processor, based on fluid information including position information indicating positions of a plurality of grid points that move with accelerated motion in an analysis space as analysis time of a fluid simulation progresses, at each of a plurality of first time points having a first time interval and including velocity information indicating velocities of fluid on the plurality of grid points at each of the plurality of first time points, a grid point moving velocity and a grid point moving acceleration of each of the plurality of grid points at each of the plurality of first time points;
calculating, based on fluid information including position information, by using an expression including the grid point moving velocity and the grid point moving acceleration as variables for correcting an error attributable to the accelerated motion of the plurality of grid points represented by the position information, time differential values of the velocities of the fluid on the plurality of grid points at each of the plurality of first time points;
calculating, based on the velocities and the time differential values of the velocities of the fluid on the plurality of grid points at each of the plurality of first time points, positions of a series of particles sequentially output from a particle generation source as the analysis time progresses at each of a plurality of second time points having a second time interval shorter than the first time interval; and
generating display information about a streakline indicating the series of the particles.

9. The non-transitory computer-readable storage medium storing according to claim 8, wherein the procedure further comprises:
calculating the positions includes generating interpolation curves, each of which connects first positions indicating the velocities of the fluid on a corresponding one of the plurality of grid points at the plurality of first time points, each of which has a slope based on the time differential values of the velocities of the fluid indicated by the first positions respectively corresponding to the plurality of first time points, and each of which represents change in velocity of the fluid over time, and calculating, based on the individual interpolation curves of the plurality of grid points, the positions of the series of the particles at each of the plurality of second time points.

10. The non-transitory computer-readable storage medium storing according to claim 8, wherein the procedure further comprises:
store structure information indicating change of a shape of a structure in the analysis space over time, and
wherein, when calculating a second streakline at a second analysis time point, based on a first streakline at a first analysis time point, the procedure further includes setting a partial region including a discrete point at a first position on the first streakline in the analysis space as an analysis target region of the discrete point, calculating, based on the velocities of the fluid in the analysis target region, the velocities indicated by the fluid information, a second position indicating a destination of a particle on the discrete point at the second analysis time point, determining, based on information about the structure in the analysis target region, the information indicated by the structure information, a region occupied by the structure in the analysis target region at the second analysis time point, determining entrance or non-entrance of the second streakline into the occupied region, based on the first position and the second position, and generating display information about the second streakline passing through the second position, when determining that the second streakline does not enter the occupied region.

\* \* \* \* \*